United States Patent
Schmidt et al.

(10) Patent No.: US 10,711,050 B2
(45) Date of Patent: Jul. 14, 2020

(54) VARIANT SERUM ALBUMIN WITH IMPROVED HALF-LIFE AND OTHER PROPERTIES

(71) Applicant: Albumedix LTD, Nottingham (GB)

(72) Inventors: Michael March Schmidt, Boston, MA (US); Eric Steven Furfine, Concord, MA (US); Amy Jada Andreucci, Woburn, MA (US); Thomas M. Barnes, Cambridge, MA (US)

(73) Assignee: ALBUMEDIX LTD, Nottingham (GB)

( * ) Notice: Subject to any disclaimer, the term of this patent is extended or adjusted under 35 U.S.C. 154(b) by 0 days.

(21) Appl. No.: 15/989,985

(22) Filed: May 25, 2018

(65) Prior Publication Data

US 2018/0334491 A1 Nov. 22, 2018

Related U.S. Application Data

(63) Continuation of application No. 14/358,857, filed as application No. PCT/US2012/065733 on Nov. 18, 2012, now abandoned.

(60) Provisional application No. 61/710,476, filed on Oct. 5, 2012, provisional application No. 61/576,491, filed on Dec. 16, 2011, provisional application No. 61/561,785, filed on Nov. 18, 2011.

(51) Int. Cl.
| | | |
|---|---|---|
| *C07K 14/765* | (2006.01) | |
| *A61K 38/38* | (2006.01) | |
| *C07K 14/55* | (2006.01) | |
| *C07K 14/755* | (2006.01) | |
| *C07K 16/18* | (2006.01) | |
| *C12N 9/64* | (2006.01) | |

(52) U.S. Cl.
CPC .......... *C07K 14/765* (2013.01); *A61K 38/385* (2013.01); *C07K 14/55* (2013.01); *C07K 14/755* (2013.01); *C07K 16/18* (2013.01); *C12N 9/6437* (2013.01); *C07K 2319/31* (2013.01)

(58) Field of Classification Search
None
See application file for complete search history.

(56) References Cited

U.S. PATENT DOCUMENTS

| | | |
|---|---|---|
| 2,714,586 A | 8/1955 | Lynch et al. |
| 4,302,386 A | 11/1981 | Stevens |
| 4,741,900 A | 5/1988 | Alvarez et al. |
| 4,757,006 A | 7/1988 | Toole, Jr. et al. |
| 4,784,950 A | 11/1988 | Hagen et al. |
| 4,795,805 A | 1/1989 | Itoh et al. |
| 4,868,112 A | 9/1989 | Toole, Jr. |
| 5,073,627 A | 12/1991 | Curtis et al. |
| 5,208,020 A | 5/1993 | Chari et al. |
| 5,223,409 A | 6/1993 | Ladner et al. |
| 5,264,586 A | 11/1993 | Nicolaou et al. |
| 5,294,699 A | 3/1994 | Ohmura et al. |
| 5,380,712 A | 1/1995 | Ballance et al. |
| 5,625,041 A | 4/1997 | Johnson et al. |
| 5,698,426 A | 12/1997 | Huse |
| 5,712,374 A | 1/1998 | Kuntsmann et al. |
| 5,714,377 A | 2/1998 | Tanner et al. |
| 5,714,586 A | 2/1998 | Kunstmann et al. |
| 5,716,808 A | 2/1998 | Raymond |
| 5,728,553 A | 3/1998 | Goodey et al. |
| 5,736,383 A | 4/1998 | Raymond |
| 5,766,883 A | 6/1998 | Ballance et al. |
| 5,773,001 A | 6/1998 | Hamann et al. |
| 5,824,837 A | 10/1998 | Chen et al. |
| 5,854,039 A | 12/1998 | Raymond et al. |
| 5,876,969 A | 3/1999 | Fleer et al. |
| 5,888,768 A | 3/1999 | Raymond |
| 5,948,609 A | 9/1999 | Carter et al. |
| 6,509,313 B1 | 1/2003 | Smith |
| 6,599,873 B1 | 7/2003 | Sommer et al. |
| 6,686,179 B2 | 2/2004 | Fleer et al. |
| 6,905,688 B2 | 6/2005 | Rosen et al. |
| 6,926,898 B2 | 8/2005 | Rosen et al. |
| 6,949,691 B2 | 9/2005 | Carter |
| 6,972,322 B2 | 12/2005 | Fleer et al. |
| 6,987,006 B2 | 1/2006 | Fleer et al. |

(Continued)

FOREIGN PATENT DOCUMENTS

| | | |
|---|---|---|
| CA | 2611540 | 5/2009 |
| CA | 2562249 | 4/2016 |

(Continued)

OTHER PUBLICATIONS van Dongen et al. (Immuno-PET: A Navigator in Monoclonal Antibody Development and Applications; The Oncologist Cancer Imaging 2007; 12: 1379-1389).*

(Continued)

*Primary Examiner* — James H Alstrum-Acevedo
*Assistant Examiner* — Tara L Martinez
(74) *Attorney, Agent, or Firm* — Knobbe, Martens, Olson & Bear LLP

(57) ABSTRACT

The invention provides methods and materials for making and using variant serum albumin amino acid sequences which exhibit improved properties compared to wild type serum albumin sequences. The invention further provides methods and materials for making and using fusion proteins in which the variant serum albumin amino acid sequences are fused to a therapeutic or diagnostic agent, such as a therapeutic protein, or a functional fragment or variant thereof that maintains activity, and exhibits improved properties.

33 Claims, 10 Drawing Sheets

Specification includes a Sequence Listing.

(56) References Cited

U.S. PATENT DOCUMENTS

| | | | |
|---|---|---|---|
| 6,989,365 B2 | 1/2006 | Fleer et al. |
| 6,994,857 B2 | 2/2006 | Rosen et al. |
| 7,041,478 B2 | 5/2006 | Fleer et al. |
| 7,041,802 B2 | 5/2006 | Young et al. |
| 7,041,803 B2 | 5/2006 | Ni et al. |
| 7,045,318 B2 | 5/2006 | Ballance |
| 7,053,190 B2 | 5/2006 | Ruben et al. |
| 7,056,701 B2 | 6/2006 | Fleer et al. |
| 7,081,354 B2 | 7/2006 | Fleer et al. |
| 7,094,577 B2 | 8/2006 | Fleer et al. |
| 7,141,547 B2 | 11/2006 | Rosen et al. |
| 7,196,164 B2 | 3/2007 | Rosen et al. |
| 7,253,259 B2 | 8/2007 | Otagiri et al. |
| 7,271,149 B2 | 9/2007 | Glaesner et al. |
| 7,358,416 B2 | 4/2008 | Roopenian |
| 7,410,779 B2 | 8/2008 | Fleer et al. |
| 7,425,622 B2 | 9/2008 | Rosen |
| 7,435,410 B2 | 10/2008 | Fleer et al. |
| 7,465,707 B2 | 12/2008 | Ni et al. |
| 7,482,013 B2 | 1/2009 | Ballance et al. |
| 7,507,413 B2 | 3/2009 | Rosen et al. |
| 7,507,414 B2 | 3/2009 | Rosen et al. |
| 7,514,079 B2 | 4/2009 | Rosen et al. |
| 7,550,432 B2 | 6/2009 | Ballance |
| 7,569,215 B2 | 8/2009 | Wittrup et al. |
| 7,572,619 B2 | 8/2009 | Hauser et al. |
| 7,592,010 B2 | 9/2009 | Rosen et al. |
| 7,597,886 B2 | 10/2009 | Yu et al. |
| 7,615,537 B2 | 11/2009 | Scaria et al. |
| 7,785,599 B2 | 8/2010 | Ballance et al. |
| 7,833,521 B2 | 11/2010 | Fleer et al. |
| 7,850,963 B2 | 12/2010 | Rosen et al. |
| 7,851,596 B2 | 12/2010 | Gentz et al. |
| 7,862,818 B2 | 1/2011 | Raschke et al. |
| 7,951,360 B2 | 5/2011 | Wittrup et al. |
| 7,998,691 B2 | 8/2011 | Kulaksiz et al. |
| 8,012,464 B2 | 9/2011 | Rosen et al. |
| 8,080,651 B2 | 12/2011 | Goldberg |
| 8,541,378 B2 | 9/2013 | Ahn et al. |
| 8,697,650 B2 * | 4/2014 | Gao ............... C07K 14/765 514/15.2 |
| 8,748,380 B2 | 6/2014 | Plumridge et al. |
| 8,822,417 B2 | 9/2014 | Andersen et al. |
| 9,493,545 B2 | 11/2016 | Finnis et al. |
| 9,944,691 B2 | 4/2018 | Delahay |
| 10,208,102 B2 | 2/2019 | Andersen et al. |
| 10,233,228 B2 | 3/2019 | Plumridge et al. |
| 10,329,340 B2 | 6/2019 | Delahay |
| 2002/0123080 A1 | 9/2002 | Sonnenschein et al. |
| 2002/0151011 A1 | 10/2002 | Fleer et al. |
| 2003/0091565 A1 | 5/2003 | Beltzer et al. |
| 2003/0104578 A1 | 6/2003 | Ballance |
| 2004/0063635 A1 | 4/2004 | Yu |
| 2004/0171154 A1 | 9/2004 | Storici et al. |
| 2005/0142106 A1 | 6/2005 | Wittrup et al. |
| 2005/0222026 A1 | 10/2005 | Otagiri |
| 2005/0256303 A1 | 11/2005 | Otagiri et al. |
| 2006/0018859 A1 | 1/2006 | Carter |
| 2006/0051859 A1 | 3/2006 | Fu |
| 2006/0171892 A1 | 8/2006 | Woodrow |
| 2006/0178301 A1 | 8/2006 | Jurs |
| 2007/0041987 A1 | 2/2007 | Carter et al. |
| 2007/0092940 A1 | 4/2007 | Eigenbrot |
| 2008/0108560 A1 | 5/2008 | Beals et al. |
| 2008/0167238 A1 | 7/2008 | Rosen et al. |
| 2009/0029914 A1 | 1/2009 | Rosen et al. |
| 2010/0129846 A1 | 5/2010 | Goldknopf |
| 2011/0091412 A1 | 4/2011 | Wittrup et al. |
| 2011/0151490 A1 | 6/2011 | Hillman |
| 2011/0172398 A1 | 7/2011 | Borges et al. |
| 2011/0313133 A1 | 12/2011 | Finnis |
| 2012/0220530 A1 | 8/2012 | Plumridge et al. |
| 2012/0322739 A1 | 12/2012 | Andersen et al. |
| 2013/0028930 A1 | 1/2013 | Plumridge |
| 2013/0053322 A1 | 2/2013 | Gao |
| 2013/0225496 A1 | 8/2013 | Plumridge |
| 2014/0128326 A1 | 5/2014 | Cameron |
| 2014/0148392 A1 | 5/2014 | Gao et al. |
| 2014/0234311 A1 | 8/2014 | Sleep et al. |
| 2014/0248682 A1 | 9/2014 | Gao et al. |
| 2014/0315816 A1 | 10/2014 | Andersen et al. |
| 2014/0315817 A1 | 10/2014 | Schmidt et al. |
| 2015/0210752 A1 | 7/2015 | Cameron |
| 2016/0009787 A1 | 1/2016 | Sleep et al. |
| 2016/0005299 A1 | 2/2016 | Schmidt et al. |
| 2016/0033523 A1 | 2/2016 | Cameron et al. |
| 2016/0075756 A1 | 3/2016 | Sleep et al. |
| 2016/0075757 A1 | 3/2016 | Sleep et al. |
| 2016/0075758 A1 | 3/2016 | Sleep et al. |
| 2016/0075759 A1 | 3/2016 | Sleep et al. |
| 2016/0075760 A1 | 3/2016 | Sleep et al. |
| 2016/0075761 A1 | 3/2016 | Sleep et al. |
| 2016/0075762 A1 | 3/2016 | Sleep et al. |
| 2016/0075763 A1 | 3/2016 | Sleep et al. |
| 2017/0081389 A1 | 3/2017 | Finnis et al. |
| 2018/0072792 A1 | 3/2018 | Sleep et al. |
| 2018/0105576 A1 | 4/2018 | Sleep et al. |
| 2018/0105577 A1 | 4/2018 | Sleep et al. |
| 2018/0105578 A1 | 4/2018 | Sleep et al. |
| 2018/0162925 A1 | 6/2018 | Sleep et al. |
| 2018/0222963 A1 | 8/2018 | Sleep et al. |
| 2018/0265568 A1 | 9/2018 | Delahay et al. |
| 2018/0265569 A1 | 9/2018 | Delahay |
| 2018/0265570 A1 | 9/2018 | Sleep et al. |
| 2019/0113519 A1 | 4/2019 | Cameron et al. |
| 2019/0315836 A1 | 10/2019 | Delahay et al. |

FOREIGN PATENT DOCUMENTS

| | | |
|---|---|---|
| CN | 1405182 | 3/2003 |
| CN | 101875693 B | 7/2012 |
| EP | 0286424 | 10/1988 |
| EP | 0319067 | 6/1989 |
| EP | 0413622 | 2/1991 |
| EP | 0438102 | 7/1991 |
| EP | 0464590 | 1/1992 |
| EP | 0510693 | 4/1992 |
| EP | 0305216 | 8/1995 |
| EP | 1681304 | 7/2006 |
| JP | 2005-206577 | 8/2005 |
| JP | 4983148 | 7/2012 |
| KR | 2005-0075134 | 7/2005 |
| RU | 2369404 | 10/2009 |
| WO | WO 1990/13653 | 11/1990 |
| WO | WO 1991/09125 | 6/1991 |
| WO | WO 1992/04367 | 3/1992 |
| WO | WO 1992/06204 | 4/1992 |
| WO | WO 1993/21232 | 10/1993 |
| WO | WO 1994/04687 | 3/1994 |
| WO | WO 1994/11026 | 5/1994 |
| WO | WO 1995/17413 | 6/1995 |
| WO | WO 1995/22625 | 8/1995 |
| WO | WO 1995/23857 | 9/1995 |
| WO | WO 1995/24427 | 9/1995 |
| WO | WO 1997/24445 | 7/1997 |
| WO | WO 1999/28348 | 6/1999 |
| WO | WO 2000/008207 | 2/2000 |
| WO | WO 2000/044772 | 8/2000 |
| WO | WO 2000/069902 | 11/2000 |
| WO | WO 2001/079258 | 10/2001 |
| WO | WO 2001/079271 | 10/2001 |
| WO | WO 2001/079442 | 10/2001 |
| WO | WO 2001/079443 | 10/2001 |
| WO | WO 2001/079444 | 10/2001 |
| WO | WO 2001/079480 | 10/2001 |
| WO | WO 2002/022809 | 3/2002 |
| WO | WO 2002/043658 | 6/2002 |
| WO | WO 2002/083897 | 10/2002 |
| WO | WO 2002/102830 | 12/2002 |
| WO | WO 2003/059934 | 7/2003 |
| WO | WO 2003/060071 | 7/2003 |
| WO | WO 2003/066085 | 8/2003 |
| WO | WO 2003/066824 | 8/2003 |
| WO | WO 2004/101620 | 1/2004 |

(56) References Cited

FOREIGN PATENT DOCUMENTS

| | | |
|---|---|---|
| WO | WO 2004/011499 | 2/2004 |
| WO | WO 2004/071536 | 8/2004 |
| WO | WO 2004/082640 | 9/2004 |
| WO | WO 2004/083245 | 9/2004 |
| WO | WO 2005/003296 | 1/2005 |
| WO | WO 2005/061718 | 7/2005 |
| WO | WO 2005/061719 | 7/2005 |
| WO | WO 2005/077042 | 8/2005 |
| WO | WO 2005/082423 | 9/2005 |
| WO | WO 2006/066595 | 6/2006 |
| WO | WO 2006/067511 | 6/2006 |
| WO | WO 2006/073195 | 7/2006 |
| WO | WO 2006/118772 | 11/2006 |
| WO | WO 2006/136831 | 12/2006 |
| WO | WO 2007/021494 | 2/2007 |
| WO | WO 2007/071068 | 6/2007 |
| WO | WO 2007/090584 | 8/2007 |
| WO | WO 2007/112940 | 10/2007 |
| WO | WO 2007/144173 | 12/2007 |
| WO | WO 2007/146038 | 12/2007 |
| WO | WO 2008/007146 | 1/2008 |
| WO | WO 2008/030558 | 3/2008 |
| WO | WO 2009/019314 | 2/2009 |
| WO | WO 2009/081201 | 7/2009 |
| WO | WO 2009/126920 | 10/2009 |
| WO | WO 2009/134808 | 11/2009 |
| WO | WO 2010/059315 | 5/2010 |
| WO | WO 2010/065950 | 6/2010 |
| WO | WO 2010/068278 | 6/2010 |
| WO | WO 2010/092135 | 8/2010 |
| WO | WO 2010/118169 | 10/2010 |
| WO | WO 2010/129023 | 11/2010 |
| WO | WO 2010/138814 | 12/2010 |
| WO | WO 2010/141329 | 12/2010 |
| WO | WO 2011/011315 | 1/2011 |
| WO | WO 2011/011797 | 1/2011 |
| WO | WO 2011/018611 | 2/2011 |
| WO | WO 2011/044563 | 4/2011 |
| WO | WO 2011/051489 | 5/2011 |
| WO | WO 2011/079175 | 6/2011 |
| WO | WO 2011/103076 | 8/2011 |
| WO | WO 2011/124718 | 10/2011 |
| WO | WO 2011/146902 | 11/2011 |
| WO | WO 2011/161127 | 12/2011 |
| WO | WO 2012/020143 | 2/2012 |
| WO | WO 2012/059486 | 5/2012 |
| WO | WO 2012/112188 | 8/2012 |
| WO | WO 2012/150319 | 11/2012 |
| WO | WO 2013/010840 | 1/2013 |
| WO | WO 2013/075066 | 5/2013 |
| WO | WO 2013/135896 | 9/2013 |
| WO | WO 2014/005596 | 1/2014 |
| WO | WO 2014/072481 | 5/2014 |
| WO | WO 2014/179657 | 11/2014 |
| WO | WO 2015/036579 | 3/2015 |

OTHER PUBLICATIONS

Andersen et al., 2006, The conserved histidine 166 residue of the human neonatal Fc receptor heavy chain is critical for the pH-dependent binding to albumin, Eur J Immunol, 36:3044-3051.
Andersen et al., 2007, A receptor-mediated mechanism to support clinical observation of altered albumin variants, Clinic Chem, 53(12):2216.
Andersen et al., 2008, Ligand binding and antigenic properties of a human neonatal Fc receptor with mutation of two unpaired cysteine residues, FEBS Journal, 275(16):4097-4110.
Andersen et al., 2009, The versatile MCH class I-related FcRn protects IgG and albumin from degradation: implications for development of new diagnostics and therapeutics, Drug Metab Pharmacokinet, 24(4):318-332.
Andersen et al., 2010, Cross-species binding analyses of mouse and human neonatal Fc receptor show dramatic differences in immunoglobulin G and albumin binding. J Biol Chem. 285(7):4826-4836.
Andersen et al., 2010, FcRn binding properties of an abnormal truncated analbuminemic albumin variant, Clinical Biochem, 43:367-372.
Andersen et al., 2012, Structure-based mutagenesis reveals the albumin-binding site of the neonatal Fc receptor, Nature Comm. 3:610 and supplemental information.
Andersen et al., Aug. 16, 2013, Single-chain variable fragment albumin fusions bind the neonatal Fc receptor (FcRn) in a species-dependent manner: implications for in vivo half-life evaluation of albumin fusion therapeutics, J Biol Chem., 288(33):24277-24285.
Andersen et al., May 2014, Extending serum half-life of albumin by engineering neonatal Fc receptor (FcRn) binding, J Biol Chem., 289(19):13492-502.
Anderson et al., 2006, Perspective—FcRn transports albumin: relevance to immunology and medicine, Trends Immunol, 27(7):343-348.
Balan et al., 2006, A phase I/II study evaluating escalating doses of recombinant human albumin-interferon-α fusion protein in chronic hepatitis C patients who have failed previous interferon-α-based therapy, Antiviral Therapy, 11(1):35-45.
Ballesta-Claver et al., 2011, Disposable luminol copolymer-based biosensor for uric acid in urine, Analytica Chimica Acta, 702:254-261.
Barash et al., 1993, Synthesis and secretion of human serum albumin by mammary gland explants of virgin and lactating transgenic mice, Trans Res, 2:266-276.
Bar-Or et al., 2006, The formation and rapid clearance of a truncated albumin species in a critically ill patient, Clin Chim Acta 365(1-2):346-349.
Barr et al., 1996, C-Type Natriuretic Peptide, Peptides 17(7):1243-1251.
Benotti et al., 1979, Protein and caloric or macronutrient metabolic management of the critically ill patient, Crit Care Med, 7(12):520-525.
Bergmann et al., Jun. 2012, Development of a mathematical model for neonatal Rc receptor recycling to design human serum albumin mutants with extended half-lives, Medimmune FcRn recycling model for mutant albumins, poster, $21^{st}$ PAGE meeting, Venice Italy, 1 p.
Berntzen et al., 2005, Prolonged and increased expression of soluble Fc receptors, IgG and a TCR-Ig fusion protein by transiently transfected adherent 293E cells, J Immun Method. 298:93-104.
Bhattacharya et al., 2000, Binding of the general anesthetics propofol and halothane to human serum albumin. High resolution crystal structures, J Biol Chem. 275(49):38731-38738.
Bhattacharya et al., 2000, Crystallographic analysis reveals common modes of binding of medium and long-chain fatty acids to human serum albumin, J. Mol. Biol., 303:721-732.
Blackburn, 2007, Maternal, Fetal and Neonatal Physiology: A Clinical Perspective, 3rd ed., pp. 197-198.
Bosse et al., 2005, Phase I comparability of recombinant human albumin and human serum albumin, J Clin Pharmacol, 35:57-67.
Bowe et al., 2001, FGF-23 inhibits renal tubular phosphate transport and is a PHEX substrate, Biochem Biophys Res Commun., 284:977-981.
Brennan et al., 2000, Three truncated forms of serum albumin associated with pancreatic pseudocyst, Biochim Biophys Acta 1481(2):337-343.
Broze et al., Feb. 25, 1980, Purification and properties of human coagulation factor VII, J Biol Chem., 255(4):1242-1247.
Bunting et al., 2012, Enhanced albumins and albumin fusion technology: tuning circulatory half-life with Novozymes Albufuse® Flex to meet medical needs, Poster, Biopharma NZ, 1 p.
Burmeister et al., 1994, Crystal structure at 2.2 Å result ion of the MHC-related neonatal Fc receptor, Nature, 372(6504):336-343.
Burmeister et al., 1994, Crystal structure of the complex of rat neonatal Fc receptor with Fc, Nature, 372(6504):379-383.
Cai et al., Jun. 2010, QPSOBT: One codon usage optimization software for protein heterologous expression, J Bioinformatics Sequence Analysis, 2(2):25-29.
Cantor et al. [Eds], 1980, Box 21-2. Reoxidation and refolding of reduced proteins, in *Biophysical chemistry. Part III: The behavior of biological macromolecules*, W.H. Freeman & Co., p. 1104.

(56) References Cited

OTHER PUBLICATIONS

Carlson et al., 1992, Alloalbuminemia in Sweden: structural study and phenotypic distribution of nine albumin variants, PNAS USA 89:8225-8229.
Carter et al., 1989, Three-dimensional structure of human serum albumin, Science, 244(4909):1195-1198.
Chari et al., 1992, Immunoconjugates Containing Novel Maytansinoids: Promising Anticancer Drugs; Cancer Research 52:127-131.
Chaudhury et al., 2003, The major histocompatibility complex-related Fc receptor for IgG (Fern) binds albumin and prolongs its lifespan, J Exp Med, 197(3):315-322.
Chaudhury et al., 2006, Albumin binding to FcRn: distinct from the FcRn-IgG interaction, Biochem. 45:4983-4990 and Supplemental Material in 4 pages.
Chen et al., 2003, ZDOCK: an initial-stage protein-docking algorithm, Protein, 52:80-87.
Condreay et al., 2007, Baculovirus Expression Vectors for Insect and Mammalian Cells, Current Drug Targets, 8:1126-1131.
Cornell et al., 1981, The environment of the sulfhydryl group in human plasma albumin as determined by spin labelling, Arch Biochem Biophys, 209(1):1-6.
Curry et al., 1998, Crystal structure of human serum albumin complexed with fatty acid reveals on asymmetric distribution of binding sites, Nat Struct Biol, 5(9):827-835.
Dagnino et al., 2010, A novel frameshift deletion in the albumin gene causes analbuminemia in a young Turkish woman, Clinic Chimica Acta, 411:1711-1715.
Database NCBI—Access No. 1A06_A (Jun. 1998); pp. 4.
Database NCBI—Access No. AAC63407 (Oct. 1998).
Database NCBI—Access No. AAD09358 (Jan. 1999).
Database NCBI—Access No. AAHF01000013.1 (March 1007) Aspergillus fumigatus in 110 pages.
Database NCBI—Access No. AAL08579 (Sep. 2001).
Database NCBI—Access No. AAL56646 (Jan. 2002).
Database NCBI—Access No. AAM46104 (Jun. 2002).
Database NCBI—Access No. AAN17825.1 (Sep. 2002).
Database NCBI—Access No. AAQ20088 (May 2004).
Database NCBI—Access No. ACF10391 (Jul. 2008).
Database NCBI—Access No. AXS56687 (Jan. 2010) 2 pages.
Database NCBI—Access No. NP_001004887 (Feb. 2011).
Database NCBI—Access No. NP_001127106 (May 2011).
Database NCBI—Access No. P02768 (Apr. 2011).
Database NCBI—Access No. P02770 (May 2011).
Database NCBI—Access No. P07724 (May 2011).
Database NCBI—Access No. P21847 (Nov. 2010); Serum Albumin, 2 pages.
Database NCBI Access No. 103600—Albumin (2011).
Database NCBI—Access No. P21848 (May 2011).
Database NCBI—Access No. P35747 (May 2011).
Database NCBI—Access No. P83517 (May 2011).
Database NCBI—Access No. Q03156 (May 2011).
Database NCBI—Access No. Q6WDN9-1 (Nov. 2006).
Database NCBI—Access No. Q91274 (Aug. 2010).
Database NCBI—Access No. QXLE4 (May 2011).
Database NCBI—Access No. S59517 (Mar. 2000).
Database Swiss prot—Access No. P49822 (Jun. 2009).
Database Swissprot—Access No. O73860 (Jun. 2009).
Database Swissprot—Access No. P01012 (Jun. 2009).
Database Swissprot—Access No. P02768 (May 2009).
Database Swissprot—Access No. P02769 (Jun. 2009).
Database Swissprot—Access No. P08835 (May 2009).
Database Swissprot—Access No. P14639 (May 2009).
Database Swissprot—Access No. P19121 (Jun. 2009).
Database Swissprot—Access No. P49064 (May 2009).
Database Swissprot—Access No. P49065 (May 2009).
Database Swissprot—Access No. Q28522 (May 2009).
DeMarco et al., 2007, Schistosome albumin is of host, not parasite, origin, Int J Parasit., 37(11):2101-1208.

Dickinson et al., Oct. 1999, Bidirectional FcRn-dependent IgG transport in a polarized human intestinal epithelial cell line, J Clin Invest., 104(7):903-911.
Di Stefano et al., 2004, A novel method for coupling doxorubicin to lactosaminated human albumin by an acid sensitive hydrazone bond; synthesis, characterization and preliminary biological properties of the conjugate, Eur J Pharm Sci, 23:393-397.
Dockal et al., Oct. 1, 1999, The three recombinant domains of human serum albumin, J Biol Chem, 274(41):29303-29310.
Doronina et al., 2003, Development of potent monoclonal antibody auristatin conjugates for cancer therapy, Nat Biotechnol, 21:778-784.
Elble, 1992, A simple and efficient procedure for transformation of yeasts, Biotechniques 13(1):18-20.
Farran et al., 2002, Targeted expression of human serum albumin to potato tubers, Trans Res, 11:337-346.
Feng et al., 2011, Design, expression and characterization of a soluble single-chain functional human neonatal Fc receptor, Prot Expr Purific., 79:66-71.
Ferrara et al., 1999, Pathophysiologic mechanisms of acute graft-vs.-host disease, Biol Blood Marrow Transpl., 5:347-56.
Flanagan, 2009, Protein engineering reaches new frontiers: more detailed knowledge of structure and function drives field forward quickly, Gen Eng Biotech News, 29(12):1-4.
Fleer et al., Oct. 1991, Stable multicopy vestors for high-level secretion of recombinant human serum albumin by *Kluyveromyces* yeasts, Biotech, 9(10):968-975.
Francisco et al., Aug. 2003, cAC10-vcMMAE, an anti-CD30-monomethyl auristatin E conjugate with potent and selective antitumor activity, Blood, 102(4):1458-1465.
Fu et al., 2004, Fibroblast growth factor 19 increases metabolic rate and reverses dietary and leptin-deficient diabetes. Endocrinol., 145(6):2594-2603.
Galliano et al., 1986, Structural characterization of a chain termination mutant of human serum albumin, J Biol Chem., 261:4283-4287.
Galliano et al., 1993, Protein and DNA sequence analysis of a 'private' genetic variant: albumin ortonovo (Glu-505 → Lys), Biochim Biophys Acta, 1225(1)27-32.
Gao et al., 2004, UpGene: Application of a Web-Based DNA Codon Optimization Algorithm, Biotechnol Prog, 20:443-448.
Garnier et al., 1994, Scale-Up of the Adenovirus Expression System for the Production of Recombinant Protein in Human 293S Cells, Cytotechnology, 15:145-155.
Gibbs et al., Apr. 13, 2007, Evolutionary and biomedical insights from the Rhesus Macaque genome, Science, 316(5822):222-234.
Graf et al., 2000, Concerted Action of Multiple cis-Acting Sequences Is Required for Rev Dependence of Late Human Immunodeficiency Virus Type 1 Gene Expression, J Virol 74(22):10822-10826.
Grantham et al., 1980, Codon Frequencies in 119 Individual Genes Confirm Consistent Choices of Degenerate Bases According to Genome Type, Nuc. Acids Res. 8(9):1893-1912.
Grosjean et al., 1982, Preferential Codon Usage in Prokaryotic Genes; The Optimal Codon-Anticodon Interaction Energy and the Selective Codon Usage in Efficiently Expressed Genes, Gene, 18:199-209.
Gustafsson et al., 2004, Codon bias and heterologous protein expression, Trends in Biotechnol. 22(7):346-353.
Gutniak et al., 1992, Antidiabetogenic Effect of Glucagon-like Peptide-1 (7-36) amide in Normal Subjects and Patients with Diabetes Mellitus, N Engl J Med., 326:1316-1322.
Haas et al., 1996, Codon usage limitation in the expression of HIV-1 envelope glycoprotein, Curr. Biol. 6:315-324.
Hagen et al., 1986, Characterization of a cDNA coding for human factor VII, PNAS USA, 83:2412-2416.
Hall et al., 2012, Interspecies scaling in pharmacokinetics: a novel whole-body physiologically based modeling framework to discovery drug biodistribution mechanisms In Vivo, J Pharma Sci, 101:1221-1241.
Hallstrom et al., 2008, S-nitroso human serum albumin reduces ischaemia/reperfusion injury in the pig heart after unprotected warm ischaemia, Cardiovascular Res, 77:506-514.

(56) References Cited

OTHER PUBLICATIONS

Haspel et al., 1999, Effects of barbiturates on facilitative glucose transporters are pharmacologically specific and isoform selective, J Membr Biol, 169:45-53.
Hassan et al., Oct. 1997, All About Albumin, Review, Clin Chem 43(10):2014a-2015.
Hay et al., Apr. 9, 2009, ThioTransferrin: a recombinant human transferrin engineered for site specific drug conjugation and delivery, Oral Presentation, 5th Annual PEGS, Boston, MA, Novozymes; 22 pages.
Henrotte et al., 2004, Investigation of non-covalent interactions between paramagnetic complexes and human serum albumin by electrospray mass spectrometry, Rapid Comm Mass Spectro, 18:1919-1924.
Herzog et al., 1999, Long-term correction of canine hemophilia B by gene transfer of blood coagulation factor IX mediated by adena-associated viral vector, Nature Med., 5(1):56-63.
Hillier et al, Apr. 2007, Generation and annotation of the DNA sequences of human chromosomes 2 and 4, Nature, 434:724-731.
Hinman et al., 1993, Preparation and Characterization of Monoclonal Antibody Conjugates of the Calicheamicins: A Novel and Potent Family of Antitumor Antibiotics, Cancer Research 53:3336-3342.
Holm, 1986, Codon usage and gene expression, Nuc. Acids Res. 14(7):3075-3087.
Holt et al., 2003, Definition of a novel growth factor-dependent signal cascade for the suppression of bile acid biosynthesis, Genes Dev, 17:1581-1591.
Houghton et al., 1980, The complete amino acid sequence of human fibroblast interferon as deduced using synthetic oligodeoxyribonucleotide primers of reverse transcriptase, Nucleic Acids Res., 8(13):2885-2894.
Howard et al., 1989, Intracerebral Drug Delivery in Rats with Lesion-Induced Memory Deficits, J. Neurosurg. 71:105-112.
Ikemura, 1982, Correlation between the abundance of yeast transfer RNAs and the occurrence of the respective codons in protein genes. Differences in synonymous codon choice patterns of yeast and *Escherichia coli* with reference to the abundance of isoaccepting transfer RNAs, J Mol Biol. 158:573-597.
Ishima et al., 2007, S-nitrosylation of human variant albumin liprizzi (R410C) confers potent antibacterial and cytoprotective properties, J Pharma Exp Therapeutics, 320(3):969-977.
Ito et al., 1983, Transformation of intact yeast cells treated with alkali cations, J Bacteriol, 153(1):163-168.
Iwao et al., 2006, Oxidation of Arg-410 promotes the elimination of human serum albumin, Biochim Biophys Acta, 1764(4):743-749.
Iwao et al., 2007, Changes of net charge and α-helical content affect the pharmacokinetic properties of human serum albumin, Biochim Biophys Acta, 1774:1582-1590.
Iwao et al., 2009, Altered chain-length and glycosylation modify the pharmacokinetics of human serum albumin, Biochem Biophys Acta, 1794(4):634-641.
Jaye et al., 1983, Isolation of a human anti-haemophilic factor IX cDNA clone using a unique 52-base synthetic oligonucleotide probe deduced from the amino acid sequence of bovine factor IX, Nucleic Acids Res. 11(8):2325-2335.
Jerdeva et al., Comparison of FcRn- and pIgR-mediated transport in MOCK cells by fluorescence confocal microscopy. Traffic. Sep. 2010;11 (9):1205-20.
Kabsch et al., 1983, Dictionary of protein secondary structure: pattern recognition of hydrogen-bonded and geometrical features, Biopolymers, 22(12):2577-2637.
Kaneko et al., Jan. 2008, Subdomain IIIA of dog albumin contains a binding site similar to site II of human albumin, Drug Metabol Disp. 36:81-86.
Kenanova et al., 2005, Tailoring the pharmacokinetics and positron emission tomography imaging properties of anti-carcinoembryonic antigen single-chain Fv-Fc antibody fragments, Cancer Res, 65(2):622-631.

Kenanova et al., 2007, Radioiodinated versus radiometal-labeled anti-carcinoembryonic antigen single-chain Fv-Fc antibody fragments; optimal pharmacokinetics for therapy, Cancer Res, 67(2):718-726.
Kenanova et al., 2009, HAS domain III as a protein scaffold with defined serum pharmacokinetics, J Nucl Med, 50(Supp 2): 1582-Abstract in 1 page.
Kenanova et al., 2010, Tuning the serum persistence of human serum albumin domain III:diabody fusion proteins, Prot Eng Design Selec, 23(10):789-798.
Khan et al., 2002, Bilirubin binding properties of pigeon serum albumin and its comparison with human serum albumin, J Biol Macromol., 30(3-4):171-178.
Kharitonenkov et al., 2005, FGF-21 as a novel metabolic regulator, J Clin Invest., 115(6):1627-1635.
Kim et al., Mar. 2003, Development and characterization of a glucagon-like peptide 1-albumin conjugate: the ability to activate the glucagon-like peptide 1 receptor in vivo, Diabetes, 52:751-759.
Kobayashi et al., 1998, The development of recombinant human serum albumin, Thera Apheresis, 2:257-262.
Kragh-Hansen et al., 2002, Practical aspects of the ligand-binding and enzymatic properties of human serum albumin, Biol Pharm Bull, 25(6):695-704.
Kragh-Hansen et al., 2004, Structural analysis and fatty acid-binding properties of two Croatian variants of human serum albumin, Clinical Chimica Acta, 349(1-2):105-112.
Kragh-Hansen et al., 2005, Effect of genetic variation on the thermal stability of human serum albumin, Biochim Biophys Acta, 1747(1):81-88.
Kratz, 2008, Albumin as a drub carrier: design of prodrugs, drug conjugates and nanoparticles, J Controlled Release, 132(3):171-183.
Kuo et al., 2010, Neonatal Fc receptor: from immunity to therapeutics, J Clin Immunol, 30(6):777-789.
Kurtzhals et al., 1995, Albumin binding of insulins acylated with fatty acids; characterization of the ligand-protein interaction and correlation between binding affinity and timing of the insulin effect in vivo, Biochem J, 312:725-731.
Kurtzhals et al., 1997, Effect of fatty acids and selected drugs on the albumin binding of a long-acting, acylated insulin analogue, J Pharma Sci, 86:1365-1368.
Laftah et al., May 15, 2004, Effect of hepcidin on intestinal iron absorption in mice, Blood, 103(10):3940-3944.
Larsen et al., 2004, Use of the Gottingen minipig as a model of diabetes, with special focus on type 1 diabetes research ILAR Journal, 45(3):303-313.
Leger et al., 2004, Identification of CJC-1131-albumin bioconjugate as a stable and bioactive GLP-1(7-36) analog, Bioorg Med Chem Lttrs, 14(17):4395-4398.
Leger et al., 2003, Synthesis and in vitro analysis of atrial natriuretic peptide-albumin conjugates, Bioorganic Medical Chem Lttrs, 13:3571-3575.
Li et al., 2001, Bipartite regulation of different components of the MHC class 1 antigen-processing machinery during dendritic cell maturation, Intl Immunol, 13(12):1515-1523.
Liu et al., 2009, A high-yield and scaleable adenovirus vector production process based on high density perfusion culture of HEK 293 cells as suspended aggregates, J Bioscience Bioeng., 107(5):524-529.
Lode et al., Jul. 15, 1998, Targeted Therapy with a Novel Enediyene Antibiotic Calicheamicin theta11 Effectively Suppresses Growth and Dissemination of Liver Metastases in a Syngeneic Model of Murine Neuroblastoma, Cancer Research, 58:2925-2928.
Luckow et al., 1993, Efficient Generation of Infectious Recombinant Baculoviruses by Site-Specific Transposon-Mediated Insertion of Foreign Genes into a Baculovirus Genome Propagated in *Escherichia coli*, J. Virol. 67(8):4566-4579.
Mahmood, 2004, Chapter 7: Principles, issues and applications of interspecies scaling, in *New Drug Development*, Sahajwalla ed., Marcel Dekker, Inc., New York, pp. 137-163.
McClenaghan et al., Aug. 1996, Characterization of a novel glucose-responsive insulin-secreting cell line, BRIN-BD11, produced by electrofusion, Diabetes, 45:1132-1140.

(56) References Cited

OTHER PUBLICATIONS

McGregor, 2008, Discovering and improving novel peptide therapeutics, Curr Opin Pharmacol, 8(5):616-619.
Mezo et al., 2010, X-ray crystal structures of monomeric and dimeric peptide inhibitors in complex with the human neonatal Fc receptor, FcRn, J Biol Chem, 285(36):27694-27701.
Miguel et al., 2003, Cooperative enhancement of insulinotropic action of GLP-1 by acetylcholine uncovers paradoxical inhibitory effect of beta cell muscarinic receptor activation on adenylate cyclase activity Biochem Pharm., 65:283-292.
Minchiotti et al., 1987, Structure characterization of two genetic variants of human serum albumin, Biochim Biophys Acta, 916(3):411-418.
Minchiotti et al., 1990, The molecular defect of albumin Castel di Sangro: 536 Lys → Gllu, Biochem Bioph Acta, 1039:204-208.
Minchiotti et al., 2001, A nucleotide insertion and frameshift cause albumin Kenitra, an extended and O-glycosylated mutant of human serum albumin with two additional disulfide bridges, Eur J Biochem., 268:344-352.
Minchiotti et al., 2008, Mutations and polymorphisms of the gene of the major human blood protein, Serum albumin, Human Mutation 29(8):1007-1016.
Montoyo et al., 2009, Conditional deletion of the MHC class I-related receptor FcRn reveals the sites of IgG homeostasis in mice, Proc Natl Acad Sci USA, 106(8):2788-2793.
Morrissey et al., Feb. 1, 1993, Quantitation of activated factor VII levels in plasma using a tissue factor mutant selectively deficient in promoting factor VII activation, Blood, 81(3):734-744.
Müller et al., 2007, Improved pharmacokinetics of recombinant bispecific antibody molecules by fusion to human serum albumin, J Bio Chem., 282(17):12650-12660.
Nauck et al., 1993, Normalization of fasting hyperglycaemia by exogenous glucagon-like peptide 1 (7-36 amide) in type 2 (non-insulin-dependent) diabetic patients, Diabetologia 36:741-744.
Nauck et al., 1993, Preserved incretin activity of glucagon-like peptide 1 [7-36 amide] but not of synthetic human gastric inhibitory polypeptide in patients with type-2 diabetes mellitus. Clin Invest., 91:301-307.
Needleman et al., 1970, A general method applicable to the search for similarities in the amino acid sequence of two proteins. J Mol Biol., 48(3):443-453.
New Century Pharmaceuticals Inc., 2005 Catalog, Recombinant Serum Albumin: Other Proteins & Antibodies, pp. 1-36.
Ober et al., 2001, Differences in promiscuity for antibody—FcRn interactions across species: implications for therapeutic antibodies, Int Immunol 13(12):1551-1559.
Ober et al., 2004, Exocytosis of IgG as mediated by the receptor, FcRn: an analysis at the single-molecule level, PNAS USA, 101(30):11076-11081.
Ober et al., 2004, Visualizing the site and dynamics of IgG salvage by the MHC class I-related receptor, FcRn, J Immunol, 172(4):2021-2029.
Oganesyan et al., 2014, Structural insights into neonatal Fc receptor-based recycling mechanisms, J Biol Chem 289(11):7812-24.
O'Hara et al., 1987, Nucleotide sequence of the gene coding for human factor VII, a vitamin K-dependent protein participating in blood coagulation, PNAS USA, 84:5158-5162.
Olafsen et al., 2006, Tunable pharmacokinetics; modifying the in vivo half-life of antibodies by directed mutagenesis of the Fc fragment, Nature Protocol, 1(4):2048-2060.
O'Neill et al., 2008, Scale-up of *Agrobacterium*-mediated transient protein expression in bioreactor-grown *Nicotiana glutinosa* plant cell suspension culture, Biotechnol Prog., 24:372-376.
Osborn et al., 2002, Pharmacokinetic and pharmacodynamic studies of a human serum albumin-interferon-α fusion protein in cynomolgus monkeys, J Pharmacol Exp Ther, 303(2):540-548.
Otagiri et al., Apr. 2009, Pharmaceutically Important Pre- and Postransitional Modifications on Human Serum Albumin, Biol Pharm Bull., 32(4):527-534.

Peach et al., 1991, Structural characterization of glycoprotein variant of human serum albumin: albumin Casebrook (494 Asp → Asn), Biochim Biophys Acta, 1097:49-54.
Peters, 1985, Serum Albumin, Advances in Protein Chemistry, 37:161-245.
Peters [Ed], 1996, All about Albumin: Biochemistry, Genetics and Medical Applications, Academic Press, Cooperstown, NY, pp. 10, 170-181, 245-250 in 37 pages.
Pierce, Crosslinking Reagents Technical Handbook, Thermo Fisher Scientific, Rockford, IL, USA; downloaded Feb. 9, 2009 <https://tools.lifetechnologies.com/content/sfs/brochures/1602163-Crosslinking-Reagents>, 48 pp.
Pittman et al., 1993, Biochemical, immunological, and in vivo functional characterization of B-domain-deleted factor VIII, Blood, 81:2925-2935.
Prabhat et al., 2007, Elucidation of intracellular recycling pathways leading to exocytosis of the Fc receptor, FcRn, by using multifocal plane microscopy, Proc Natl Acad Sci USA, 104(14):5889-5894.
Rakestraw et al., 2009, Directed evolution of a secretory leader for the improved expression of heterologous proteins and full-length antibodies in *S. cerevisiae*, Biotech Bioengin. 103(6):1192-1201.
Rao et al., 2003, Interleukin-2 mutants with enhanced alpha-receptor subunit binding affinity, Protein Engin., 16(12):1081-1087.
Rao et al., 2005, High-affinity CD25-binding IL-2 mutants potently stimulate persistent T cell growth, Biochemistry 44:10696-10701.
Rice et al., 2000, EMBOSS: The European Molecular Biology Open Software Suite, Trends in Genetics, 16(6):276-277.
Riminucci et al., Sep. 2003, FGF-23 in fibrous dysplasia of bone and its relationship to renal phosphate wasting, J Clin Invest, 112(5):683-92.
Rinderknecht et al., Jun. 10, 1984, Natural Human Interferon-gamma. Complete amino acid sequence and determination of sites of glycosylation, J Biol Chem., 259(11):6790-6797.
Roopenian et al., 2003, The MHC class I-like IgG receptor controls perinatal IgG transport, IgG homeostasis, and fate of IgG-Fc-coupled drugs, J Immunol, 170(7):3528-3533.
Roopenian et al., 2007, FcRn: the neonatal Fc receptor comes of age, Nat Rev Immunol 7:715-725.
Roopenian et al., 2010, Human FcRn transgenic mice for pharmacokinetic evaluation of therapeutic antibodies, Methods Mol Biol, 602:93-104.
Sabater-Lleal et al., 2006, Human F7 sequence is split into three deep clades that are related to FVII plasma levels, Hum Genet 118:741-751.
Sandhu et al., 2008. GASCO: Genetic Algorithm Simulation for Codon Optimization. In Silico Biol. 8(2):187-192.
Sayle et al. Sep. 1995, RASMOL: biomolecular graphics for all, TIBS 20, 374-377.
Schmidt et al., 2013, Crystal Structure of an HAS/FcRn Complex Reveals Recycling by Competitive Mimicry of HSA Ligands at a pH-Dependent Hydrophobic Interface, Structure 21:1966-1978 and supplemental material.
Schulte, 2008, Use of albumin fusion technology to prolong the half-life of recombinant factor VIIa, Thromb Res. 122 Suppl. 4:S14-19.
Several (definition), dictionary.com, accessed on Oct. 30, 2015, 4 pp.
Sheffield et al., 2000, Modulation of clearance of recombinant serum albumin by either glycosylation or truncation, Thromb Res., 99(6):613-621.
Shimada et al., 2004, FGF-23 Is a Potent Regulator of Vitamin D Metabolism and Phosphate Homeostasis, J. Clin. Invest, 19(3):429-435.
Sijmons et al., 1990, Production of correctly processed human serum albumin in transgenic plants, Biotechnology (NY), 8(3):217-221.
Silveira et al., 1994, Activation of Coagulation Factor vii During Alimentary Lipemia, Arterioscler Thromb Vsc Biol., 14:60-69.
Simard et al., 2005, Locating high-affinity fatty acid-binding sites on albumin by x-ray crystallography and NMR spectroscopy, PNAS USA, 102(50):17958-17963.

(56) References Cited

OTHER PUBLICATIONS

Simard et al., 2006, Location of High and Low Affinity Fatty Acid Binding Sites on Human Serum Albumin Revealed by NMR Drug-competition Analysis, J Mol Biol., 361(2):336-351.
Sleep et al., 1990, the secretion of human serum albumin from the yeast *Saccharomyces cerevisiae* using five different leader sequences, Biotech.8:42-46.
Sleep et al., 1991, *Saccharomyces cerevisiae* strains that overexpress heterologous proteins, Biotechnology (NY) 9(2):183-187.
Sleep et al., 2001, Yeast 2 µ m plasmid copy number is elevated by a mutation in the nuclear gene UBC4, Yeast, 18(5):403-421.
Sleep, 2012, Produce Proteins with Tailored Circulatory Half Life to Meet Patients Specific Medical Needs, Keynote Address, Drug Delivery Partnerships. Las Vegas, NV. Jan. 25-27, 2012 in 29 pages.
Sorensen et al., 2004, Whole blood clot formation phenotypes in hemophilia a and rare coagulation disorders. Patterns of response to recombinant factor Vila, J Thromb Haemo. 2:102-110.
Spiekermann et al., 2002. Receptor-mediated Immunoglobulin G Transport Across Mucosal Barriers in Adult Life. J Exp Med. 196(3):303-10, and correction.
Stehle et al., 1997, Plasma protein (albumin) catabolism by the tumor itself—implications for tumor metabolism and the genesis of cachexia, Crit Rev Oncol Hematol, 26(2):77-100.
Stewart et al., 2003, Interdomain zinc site on human albumin, PNAS USA, 100(7):3701-3706.
Sugio et al., Jun. 1999, Crystal structure of human serum albumin at 2.5 Å resolution, Protein Eng. 12(6):439-446.
Suzuki et al., 2010, Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR, J Immunol. 184:1968-1976.
Sykes et al., 1994, Interleukin-2 inhibits graft-versus-host disease-promoting activity of CD4+ cells while preserving CD4− and CD8-mediated graft-versus-Leukemia effects, Blood, 83(9):2560-2569.
Takahashi et al., 1987, Amino acid substitutions in genetic variants of human serum albumin and in sequences inferred from molecular cloning, PNAS USA 84:4413-4417.
Tesar et al., 2006. Ligand valency affects transcytosis, recycling and intracellular trafficking mediated by the neonatal Fc receptor. Traffic. 7(9):1127-1142.
Thibaudeau et al., 2005, Synthesis and evaluation of insulin—human serum albumin conjugates, Bioconjug Chem., 16(4):1000-1008.
Thim et al., 1988, Amino acid sequence and posttranslational modifications of human factor Vila from plasma and transfected baby hamster kidney cells, Biochemistry, 27:7785-7793.
Toole et al., 1984, Molecular cloning of a cDNA encoding human antihaemophilic factor. Nature, 312:342-347.
Tsakiridis et al., 1995, Multiple roles of phosphatidylinositol 3-kinase in regulation of glucose transport, amino acid transport, and glucose transporters in L6 skeletal muscle cells, Endocrinol. 136(10):4315-4322.
Ueda et al., 2009, Chemoenzymatic Synthesis of Glycosylated Glucagon-like Peptide 1: Effect of Glycosylation on Proteolytic Resistance and in Vivo Blood Glucose-Lowering Activity, JACS Articles, 131:6237-6245.
Uniprot Database Accession No F7HCHO, Jul. 27, 2011, 2 pp.
UniProt Database Accession No. A6NBZ8 (A6NBZ8_HUMAN), Version 24, modified Mar. 8, 2011, accessed at http://www.uniprot.org/uniprot/A6NBZ8 on Mar. 23, 2011.
Urso et al., 1999, Differences in signaling properties of the cytoplasmic domains of the insulin receptor and insulin-like growth factor receptor in 3T3-L 1 adipocytes, J Biol Chem, 274(43):30864-30873.
van Deijk et al., 1983, Evaluation of a Coagulation Assay Determining the Activity State of Factor VII in Plasma, Haemostasis 13:192-197.
van der Spoel et al., 2005, GROMACS: Fast, flexible, and free, J Comp Chem, 22:1701-1718.
Vestberg et al., 1992, High-affinity binding of warfarin, salicylate and diazepam to natural mutants of human serum albumin modified in the c-terminal end, Biochem Pharmacol, 44(8):1515-1521.
Wain-Hobson et al. 1981, Preferential codon usage in genes, Gene 13:355-364.
Wang et al., 1997, Regulation of glucose transporters and hexose uptake in 3T3-L 1 adipocytes: glucagon-like peptide-1 and insulin interactions, J Mol Endocrinol, 19:241-248.
Wang et al., 2008, Overexpression of fibroblast growth factor 23 suppresses osteoblast differentiation and matrix mineralization in vitro. J Bone Miner Res. 23(6):939-948.
Wani et al., 2006, Familial hypercatabolic hypoproteinemia caused by deficiency of the neonatal Fc receptor, FcRn, due to a mutant β2-microglobulin gene, Proc Natl Acad Sci USA 103(13):5084-5089 and Correction/Retraction in 2 pages.
Ward et al., 2009, Multitasking by exploitation of intracellular transport functions: the many faces of FcRn, Adv Immunol 103:77-115.
Watkins et al., Mar. 1993, A donor splice mutation and a single-base deletion produce two carboxy-terminal variants of human serum albumin, PNAS USA, 88:5959-5963.
Watkins et al., Mar. 1993, cDNA and protein sequence of polymorphic macaque albumins that differ in bilirubin binding, PNAS USA, 90:2409-2413.
Werle et al., 2006, Strategies to improve plasma half life time of peptide and protein drugs, Amino Acids, 30(4):351-367.
West et al., 2000, Crystal structure and immunoglobulin G binding properties of the human major histocompatibility complex-related Fc receptor, Biochemistry 39(32):9698-9708.
Wildgoose et al., 1992, Measurement of basal levels of factor Vila in hemophilia A and B patients, Blood, 80:25-28.
Wood et al., 1984, Expression of active human factor VIII from recombinant DNA clones, Nature 312:330-337.
Wu et al., 1987, Receptor-mediated in vitro gene transformation by a soluble DNA carrier system, J Biol Chem., 262(10):4429-4432.
Wu et al., Dec. 1989, Urate Oxidase: Primary Structure and Evolutionary Implications, PNAS USA, 86:9412-9416.
Wunder et al., 2003, Albumin-based drug delivery as novel therapeutic approach for rheumatoid arthritis, J Immunol. 170:4793-4801.
Yoshida et al., 2004, Human neonatal Fc receptor mediates transport of IgG into luminal secretions for delivery of antigens to mucosal dendritic cells Immunity. 20(6):769-83.
Zalevsky et al., Feb. 2010, Enhanced antibody half-life improves in vivo activity, Nature Biotechnology, 28(2):157-159.
Zheng et al., 2012, Minipig as a potential translatable model for monoclonal antibody pharmacokinetics after intravenous and subcutaneous administration, mAbs, 4(2):243-255.
Zhu et al., 2005, Calnexin and ERp57 facilitate the assembly of the neonatal Fc receptor for IgG with beta 2-microglobulin in the endoplasmic reticulum. J Immunol., 175(2):967-76.
Zhu et al., 2001, MHC class 1-related neonatal Fc receptor for IgG is functionally expressed in monocytes, intestinal macrophages, and dendritic cells, J Immunol., 166(5):3266-76.
International Search Report and Written Opinion of International Application No. PCT/US2012/065733, dated May 21, 2013.
International Search Report of PCT/US2014/036508 dated Oct. 9,2014.
Written Opinion of the International Searching Authority for PCT/US2014/036508 dated Oct. 9, 2014.
International Search Report, International Patent Application No. PCT/IB2014/003002, dated Aug. 12, 2015.
Adams et al., 2013. The Adaptable Major Histocompatibility Complex (MHC) Fold: Structure and Function of Nonclassical and MHC Class 1-Like Molecules. Annu Rev Immunol. 31:529-561.
Akilesh et al., 2007. Neonatal FcR expression in bone marrow-derived cells functions to protect serum IgG from catabolism. J Immunol. (Baltimore, MD.: 1950) 179:4580-4588.
Allan et al "Enhanced albumins and albumin fusion technology"May 4, 2012 XP055109701 Retrieved from the Internet: URL:http:\\www.

(56) References Cited

OTHER PUBLICATIONS biopharma.novozymes.com/en/information-centre/posters-and-presentations/Documents/PEGS%20poster%202012_EZAL.pdf.
Altschul et al., 1997, Gapped Blast and Psi-Blast: A new generation of protein database search programs. Nucleic Acids Res. 25(17):3389-3402.
Amthor et al., 2004, Albumin targeting of damaged muscle fibres in the mdx mouse can be monitored by MRI. Neuromuscular Disorders 14(12): 791-796.
Averyhart-Fullard et al., 1990. Cloning and Thyroid Hormone Regulation of Albumin mRNA in *Rana catesbeiana* Tadpole Liver, Mol Endocrinol. 4(10):1556-1563.
Barton et al., 1990, Site-directed, recombination-mediated mutagenesis of a complex gene locus. Nucleic Acids Res. 18(24):7349-4955.
Basle, Mar. 26, 2010, Protein chemical modification on endogenous amino acids, Chemistry & Biology, 17:213-227.
Beeken et al., 1962. Studies of $I^{131}$-albumin catabolism and distribution in normal young male adults. The Journal of clinical investigation 41, 1312-1333.
Bennhold et al., 1959. Comparative studies on the half-life of I131-labeled albumins and nonradioactive human serum albumin in a case of analbuminemia. J Clin Invest. 38:863-872.
Boder et al., 1997. Yeast surface display for screening combinatorial polypeptide libraries. Nat Biotechnol. 15(6):553-557.
Boder et al., 2000. Directed evolution of antibody fragments with monovalent femtomolar antigen-binding affinity. PNAS U.S.A. 97:10701-10705.
Bos et al. 1989. The molecular mechanism of the neutral-to-base transition of human serum albumin. J Biol Chem. 264:953-959.
Bowie et al., 1989, Identifying determinants of folding and activity for a protein of unknown structure. PNAS U.S.A. 86(7):2152-2156.
Calissano et al., 1996, In vivo site-directed mutagenesis of Neurospora crassa beta-tubulin gene by spheroplasts transformation with oligonucleotides. Fungal Genetics Reports 43(Article 5) pp. 5.
CAPlus accession No. 2005:1283404, "Standard Albumin Gene . . . ", STN entry date Dec. 8, 2005; 1 page.
Chao et al. 2006. Isolating and engineering human antibodies using yeast surface display. Nature protocols 1(2):755-768.
Chapman A.P., 2002, PEGylated antibodies and antibody fragments for improved therapy: A review. Adv. Drug Deliv. Rev. 54:531-545.
Chen et al., 2013, Human serum albumin from recombinant DNA technology: challenges and strategies, Biochimica et Biophysica Acta, 1830:5515-5525.
Crystal Structure of Human Serum Albumin AT 2.5 A Resolution, PDB Accession: 1A06. publically available in 1999, 125 pp.
Curry, S., 2009. Lessons from the crystallographic analysis of small molecule binding to human serum albumin. Drug Metab Pharmacokinet. 24(4):342-357.
Dall'Acqua et al., 2002. Increasing the affinity of a human IgG1 for the neonatal Fc receptor: Biological consequences. J Immunol. 169:5171-5180.
Daniels et al., 2006, The transferrin receptor part II: Targeted delivery of therapeutic agents into cancer cells. Clin Immunol. 121(2):159-176.
Database EMBL accession No. BAG37325; Jan. 12, 2008, "*Homo sapiens* hypothetical protein", 2 pages.
Datta-Mannan et al., 2007. Monoclonal antibody clearance: Impact of modulating the interaction of IgG with the neonatal Fc receptor. J Biol Chem. 282(3):1709-1717.
Datta-Mannan et al. 2012. FcRn affinity-pharmacokinetic relationship of five human IgG4 antibodies engineered for improved in vitro FcRn binding properties in cynomolgus monkeys. Drug Metabol Dispos. 40(8):1545-1555.
Debinski W., 2002, Local treatment of brain tumors with targeted chimera cytotoxic proteins. Cancer Invest. 20(5):801-809.
Derbyshire et al., 1986, A simple and efficient procedure for saturation mutagenesis using mixed oligodeoxynucleotides. Gene 46(2-3):145-152.
Dugaiczyk et al, Jan. 1982, Nucleotide sequence and the encoded amino acids of human serum albumin mRNA, PNAS, USA, 79:71-75.
Edgar R.C. 2004, MUSCLE: multiple sequence alignment with high accuracy and high throughput. Nucleic Acids Res. 32(5):1792-1797.
Edgar R.C., 2004, MUSCLE: a multiple sequence alignment method with reduced time and space complexity. BMC Bioinformatics. 5(1):113 in 19 pages.
Emsley et al., 2010. Features and development of *Coot*. Acta crystallographica Section D, Biol. Crystallo. 66:486-501.
Fontaine et al., Long-term stabilization of maleeimide-thiol conjugates. Bioconjug Chem. 26(1):145-152.
Franklin et al., May 1980, Localization of the amino acid substitution site in a new variant of human serum albumin, albumin Mexico-2, PNAS. USA, 77(5):2505-2509.
Fritzer et al., 1996, Cytotoxic effects of a doxorubicin-transferrin conjugate in multidrug-resistant KB cells. Biochem Pharmacol. 51(4):489-493.
Gabrielsson et al. 2007. Pharmacokinetic and Pharmacodynamic Data Analysis: Concepts and Applications, 4th ed. (Swedish Pharmaceutical Press: Stockholm); Table of Contents in 9 pages.
Gama Sosa et al., 2010, Animal transgenesis: an overview, Brain Struct Funct, 214:91-109.
Ghetie et al., 1997. Increasing the serum persistence of an IgG fragment by random mutagenesis. Nature Biotech. 15:637-640.
Ghuman et al., 2005, Structural basis of the drug-binding specificity of human serum albumin. J Mol Bol. 353:38-52.
Gough et al., 2001, Assignment of Homology to Genome Sequences using a Library of Hidden Markov Models that Represent all Proteins of Known Structure. J Mol Biol. 313:903-919.
Guo et al., 1995, 3'-end-forming signals of yeast mRNA. Mol Cell Biol. 15(11):5983-5990.
Gurbaxani et al., 2006. Analysis of a family of antibodies with different half-lives in mice fails to find a correlation between affinity for FcRn and serum half-life. Mol Immunol. 43(9):1462-1473.
Ha et al., 2006, Fatty acids bound to human serum albumin and its structural variants modulate apolipoprotein B secretion in HepG2 cells, Biochem Biophys Acta 1761:717-724.
Hawkins et al., 2008, Protein nanoparticles as drug carriers in clinical medicine. Adv Drug Deliv Rev. 60(8):876-885.
He et al., 1992. Atomic structure and chemistry of human serum albumin. Nature 358(6383):209-215.
Hinton et al., 2004. Engineered human IgG antibodies with longer serum half-lives in primates. J Biol Chem. 279(8):6213-6216.
Hinton et al., 2006. An engineered human IgG1 antibody with longer serum half-life. J Immunol. 176:346-356.
Ho et al. (1993). X-ray and primary structure of horse serum albumin (*Equus caballus*) at 0.27-nm resolution. Eur J Biochem. 215(1):205-212.
Holm et al., 1998, Dictionary of recurrent domains in protein structures. Proteins 33(1):88-96.
Holm et al., 2000, DaliLite workbench for protein structure comparison. Bioinformatics 16(6):566-567.
Huang et al., 2007, Efficient gene delivery targeted to the brain using a transferrin-conjugated polyethyleneglycol-modified polyamidoamine dendrimer. FASEB J. 21(4):1117-1125.
Humphries et al., 1994, Conjugation of synthetic peptides to carrier proteins for cell adhesion studies. J Tissue Cult Meth. 16(3-4):239-242.
Humphreys et al., 2007, Alternative antibody Fab' fragment PEGylation strategies: combination of strong reducing agents, disruption of the interchain disulphide bond and disulphide engineering. Protein Eng Des Sel. 20(5):227-234.
Hussain et al., 2006, Fat-free Albumin as a Novel Drug Delivery System. Int'l J Peptide Res Therapeutics 12(3):311-315.
Israel et al., 1993. Immunoglobulin G binding sites on the human foetal intestine: a possible mechanism for the passive transfer of immunity from mother to infant. Immunol. 79(1):77-81.
Iwao et al., 2007, Effect of one point mutation on the structural and pharmacokinetic properties of human serum albumin, The Pharmaceutical Society of Japan, Summary of Annual Meeting, 127(3):154 (w/Translation).

(56) References Cited

OTHER PUBLICATIONS

Jones D.T., 1999, GenTHREADER: An efficient and reliable protein fold recognition method for genomic sequences. J Mol Biol. 287(4):797-815.
Kabsch W., 2010. XDS. Acta crystallographica Section D, Biol Crystallogr. 66:125-132.
Kacskovics et al., 2011, Recent advances using FcRn overexpression, Landes Bioscience 3(5) 431-439.
Katoh et al., 2002, MAFFT: A novel method for rapid multiple sequence alignment based on fast Fourier transform. Nucleic Acids Res. 30(14):3059-3066.
Katoh et al., 2005, MAFFT Version 5: Improvement in accuracy of multiple sequence alignment. Nucleic Acids Res. 33(2):511-518.
Katoh et al., 2009, Multiple alignment of DNA sequences with MAFFT. Methods Mol Biol. 537:39-64.
Katoh et al., 2010, Parallelization of the MAFFT multiple sequence alignment program. Bioinformatics 26(15): 1899-1900.
Kavimandan et al., 2006, Synthesis and characterization of insulin-transferrin conjugates. Bioconjug Chem. 17(6):1376-1384.
Kawamata et al., Aug. 10, 2010 Generation of genetically modified rats from embryonic stem cells, PNAS, 107(32):14223-14228.
Kiessling et al., 2002, Magnetic resonance imaging of nude mice with heterotransplanted high-grade squamous cell carcinomas: use of a low-loaded,covalently bound Gd-Has conjugate as contrast agent with high tumor affinity. Invest Radiol.37(4):193-198.
Kim et al., 2006. Albumin turnover: FcRn-mediated recycling saves as much albumin from degradation as the liver produces. Am J Physiol Gastrointest Liver Physiol. 290:G352-G360.
Kim et al., 2007. Kinetics of FcRn-mediated recycling of IgG and albumin in human: Pathophysiology and therapeutic implications using a simplified mechanism-based model. Clin Immunol. 122(2):146-155.
Kjeldsen et al., 1998, Secretory expression of human albumin domains in *Saccharomyces cerevisiae* and their binding of myristic acid and an acylated insulin analogue. Protein Expr Purif. 13(2):163-169.
Kontermann, 2011, Strategies for extended serum half-life or protein therapeutics, Curr Opin Biotech. 22:1-9.
Kren et al., 1998, In vivo site-directed mutagenesis of the factor IX gene by chimeric RNA/DNA oligonucleotides. Nat Med. 4(3):285-290.
Krieger et al., Jul. 4, 2014, YASARA View—molecular graphics for all devices—from smartphones to workstations. Bioinformatics 30(20) 2981-2982.
Krissinel et al., 2007. Inference of macromolecular assemblies from crystalline state. Journal of molecular biology 372, 774-797 (2007).
Kuo et al., 2011. Neonatal Fc receptor and IgG-based therapeutics. mAbs 3(5):422-430.
Labro et al., 1986. A proton nuclear magnetic resonance study of human serum albumin in the neutral pH region. Biochim Biophys Acta 873(2):267-278.
Lawn et al, 1981, The sequence of human serum albumin cDNA and its expression in *E. coli*, Nucl Acids Res. 9(22):6103-6114.
Lee et al., 2005, Evaluation of transferrin-polyethylenimine conjugate for targeted gene delivery. Arch Pharm Res. 28(6):722-729.
Li et al., 2008, Germline competent embryonic stem cells derived from rat blastocysts, Cell, 135:1299-1310.
Lim et al., 2004, Transferrin-oligomers as potential carriers in anticancer drug delivery. Pharm Res. 21(11):1985-1992.
Lindahl et al., 2000, Identification of related proteins on family, superfamily and fold level. J Mol Biol. 295(3):613-615.
Lowman et al., 1991, Selecting high-affinity binding proteins by monovalent phage display. Biochemistry 30(45):10832-10838.
Lubgan et al., 2002, A Transferrin conjugate of adriamycin-synthesis and potential chemotherapeutic efficacy. Cell Mol Biol Lett. 7(Suppl):98.
Martin et al., 1982, Irreversible coupling of immunoglobulin fragments to preformed vesicles. An improved method for liposome targeting. J Biol Chem. 257(1):286-288.

Martin et al., 2001. Crystal structure at 2.8 Å of an FcRn/heterodimeric Fc complex: Mechanism of pH-dependent binding. Mol Cell 7(4):867-877.
McCoy et al., 2007. Phaser crystallographic software. J Applied Crystallogr. 40:658-674.
McGraw et al., 1987, Functional expression of the human transferring receptor cDNA in Chinese hamster ovary cells deficient in endogenous transferring receptor. J Cell Biol. 105(1):207-214.
McGuffin et al., 2003, Improvement of the GenTHREADER method for genomic fold recognition. Bioinformatics 19(7):874-881.
Minghetti et al., 1986, Molecular structure of the human albumin gene is revealed by nucleotide sequence within q11-22 of chromosome 4*, J. Bio Chem. 261(15): 6747-6757.
Mishra et al., 2006, Targeted brain delivery of AZT via transferrin anchored pegylated albumin nanoparticles. J Drug Targeting 14(1):45-53.
Munoz et al., 2009, Constraints to progress in embryonic stem cells from domestic species, Stem Cell Rev and Rep, 5:6-9.
Murshudov et al., 1997. Refinement of macromolecular structures by the maximum-likelihood method. Acta Crystallogr D Biol Crystallogr. 53(Pt 3):240-255.
Ner et al., 1988, A simple and efficient procedure for generating random point mutations and for codon replacements using mixed oligodeoxynucleotides. DNA 7(2):127-134.
Ness et al., 1999, DNA shuffling of subgenomic sequences of subtilisin. Nature Biotechnol. 17(9):893-896.
Neumann et al., 2010, Native albumin for targeted drug delivery, Expert Opin. Drug Deliv., 7(8):1-11.
Nobs et al., 2004, Current methods for attaching targeting ligands to liposomes and nanoparticles. J Pharma Sci. 93(8):1980-1992.
O'Keefe et al., 1985, Characterization of a transferrin-diphtheria toxin conjugate. J Biol Chem. 260(2):932-937.
Öner et al., 1993, Preparation of small gelatin and albumin microparticles by a carbon dioxide atomization. Pharm Res., 10(9):1385-1388.
Pandjaitan et al., 2000, *Escherichia coli* expression and purification of recombinant dog albumin, a cross-reactive animal allergen. J Allergy Clin Immunol. 105(2 Pt):279-285.
Payne et al., 2008, Modulation of chaperone gene expression in mutagenized *Saccharomyces cerevisiae* strains developed for recombinant human albumin production results in increased production of multiple heterologous proteins. Appl Environ Microbiol. 74(24):7759-7766.
Peters [Ed], 1996, *All about Albumin: Biochemistry, Genetics and Medical Applications*, Academic Press, Cooperstown, NY, Chapter 2: pp. 9-23.
Petitpas et al., 2001, Crystal Structure Analysis of Warfarin Binding to Human Serum Albumin Anatomy of Drug Site I. J Biol Chem 276(25):22804-22809.
Petitpas et al., 2001, Crystal structures of human serum albumin complexed with monounsaturated and polyunsaturated fatty acids. J Mol Biol. 314(5):955-960.
Petitpas et al., 2003. Structural basis of albumin-thyroxine interactions and familial dysalbuminemic hyperthyroxinemia. PNAS U.S.A. 100(11):6440-6445 (2003).
Petkova et al., 2006. Enhanced half-life of genetically engineered human IgG1 antibodies in a humanized FcRn mouse model: potential application in humorally mediated autoimmune disease. Int immunol. 18(12):1759-1769.
Piedrahita et al., 2011, Perspectives on transgenic livestock in agriculture and biomedicine: an update, Repro Fertility Develop., 23:56-63.
Presley et al., 1993, The End2 mutation in CHO cells slows the exit of Transferring receptors from the recycling compartment byt bulk membrane recycling is unaffected. J Cell Biol. 122(6):1231-1241.
Rakestraw et al., 2006. A flow cytometric assay for screening improved heterologous protein secretion in yeast. Biotechnol Prog. 22(4):1200-1208.
Reidhaar-Olson et al., 1988, Combinatorial cassette mutagenesis as a probe of the informational content of protein sequences. Science 241(4861):53-57.
Rodewald et al., 1984, Receptor-mediated transport of IgG. J Cell Biol. 99:159s-164s.

(56) References Cited

OTHER PUBLICATIONS

Romanos et al., 1992, Foreign gene expression in yeast: a review. Yeast 8: 423-488.
Sand et al, Dec. 12, 2014, Interaction with both domain I and III of albumin is required for optimal pH-dependent binding to the neonatal Fc receptor (FcRn)*, J Biol Chem 289(50):34583-35894.
Scherer et al., 1979, Replacement of chromosome segments with altered DNA sequences constructed in vitro. PNAS U.S.A. 76(10):4951-4955.
Shindyalov et al., 1998, Protein structure alignment by incremental combinatorial extension (CE) of the optimal path. Protein Eng. 11(9):739-747.
Sleep et al., 2013, Albumin as a versatile platform for drug half-life extension, Biochimca et Biophysica Acta, http://dx/doi/org/10.1016/j.bbagen.2013.04.023; in 9 pages.
Smith et al., Jun. 2015 (online), A platform for efficient, thiol-stable conjugation to albumin's native single accessible cysteine. Org Biomol Chem. 13(29):7946-7949.
Sogami et al., 1968. Isomerization reactions of charcoal-defatted bovine plasma albumin. The N-F transition and acid expansion. Biochemistry 7(6): 2172-2182.
Sogami et al., 1969. The microheterogeneity of plasma albumins. V. Permutations in disulfide pairings as a probable source of microheterogeneity in bovine albumin. Biochemistry 8(1):49-58.
Spiegelberg et al., 1968, Catabolism of human γG-immunoglobulins of different heavy chain subclasses. I. Catabolism of γG-myeloma proteins in man. J Clin Invest. 47(10):2323-2330.
Stapleton et al., 2011. Competition for FcRn-mediated transport gives rise to short half-life of human IgG3 and offers therapeutic potential. Nature Comm. 2:599; 9 pages.
Storici et al., 2001, In vivo site-directed mutagenesis using oligonucleotides. Nat Biotechnol. 19(8):773-776.
Sundaram et al, Aug. 21, 1998, Chimeric constructs between human and rat equilibrative nucleoside transporters (hENT1 and rENT1) reveal hENT1 structural domains interacting with coronary vasoactive drugs, J. Bio Chemistry, 273(34):21519-21525.
Syed et al., 1997, Potent antithrombin activity and delayed clearance from the circulation characterize recombinant hirudin genetically fused to albumin, Blood 89(9):3243-3252.
Thompson et al., 1994, CLUSTAL W: Improving the sensitivity of progressive multiple sequence alignment through sequence weighting, position-specific gap penalties and weight matrix choice. Nucleic Acids Res. 22(22):4673-4680.
Tian et al., 2004, Accurate multiplex gene synthesis from programmable DNA microchips. Nature 432(7020):1050-1054.
Valkonen et al., 2003, Effects of inactivation and constitutive expression of the unfolded-protein response pathway on protein production in the yeast *Saccharomyces cerevisiae*. Applied Environ Microbiol., 69(4):2065-2072.
Viuff et al., 2016, Generation of a double transgenic humanized neonatal Fc receptor (FcRn)/albumin mouse to study the pharmacokinetics of albumin-linked drugs, J Controlled Release, 223:22-30.
Wang et al. 2011. Monoclonal antibodies with identical Fc sequences can bind to FcRn differentially with pharmacokinetic consequences. Drug Metabol Disposition. 39:1469-1477.
Weaver et al., 2003, Transferrin receptor ligand-targeted toxin conjugate (Tf-CRM107) for therapy of malignant gliomas. J Neurooncol. 65(1):3-13.
Wenning et al., 1998, Quantitative analysis of protein synthesis inhibition and recovery in CRM107 immunotoxin-treated HeLac cells. Biotechol Bioeng. 57(4):484-496.
Widera et al., 2003, Transcytosis of GCSF-transferring across rat alveolar epithelial cell monolayers. Pharm Res. 20(8):1231-1238.
Xia et al., 2000, Hypoglycemic effect of insulin-transferrin conjugate in streptozotocin-induced diabetic rats. J Pharmacol Exp Ther. 295(2):594-600.
Yang et al., 2012, Genetic modification of domestic animals for agriculture and biomedical applications, in Ghista [Ed], *Biomedical Science, Engineering and Technology*, Chapter 29, pp. 697-726.
Yazdi et al., 1994, Quantitative Analysis of Protein Synthesis Inhibition by Transferrin-Toxin Conjugates. Cancer Res. 54(24):6387-6394.
Yeung et al., 2009. Engineering human IgG1 affinity to human neonatal Fc receptor: Impact of affinity improvement on pharmacokinetics in primates. J Immunol. 182:7663-7671.
Yin et al., 2007, Select what you need: a comparative evaluation of the advantages and limitations of frequently used expression systems for foreign genes, J Biotech., 127:335-347.
Database NCBI—Accession No. AAA98797 (May 1996).
Database NCBI—Accession No. AAH49971 (Jun. 2007).
Database NCBI—Accession No. AAH85359 (Jul. 2006).
Database Swiss prot—Accession No. Q5XLE4.1 (May 2011).
Database Swiss prot—Accession No. A6YF56 (Jun. 2010).
Database NCBI—Accession No. XP-517233.2 (Sep. 2006).
Database NCBI—Accession No. NP_001182578.1 (Mar. 2014).
Katoh et al., 2007, PartTree: an algorithm to build an approximate tree from a large number of unaligned sequences. BioInformatics 23(3): 372-374.
Madison et al., 1994, Genetic variants of human serum albumin in Italy, Proc Nat Acad Sci. USA, 91:6476-6480.
Elzoghby et al., 2012. Albumin-based nanoparticles as potential controlled release drug delivery systems, J Control Release. 157(2):168-182.

* cited by examiner

FcRn/HSA SPR
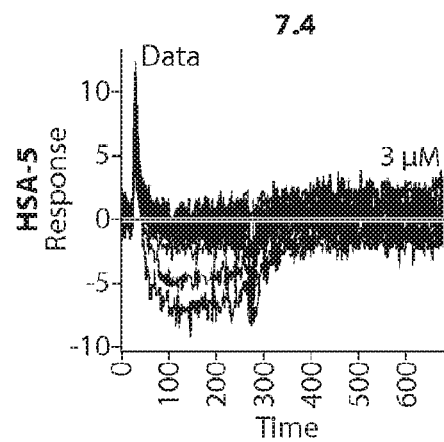
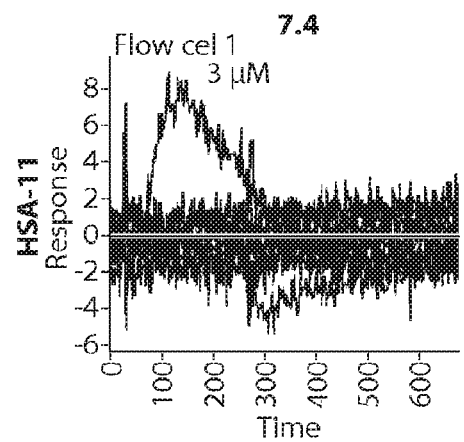
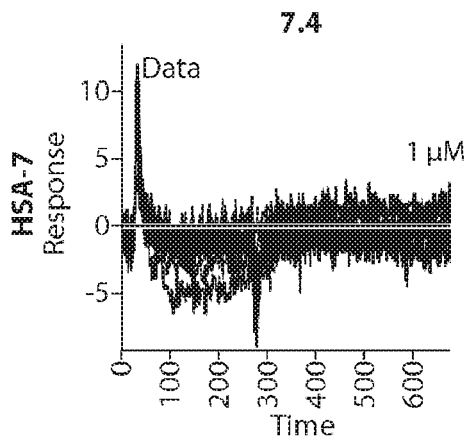
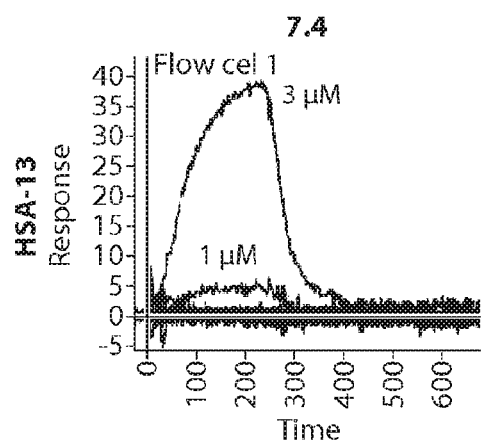
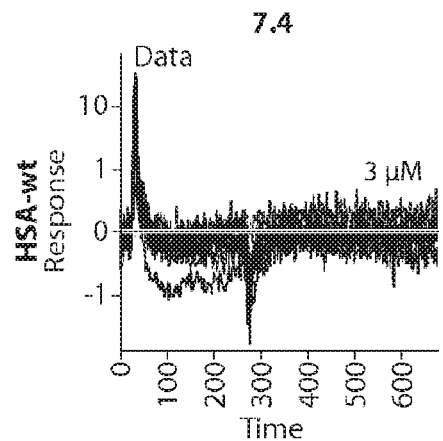
Fig. 1D

| Rank Order of Binding | | ~Kd at pH 5.5 | V418 | T420 | E505 | V547 | Other |
|---|---|---|---|---|---|---|---|
| 1 | HSA-15 | 3 nM | M | A | R | | V424I, N429D |
| 2 | HSA-13 | 3 nM | M | A | G | A | |
| 3 | HSA-12 | 6 nM | M | A | | A | |
| 4 | HSA-7 | 10 nM | | | G | A | |
| 5 | HSA-21 | 12 nM | M | A | R | | |
| 6 | HSA-11 | 25 nM | M | A | G | | |
| 7 | HSA-2 | 25 nM | | | | | K573Y |
| 8 | HSA-14 | 50 nM | M | A | G | | M44GV, A449V, T467M, A552T |
| 9 | HSA-5 | 50 nM | | | | A | |
| 10 | HSA-10 | 75 nM | M | A | | | |
| 11 | HSA-6 | >100 nM | | | G | | |
| 12 | HSA-9 | >100 nM | | A | | | |
| 13 | HSA-18 | >100 nM | | | | | V424I |
| 14 | HSA-3 | | | | | | WT-D3 |
| 15 | HSA-1 | | | | | | WT |
| 16 | HSA-4 | | | | | | E492G |
| 17 | HSA-8 | | M | | | | |
| 18 | HSA-16 | | | | R | | |
| 19 | HSA-17 | | | | K | | |
| 20 | HSA-19 | | | | | | N429D |
| 21 | HSA-20 | | | | | | M446V, A449V |
| 22 | HSA-22 | | | | | | T467M |
| 23 | HSA-23 | | | | | | A552T |
| 24 | HSA-23 | | | | | | PBS |

Increasing affinity

~wt binding

| Molecule | Dose | N (animals) | Cmax (μg/mL) | AUC (μg*hr/mL) | Cl (ml/min/kg) | V_dist (mL/kg) | T1/2 (Hrs) | T1/2_α (Hrs) | T1/2_β (Hrs) |
|---|---|---|---|---|---|---|---|---|---|
| HSA-wt | 1 mg/kg | 6 | 18.2 | 1,808 | 0.010 | 165 | 182 | 4.4 | 152 |
| HSA-7 | 1 mg/kg | 2 | 38.1 | 2,824 | 0.0059 | 115 | 225 | 5.1 | 239 |
| HSA-wt | 5 mg/kg | 2 | 239 | 15,338 | 0.0059 | 120 | 251 | 9.0 | 218 |
| HSA-7 | 5 mg/kg | 2 | 196 | 17,888 | 0.0047 | 125 | 302 | 11.0 | 279 |
| HSA-wt | All | 8 | | | 0.0090 | 153 | 199 | 5.6 | 168 |
| HSA-7 | All | 4 | | | 0.0053 | 120 | 264 | 8.0 | 259 |

Non-compartmental fit | Biexponetial fit

Fig. 6

| Molecule | Dose | Cmax (μg/mL) | AUC (μg*hr/mL) | Cl (ml/min/kg) | V_dist (mL/kg) | T1/2 (Hrs) |
|---|---|---|---|---|---|---|
| IL2-HSA-wt | 0.5 mg/kg | 4.3 | 32.8 | 0.26 | 217 | 9.9 |
| IL2-HSA-13 | 0.5 mg/kg | 4.3 | 43.7 | 0.19 | 188 | 11.4 |

SEQUENCE LISTING

```
<160> NUMBER OF SEQ ID NOS: 28

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30
```

-continued

His Arg Phe Lys Asp Leu Gly Glu Glu Asn Phe Lys Ala Leu Val Leu
            35                  40                  45
Ile Ala Phe Ala Gln Tyr Leu Gln Gln Cys Pro Phe Glu Asp His Val
 50                  55                  60
Lys Leu Val Asn Glu Val Thr Glu Phe Ala Lys Thr Cys Val Ala Asp
 65                  70                  75                  80
Glu Ser Ala Glu Asn Cys Asp Lys Ser Leu His Thr Leu Phe Gly Asp
                 85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
            115                 120                 125
His Lys Asp Asp Asn Pro Asn Leu Pro Arg Leu Val Arg Pro Glu Val
130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
            180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Gln Arg Leu Lys Cys
            210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
            275                 280                 285
Cys Glu Asn Gln Asp Ser Ile Ser Ser Lys Leu Lys Glu Cys Cys Glu
            290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
            355                 360                 365
Leu Leu Leu Arg Leu Ala Lys Thr Tyr Glu Thr Thr Leu Glu Lys Cys
            370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
            435                 440                 445

-continued

```
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu
```

<210> SEQ ID NO 2
<211> LENGTH: 585
<212> TYPE: PRT
<213> ORGANISM: Homo sapiens

<400> SEQUENCE: 2

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
        50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
```

```
Arg Ala Phe Lys Ala Trp Ala Val Ala Arg Leu Ser Gln Arg Phe Pro
        210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 3
<211> LENGTH: 37
<212> TYPE: PRT
<213> ORGANISM: Homo sapiens

<400> SEQUENCE: 3
```

-continued

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
                20                  25                  30

Val Lys Gly Arg Gly
            35

<210> SEQ ID NO 4
<211> LENGTH: 110
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 5
<211> LENGTH: 30
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
                20                  25                  30

<210> SEQ ID NO 6
<211> LENGTH: 20
<212> TYPE: PRT
<213> ORGANISM: Homo sapiens

<400> SEQUENCE: 6

Ile Val Glu Gln Cys Cys Thr Ser Ile Cys Ser Leu Tyr Gln Leu Glu
1               5                   10                  15

Asn Tyr Cys Asn
            20

<210> SEQ ID NO 7
<211> LENGTH: 35
<212> TYPE: PRT
<213> ORGANISM: Homo sapiens

<400> SEQUENCE: 7

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu

```
                    20                  25                  30

Gln Lys Arg
        35

<210> SEQ ID NO 8
<211> LENGTH: 216
<212> TYPE: PRT
<213> ORGANISM: Homo sapiens

<400> SEQUENCE: 8

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                    20                  25                  30

His Val His Tyr Gly Trp Gly Asp Pro Ile Arg Leu Arg His Leu Tyr
                35                  40                      45

Thr Ser Gly Pro His Gly Leu Ser Ser Cys Phe Leu Arg Ile Arg Ala
        50                  55                      60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                    85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                    165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215

<210> SEQ ID NO 9
<211> LENGTH: 209
<212> TYPE: PRT
<213> ORGANISM: Homo sapiens

<400> SEQUENCE: 9

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                    20                  25                  30

Asp Ser Ser Pro Leu Leu Gln Phe Gly Gly Gln Val Arg Gln Arg Tyr
                35                  40                      45

Leu Tyr Thr Asp Asp Ala Gln Gln Thr Glu Ala His Leu Glu Ile Arg
        50                  55                      60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
```

```
                       85                  90                  95
Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 10
<211> LENGTH: 251
<212> TYPE: PRT
<213> ORGANISM: Homo sapiens

<400> SEQUENCE: 10

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 11
<211> LENGTH: 153
<212> TYPE: PRT
<213> ORGANISM: Homo sapiens

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 12
<211> LENGTH: 162
<212> TYPE: PRT
<213> ORGANISM: Homo sapiens

<400> SEQUENCE: 12

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 13
<211> LENGTH: 84
<212> TYPE: PRT
<213> ORGANISM: Homo sapiens

<400> SEQUENCE: 13

Met Ala Leu Ser Ser Gln Ile Trp Ala Ala Cys Leu Leu Leu Leu
1               5                   10                  15

Leu Leu Ala Ser Leu Thr Ser Gly Ser Val Phe Pro Gln Gln Thr Gly
                20                  25                  30

Gln Leu Ala Glu Leu Gln Pro Gln Asp Arg Ala Gly Ala Arg Ala Ser
            35                  40                  45

Trp Met Pro Met Phe Gln Arg Arg Arg Arg Asp Thr His Phe Pro
    50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 14
<211> LENGTH: 461
<212> TYPE: PRT
<213> ORGANISM: Homo sapiens

<400> SEQUENCE: 14

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

```
Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 15
<211> LENGTH: 193
<212> TYPE: PRT
<213> ORGANISM: Homo sapiens

<400> SEQUENCE: 15

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

```
Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 16
<211> LENGTH: 207
<212> TYPE: PRT
<213> ORGANISM: Homo sapiens

<400> SEQUENCE: 16

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 17
<211> LENGTH: 188
<212> TYPE: PRT
<213> ORGANISM: Homo sapiens

<400> SEQUENCE: 17

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80
```

```
Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
            115                 120                 125

Thr Glu Thr Pro Leu Met Lys Glu Asp Ser Ile Leu Ala Val Arg Lys
        130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 18
<211> LENGTH: 187
<212> TYPE: PRT
<213> ORGANISM: Homo sapiens

<400> SEQUENCE: 18

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
            35                  40                  45

Leu Glu Tyr Cys Leu Lys Asp Arg Met Asn Phe Asp Ile Pro Glu Glu
        50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 19
<211> LENGTH: 166
<212> TYPE: PRT
<213> ORGANISM: Homo sapiens

<400> SEQUENCE: 19

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30
```

```
Asn Leu Lys Lys Tyr Phe Asn Ala Gly His Ser Asp Val Ala Asp Asn
             35                  40                  45

Gly Thr Leu Phe Leu Gly Ile Leu Lys Asn Trp Lys Glu Ser Asp
 50                  55                  60

Arg Lys Ile Met Gln Ser Gln Ile Val Ser Phe Tyr Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Arg
                100                 105                 110

Asp Asp Phe Glu Lys Leu Thr Asn Tyr Ser Val Thr Asp Leu Asn Val
                115                 120                 125

Gln Arg Lys Ala Ile His Glu Leu Ile Gln Val Met Ala Glu Leu Ser
                130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 20
<211> LENGTH: 177
<212> TYPE: PRT
<213> ORGANISM: Homo sapiens

<400> SEQUENCE: 20

Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
                 20                  25                  30

Ser Lys Met Gln Ala Phe Arg Ile Trp Asp Val Asn Gln Lys Thr Phe
             35                  40                  45

Tyr Leu Arg Asn Asn Gln Leu Val Ala Gly Tyr Leu Gln Gly Pro Asn
 50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
                115                 120                 125

Asp Ser Gly Pro Thr Thr Ser Phe Glu Ser Ala Ala Cys Pro Gly Trp
130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 21
<211> LENGTH: 302
<212> TYPE: PRT
<213> ORGANISM: Aspergillus flavus

<400> SEQUENCE: 21

Met Ser Ala Val Lys Ala Ala Arg Tyr Gly Lys Asp Asn Val Arg Val
```

-continued

```
          1               5                  10                 15
        Tyr Lys Val His Lys Asp Glu Lys Thr Gly Val Gln Thr Val Tyr Glu
                     20                  25                  30

Met Thr Val Cys Val Leu Leu Glu Gly Glu Ile Glu Thr Ser Tyr Thr
                     35                  40                  45

Lys Ala Asp Asn Ser Val Ile Val Ala Thr Asp Ser Ile Lys Asn Thr
                     50                  55                  60

Ile Tyr Ile Thr Ala Lys Gln Asn Pro Val Thr Pro Pro Glu Leu Phe
        65                  70                  75                  80

Gly Ser Ile Leu Gly Thr His Phe Ile Glu Lys Tyr Asn His Ile His
                                 85                  90                  95

Ala Ala His Val Asn Ile Val Cys His Arg Trp Thr Arg Met Asp Ile
                     100                 105                 110

Asp Gly Lys Pro His Pro His Ser Phe Ile Arg Asp Ser Glu Lys
                     115                 120                 125

Arg Asn Val Gln Val Asp Val Val Glu Gly Lys Gly Ile Asp Ile Lys
                     130                 135                 140

Ser Ser Leu Ser Gly Leu Thr Val Leu Lys Ser Thr Asn Ser Gln Phe
        145                 150                 155                 160

Trp Gly Phe Leu Arg Asp Glu Tyr Thr Thr Leu Lys Glu Thr Trp Asp
                                 165                 170                 175

Arg Ile Leu Ser Thr Asp Val Asp Ala Thr Trp Gln Trp Lys Asn Phe
                     180                 185                 190

Ser Gly Leu Gln Glu Val Arg Ser His Val Pro Lys Phe Asp Ala Thr
                     195                 200                 205

Trp Ala Thr Ala Arg Glu Val Thr Leu Lys Thr Phe Ala Glu Asp Asn
        210                 215                 220

Ser Ala Ser Val Gln Ala Thr Met Tyr Lys Met Ala Glu Gln Ile Leu
        225                 230                 235                 240

Ala Arg Gln Gln Leu Ile Glu Thr Val Glu Tyr Ser Leu Pro Asn Lys
                                 245                 250                 255

His Tyr Phe Glu Ile Asp Leu Ser Trp His Lys Gly Leu Gln Asn Thr
                     260                 265                 270

Gly Lys Asn Ala Glu Val Phe Ala Pro Gln Ser Asp Pro Asn Gly Leu
                     275                 280                 285

Ile Lys Cys Thr Val Gly Arg Ser Ser Leu Lys Ser Lys Leu
                     290                 295                 300

<210> SEQ ID NO 22
<211> LENGTH: 126
<212> TYPE: PRT
<213> ORGANISM: Homo sapiens

<400> SEQUENCE: 22

Met His Leu Ser Gln Leu Leu Ala Cys Ala Leu Leu Thr Leu Leu
        1               5                  10                 15

Ser Leu Arg Pro Ser Glu Ala Lys Pro Gly Ala Pro Lys Val Pro
                     20                  25                  30

Arg Thr Pro Pro Ala Glu Glu Leu Ala Glu Pro Gln Ala Ala Gly Gly
                     35                  40                  45

Gly Gln Lys Lys Gly Asp Lys Ala Pro Gly Gly Gly Ala Asn Leu
                     50                  55                  60

Lys Gly Asp Arg Ser Arg Leu Leu Arg Asp Leu Arg Val Asp Thr Lys
        65                  70                  75                  80
```

```
Ser Arg Ala Ala Trp Ala Arg Leu Leu Gln Glu His Pro Asn Ala Arg
            85                  90                  95

Lys Tyr Lys Gly Ala Asn Lys Lys Gly Leu Ser Lys Gly Cys Phe Gly
        100                 105                 110

Leu Lys Leu Asp Arg Ile Gly Ser Met Ser Gly Leu Gly Cys
        115                 120                 125
```

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

```
Gly Ser Gly Gly Ser
1               5
```

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Gly Gly Gly Gly Ser
1               5
```

<210> SEQ ID NO 25
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

```
Gly Gly Gly Ser
1
```

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 26

```
His His His His His His
1               5
```

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 27

Gly Gly Gly Gly Ser Gly Gly Gly Gly Ser Gly Gly Gly Gly Ser
1               5                   10                  15

<210> SEQ ID NO 28
<211> LENGTH: 206
<212> TYPE: PRT
<213> ORGANISM: Homo sapiens

<400> SEQUENCE: 28

Leu Val Glu Glu Pro Gln Asn Leu Ile Lys Gln Asn Cys Glu Leu Phe
1               5                   10                  15

Glu Gln Leu Gly Glu Tyr Lys Phe Gln Asn Ala Leu Leu Val Arg Tyr
            20                  25                  30

Thr Lys Lys Val Pro Gln Val Ser Thr Pro Thr Leu Val Glu Val Ser
        35                  40                  45

Arg Asn Leu Gly Lys Val Gly Ser Lys Cys Cys Lys His Pro Glu Ala
    50                  55                  60

Lys Arg Met Pro Cys Ala Glu Asp Tyr Leu Ser Val Val Leu Asn Gln
65                  70                  75                  80

Leu Cys Val Leu His Glu Lys Thr Pro Val Ser Asp Arg Val Thr Lys
                85                  90                  95

Cys Cys Thr Glu Ser Leu Val Asn Arg Arg Pro Cys Phe Ser Ala Leu
            100                 105                 110

Glu Val Asp Glu Thr Tyr Val Pro Lys Glu Phe Asn Ala Glu Thr Phe
        115                 120                 125

Thr Phe His Ala Asp Ile Cys Thr Leu Ser Glu Lys Glu Arg Gln Ile
    130                 135                 140

Lys Lys Gln Thr Ala Leu Val Glu Leu Val Lys His Lys Pro Lys Ala
145                 150                 155                 160

Thr Lys Glu Gln Leu Lys Ala Val Met Asp Asp Phe Ala Ala Phe Val
                165                 170                 175

Glu Lys Cys Cys Lys Ala Asp Asp Lys Glu Thr Cys Phe Ala Glu Glu
            180                 185                 190

Gly Lys Lys Leu Val Ala Ala Ser Gln Ala Ala Leu Gly Leu
        195                 200                 205
```

VARIANT SERUM ALBUMIN WITH IMPROVED HALF-LIFE AND OTHER PROPERTIES

RELATED APPLICATIONS

The present application is a continuation of U.S. application Ser. No. 14/358,857, filed May 16, 2014, which is a U.S. National Phase Application of PCT International Application Number PCT/US2012/065733, filed Nov. 18, 2012, designating the United States of America and published in the English language, which claims priority to U.S. Application Ser. No. 61/561,785, filed Nov. 18, 2011; U.S. Application Ser. No. 61/576,491, filed Dec. 16, 2011; and U.S. Application Ser. No. 61/710,476, filed Oct. 5, 2012. The entire content of each of the foregoing applications is hereby incorporated herein by reference.

SEQUENCE LISTING

The instant application contains a Sequence Listing which has been submitted in ASCII format via EFS-Web and is hereby incorporated by reference in its entirety. Said ASCII copy, created on May 25, 2018, is named SeqList-ALBUM-001C1.txt and is 43 KB in size.

FIELD OF THE INVENTION

The present invention relates to the area of therapeutic and diagnostic proteins, materials for producing such proteins, and methods for their production and use.

BACKGROUND

Serum albumin is an abundant plasma protein that that is essential for maintaining oncotic pressure and is useful in regulating the volume of circulating blood. Serum albumin has therapeutic uses and is indicated, for example, to treat hypovolemia and hypoalbuminemia (e.g., hypoalbuminemia associated with inadequate production, excessive catabolism, hemorrhage, excessive renal excretion, redistribution within the body e.g., due to surgery or inflammatory conditions, burns, adult respiratory distress syndrome, nephrosis), and may be used prior to or during cardiopulmonary bypass surgery or to treat hemolytic disease of the newborn. Serum albumin can also be used in association with other agents.

SUMMARY

There is a need for improved variant sequences of serum albumin. Such variant sequences can be used, e.g., to prepare or provide a protein product (e.g., a therapeutic or diagnostic protein product). In embodiments the protein product has improved properties (e.g., higher recycling fraction via an FcRn mechanism and/or improved pharmacokinetic properties, e.g., increased half-life and/or reduced clearance), e.g., as compared with a protein product that is prepared using a corresponding native (e.g., wild type) serum albumin sequence (e.g., a mammalian serum albumin, e.g., human serum albumin or bovine serum albumin). As used herein, a "corresponding native serum albumin" (e.g., a naturally occurring serum albumin or a wild type serum albumin) refers to a corresponding full length native serum albumin sequence, or fragment thereof, of which the variant serum albumin polypeptide (VSA) is a variant. The disclosure provided herein includes disclosure of proteins that comprise variant serum albumin sequences and methods of using such proteins.

In some aspects, the disclosure provides a variant serum albumin polypeptide (VSA). In some embodiments, the variant is a variant of a full-length serum albumin polypeptide sequence (e.g., a human serum albumin polypeptide sequence, or a serum albumin polypeptide sequence from another species, e.g., a bovine serum albumin polypeptide sequence). In other embodiments, the variant is a variant of a fragment of a serum albumin polypeptide sequence (e.g., a fragment of the human serum albumin polypeptide sequence, or a fragment of a serum albumin polypeptide sequence from another species, e.g., a fragment of the bovine serum albumin polypeptide sequence). In some embodiments, the fragment comprises a domain III of a serum albumin polypeptide sequence (e.g., domain III of the human serum albumin polypeptide sequence).

In some aspects, the present disclosure provides an isolated, recombinant protein that comprises a VSA, e.g., a VSA that is or comprises a variant of domain III of a naturally-occurring serum albumin. In some embodiments, the VSA is in a polypeptide that also includes a heterologous sequence, e.g., a heterologous sequence as described herein. For example, a fusion polypeptide can comprise a VSA and a heterologous sequence.

In some embodiments, the VSA has or comprises a mutation at one or more of the positions corresponding to V418, T420, V424, E505 and V547 of serum albumin.

In some embodiments, the VSA can bind to an FcRn (e.g., human FcRn) at a pH in the range of 5.5 to 6.0 (e.g., at a pH of 5.5, 5.6, 5.7, 5.8, 5.9, or 6.0). In some embodiments, the VSA binds to an FcRn (e.g., human FcRn) with higher affinity than does a corresponding native serum albumin. In some embodiments, the higher affinity binding occurs at a specified pH (e.g., at a pH of 5.5, 5.6, 5.7, 5.8, 5.9, 6.0) or in a specified pH range, e.g., at a pH in the range of 5.5-6.0 or 6.0-6.5.

In some embodiments, the ratio of the binding affinity of the VSA, or of the recombinant protein comprising the VSA, at a pH of 5.5 to 6.0 to the binding affinity at a pH of 7.0 to 7.4 is greater than or equal to the ratio for a corresponding native serum albumin (e.g., a corresponding native human serum albumin). In some embodiments, the ratio of the binding affinity of the VSA, or of the recombinant protein comprising the VSA, at a pH of 5.5 to 6.0 to that at a pH of 7.0 to 7.4 is 5; 10; 50; 100; 1000; 10,000; 100,000; or 1 million times that of a corresponding native human albumin.

In some embodiments, the VSA, or the recombinant protein comprising the VSA, binds to FcRn at a pH in the range of 7.0 to 7.4 with an affinity not greater than a corresponding native human albumin.

In some embodiments, the disclosure provides an isolated, recombinant protein comprising a VSA that has altered binding properties for an FcRn (e.g., a human FcRn) relative to a corresponding native serum albumin sequence (e.g., the wild-type human serum albumin sequence). The protein can include a heterologous sequence as described herein. In some embodiments, the recombinant protein comprising a VSA binds to FcRn with an affinity that is altered compared to a recombinant protein comprising a wild type albumin (e.g., a wild type human albumin) and the heterologous sequence. In some embodiments, the VSA or recombinant protein comprising the VSA binds to FcRn with a dissociation constant ($K_D$) of less than 50 nM at pH 5.5. In some embodiments, the VSA or recombinant protein has an affinity for FcRn at pH 7.4 that is less than or equal to its affinity for FcRn of a wild type albumin at pH 7.4.

In some embodiments, the VSA has a $K_D$ that is below 100 nM. In some embodiments, the VSA has a $K_D$ that is below 75 nM, below 50 nM, below 40 nM, below 30 nM, below 25 nM, below 20 nM, below 15 nM, below 10 nM, below 9 nM, below 8 nM, below 7 nM, below 6 nM, below 5 nM, or below 4 nM. In some embodiments, the protein has a $K_D$ that is 3 nM or less.

In certain embodiments, the VSA comprises a substitution of V418 with another amino acid, for example, with a methionine. In certain embodiments, the VSA comprises a substitution of T420 with another amino acid, for example, an uncharged amino acid, such as alanine. In certain embodiments, the VSA comprises a substitution of V424 with another amino acid, for example, an uncharged amino acid, such as isoleucine. In certain embodiments, the VSA comprises a substitution of E505 with another amino acid, for example, an uncharged amino acid, such as glycine, or a positively charged amino acid, such as lysine or arginine. In certain embodiments, the VSA comprises a substitution of V547 with another amino acid, for example, an uncharged amino acid, such as alanine.

In some embodiments, the VSA comprises substitutions at two or more (e.g., at two, three, four, or five) of the positions corresponding to V418, T420, V424, E505 and V547. For example, the VSA can comprise two, three, four, or five substitutions selected from V418M, T420A, V424I, E505 (R/K/G) and V547A. In a particular embodiment, the VSA comprises the substitutions V418M, T420A and E505R. In another particular embodiment, the VSA comprises the substitutions V418M, T420A, E505G and V547A.

In some embodiments, the VSA comprises one or more additional substitutions at positions selected from N429, M446, A449, T467, and A552. In some embodiments, the substitutions are selected from N429D, M446V, A449V, T467M, and A552T.

In some embodiments, a protein provided herein includes a VSA that is at least 70%, 75%, 80%, 85%, 90%, 91%, 92%, 93%, 94%, 95%, 96%, 97%, 98%, or 99%, but less than 100% identical to domain III of a naturally occurring serum albumin, e.g., a human serum albumin. In certain embodiments, the protein includes a VSA that is at least 70%, 75%, 80%, 85%, 90%, 91%, 92%, 93%, 94%, 95%, 96%, 97%, 98%, or 99%, but less than 100% identical to domain III of human serum albumin.

In some embodiments, a protein provided herein includes a VSA that differs by at least 1, 2, 3, 4, 5, 6, 7, 8, 9, 10, 15, or 20 residues from a corresponding native serum albumin, e.g., a corresponding human serum albumin sequence. In some embodiments, a protein provided herein includes a VSA that differs by at least 1, but no more than 2, 3, 4, 5, 6, 7, 8, 9, 10, 15, or 20 residues from a corresponding native serum albumin e.g., a corresponding human serum albumin sequence. In embodiments the differences are in domain III, e.g., in domain III of human serum albumin.

In some aspects, the disclosure provides an agent in association with a VSA, e.g., a VSA as described herein. In some embodiments, the agent is a therapeutic or diagnostic agent, e.g., an agent as described herein. In some embodiments, the agent is fused to the VSA or to a protein that comprises the VSA, e.g., in the form of a fusion protein. For example, a VSA can be fused to a heterologous sequence using recombinant genetic techniques. A heterologous sequence can comprise, e.g., the agent, a protein that comprises the agent, or a sequence to which the agent is attached or can be attached.

In some aspects, the disclosure provides an isolated, recombinant protein that comprises a VSA as described herein and a heterologous sequence, e.g., a heterologous sequence as described herein (e.g., the heterologous sequence can be a cytokine, immunoglobulin, cell surface receptor, coagulation protein, or functional fragment of any of these). The protein can also include more than one heterologous sequence. In some embodiments, the VSA is a variant of domain III of a naturally-occurring serum albumin. In some embodiments the recombinant protein is a fusion protein.

In some embodiments, the heterologous sequence comprises a cytokine domain, for example, an amino acid sequence originating or derived from an interleukin-2. In some embodiments, the heterologous sequence comprises an immunoglobulin single-chain variable domain, e.g., an scFv. In some embodiments, the heterologous domain is a scaffold, e.g., an anti-calin, a DARPin, a Surrobody™, Adnectin™, a Domain antibody, Affibody, or fragment of any of the foregoing. In some embodiments, the heterologous sequence comprises a soluble fragment of a cell surface receptor. In some embodiments, the heterologous sequence comprises an enzyme. In still other embodiments, the heterologous sequence comprises a component of a coagulation protein, such as an amino acid sequence originating or derived from coagulation factor VII (FVII) or coagulation factor VIII (FVIII). In some embodiments, the heterologous sequence comprises two or more of the foregoing.

In certain aspects, the protein comprises a first and a second heterologous sequence. In some embodiments, the first and the second heterologous sequence are identical. In some embodiments, the first and second heterologous sequence are in tandem. In other embodiments, the first heterologous sequence is located N-terminal to the variant sequence and the second heterologous sequence is located C-terminal to the variant sequence.

In another aspect, the present disclosure provides an isolated recombinant DNA molecule and/or nucleotide sequence that encodes a polypeptide, peptide, protein or recombinant protein disclosed herein. The recombinant DNA molecule and/or nucleotide sequence comprises a variant nucleotide sequence that encodes a VSA. In some embodiments, the VSA includes at least a variant of domain III of a naturally-occurring serum albumin.

In other aspects, the present disclosure provides a recombinant host cell (e.g., a recombinant CHO cell, or a *Saccharomyces cerevisiae* cell) that has been transformed with a recombinant DNA molecule or nucleotide sequence that encodes a polypeptide, peptide, protein or recombinant protein as disclosed herein. Unless otherwise noted, the term protein includes polypeptides and peptides.

In some aspects, the disclosure provides a method of treatment or diagnosis, the method comprising administering to a subject (e.g., a human or non-human animal) a VSA (e.g., a VSA as described herein), or a pharmaceutical composition comprising a VSA, e.g., a VSA as described herein. In some embodiments, the subject is suffering from a disease or condition in which albumin is indicated. In some embodiments the disease or condition is selected from hypovolemia, hypoalbuminemia, a burn, adult respiratory distress syndrome, nephrosis, and hemolytic disease of the newborn.

In some aspects, the disclosure provides a method of treatment and/or a method of diagnosis, wherein the method comprises administering to a subject an agent (e.g., a therapeutic or diagnostic agent) in association with a VSA (e.g., a VSA as described herein). In some embodiments, the method is a method of treatment that comprises administering to a subject a therapeutic agent in association with a VSA, e.g., a VSA as described herein. In some embodiments, the method is a method of diagnosis that comprises administering to a subject a diagnostic agent in association with a VSA, e.g., a VSA as described herein.

The agent can be any biologically or pharmaceutically active moiety (e.g., a biologic, such as a peptide or nucleotide sequence or a chemical entity such as a small molecule). Typically, the agent is administered in an effective amount and at an effective frequency, e.g., in an amount and frequency that is effective for the desired therapeutic or diagnostic purpose. In some embodiments, the agent is a known therapeutic or diagnostic agent. In some embodiments, the agent comprises an entire known protein, nucleotide sequence or chemical entity. In some embodiments, the agent comprises a fragment or variant of a known protein, nucleotide sequence or chemical entity. The fragment or variant can have the same or similar activity as does the known protein, nucleotide sequence or chemical entity, or the fragment or variant can have altered activity, e.g., an increased desirable activity or a reduced undesirable activity compared with the known protein, nucleotide sequence or chemical entity.

In some embodiments, administering the agent in association with the VSA results in an improved function of the agent. In some embodiments, the improved function is an improved pharmacokinetic property (e.g., increased half-life and/or reduced clearance) of the agent. In some embodiments, the improved function is a reduced effective dosage and/or a reduced effective frequency of administration of the agent compared with the agent when it is administered without the association with VSA. In some embodiments, the improved function is a more desirable delivery level of the agent (e.g., a higher, more consistent, and/or less variable level of delivery). An improved function of the agent can be established, e.g., by comparing the function of the agent when it is administered in association with the VSA with the same function of the agent when it is administered without the association with the VSA (e.g., when the agent is administered alone or when it is administered in association with a corresponding native serum albumin sequence).

In some embodiments in which the agent (e.g., therapeutic or diagnostic agent) is in association with the VSA, the agent is fused to the VSA. In some embodiments, the agent is fused to the VSA via a covalent bond. In some embodiments, the agent is fused to the VSA via a peptide bond. In some embodiments, the agent is fused to the VSA via a non-peptide bond. In some embodiments, the agent is fused to the VSA via a linker, e.g., a linker as described herein. In some embodiments, the agent is fused to the VSA using recombinant genetic methods. In some embodiments, the agent is fused to the VSA using chemical methods.

In some embodiments in which the agent (e.g., therapeutic or diagnostic agent) is in association with the VSA, the agent is not fused to the VSA. In some embodiments, the agent is not fused to the VSA and is stably associated with the VSA. "Stably associated" means that the VSA and the agent can be or remain physically associated at a pH at which they are intended to function, e.g., at an endosomal pH. Typically, the agent and VSA also can be or remain physically associated at a neutral pH. In embodiments, the agent can be associated with the VSA by any means known in the art. For example, the agent can be conjugated to a moiety that is capable of binding the VSA. In some embodiments, the moiety is an albumin binding protein. In some embodiments the moiety is a fatty acid. In some embodiments, the agent is non-covalently bound to the VSA. In embodiments wherein the agent is not fused to the VSA, the agent can be administered before, after, or concurrently with the VSA. In some embodiments, the agent is administered concurrently with the VSA. In some embodiments, the agent is administered at the same frequency as is the VSA. In some embodiments, the agent is administered more or less frequently than the VSA. An advantage of using a VSA can be that a VSA can retain lipophilic features of an albumin, thereby improving solubility of a molecule (e.g., a therapeutic agent).

In some aspects, the disclosure provides a method of treating a subject, the method comprising administering to the subject an effective amount of a therapeutic agent in association with a VSA (e.g., a VSA as described herein), such that the dosage and/or frequency of administration at which the agent produces a therapeutic effect is reduced relative to the dosage and/or frequency of administration at which the agent produces a therapeutic effect when it is not in association with the albumin protein. In some embodiments, In some embodiments, the agent comprises a polypeptide component that is fused to the VSA or to a protein comprising the VSA. In some embodiments, the polypeptide component and the VSA or protein that comprises the VSA are separated by a linker sequence. In some embodiments, the polypeptide component and the VSA or protein that comprises the VSA are covalently linked by a non-peptide bond. In some embodiments, the polypeptide component and the VSA or protein that comprises the VSA are non-covalently and stably associated.

In additional aspects, the present disclosure provides a method of engineering a VSA associated therapeutic agent or a VSA associated diagnostic agent. The method comprises providing a biologically or pharmaceutically active agent (e.g., an agent as described herein) and associating the agent with a VSA as described herein to provide a VSA associated agent; i.e., a VSA associated therapeutic agent or a VSA associated diagnostic agent. "Associating" the agent with the VSA can be done by any means known in the art or any means described herein, e.g., by fusing the agent to the VSA using recombinant genetic and/or chemical means, by conjugating the agent to a moiety that is capable of binding the VSA, or by non-covalent methods.

In some embodiments, the method further comprises formulating the albumin modified agent, or providing a formulation or pharmaceutical composition, for administration to a subject, such as a human subject. In embodiments including an albumin modified diagnostic agent, the method may further comprise administering the albumin modified diagnostic agent to a subject and detecting the albumin modified diagnostic agent, for example, a method wherein the subject is imaged. In embodiments the formulation is in a storage or delivery device, e.g., a syringe.

In some aspects, the present disclosure provides a formulation that comprises a biologically or pharmaceutically active agent (e.g., an agent as described herein) in association with VSA.

Calculations of "homology" or "sequence identity" between two sequences (the terms are used interchangeably herein) can be performed as follows. The sequences are aligned according to the alignments provided herein, or, in the absence of an appropriate alignment, the optimal alignment determined as the best score using the Needleman and Wunsch algorithm as implemented in the Needle algorithm of the EMBOSS package using a Blosum 62 scoring matrix with a gap penalty of 10, and a gap extend penalty of 1. (See Needleman, S. B. and Wunsch, C. D. (1970) J. Mol. Biol. 48:

443-453; Kruskal, J. B. (1983) An overview of sequence comparison In D. Sankoff and J. B. Kruskal, (Eds.), *Time Warps, String Edits and Macromolecules: the Theory and Practice of Sequence Comparison*, pp. 1-44, Addison Wesley, and tools available from the European Bioinformatics Institute (Cambridge UK), described in Rice, P. et al. (2000) Trends in Genetics 16(6): 276-277 and available online at www.ebi.ac.uk/Tools/emboss/align/index.html and emboss.open-bio.org/wiki/Appdoc:Needle.) The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. To determine collective identity of one sequence of interest to a group of reference sequences, a position is considered to be identical if it is identical to at least one amino acid at a corresponding position in any one or more of the group of reference sequences. With respect to lists of segments, features, or regions, identity can be calculated collectively for all members of such list to arrive an overall percentage identity.

Provided herein are sequences that are at least 60, 65, 70, 75, 80, 82, 85, 87, 88, 89, 90, 91, 92, 93, 94, 95, 96, 97, 98, or 99% identical to sequences disclosed herein.

As used herein, the singular forms "a", "an", and "the" include plural references unless the context clearly dictates otherwise.

All patents, patent applications, scientific publications and other references cited in this specification are hereby incorporated herein for all purposes, and for the disclosure for which they have been cited.

DRAWINGS

FIGS. 1A-1D show a set of graphs depicting the results of SPR experiments determining the binding of the variant serum albumin polypeptides (VSAs) HSA-5, HSA-11, HSA-7, and HSA-13 to human FcRn at pH 5.5 (FIG. 1A), pH 6.0 (FIG. 1B), pH 6.5 (FIG. 1C), and pH 7.4 (FIG. 1D).

FIG. 2 is a table depicting the $K_D$s as determined by ELISA of variant serum albumin polypeptides (VSAs) at pH 5.5.

Figure 4:
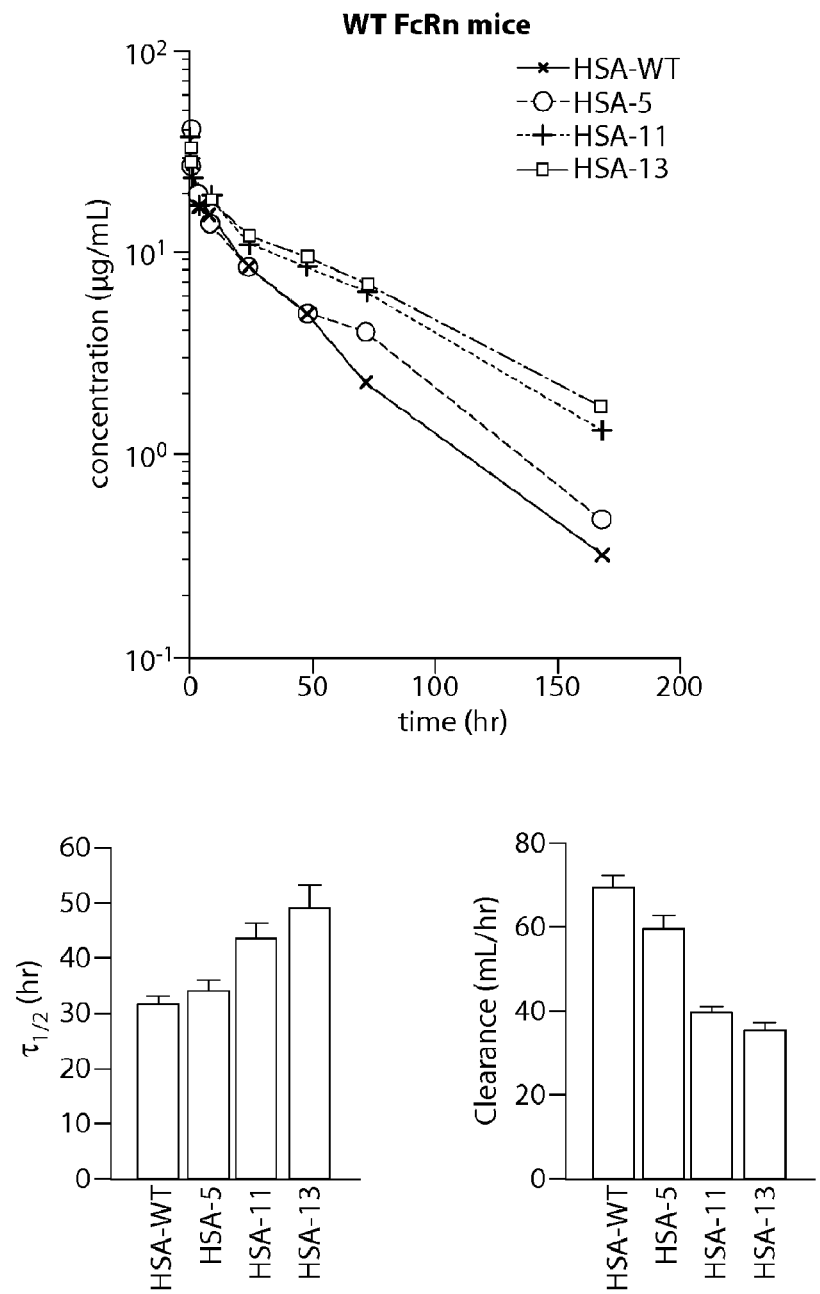

FIG. 4 is s set of graphs depicting the pharmacokinetics of VSAs (HSA-5, HSA-11, and HSA-13) and wild type human serum albumin (wt-HSA) in wild type mice. The left panel shows plasma concentration over time. The right upper panel shows half-life, and the right lower panel shows clearance.

Figure 5:
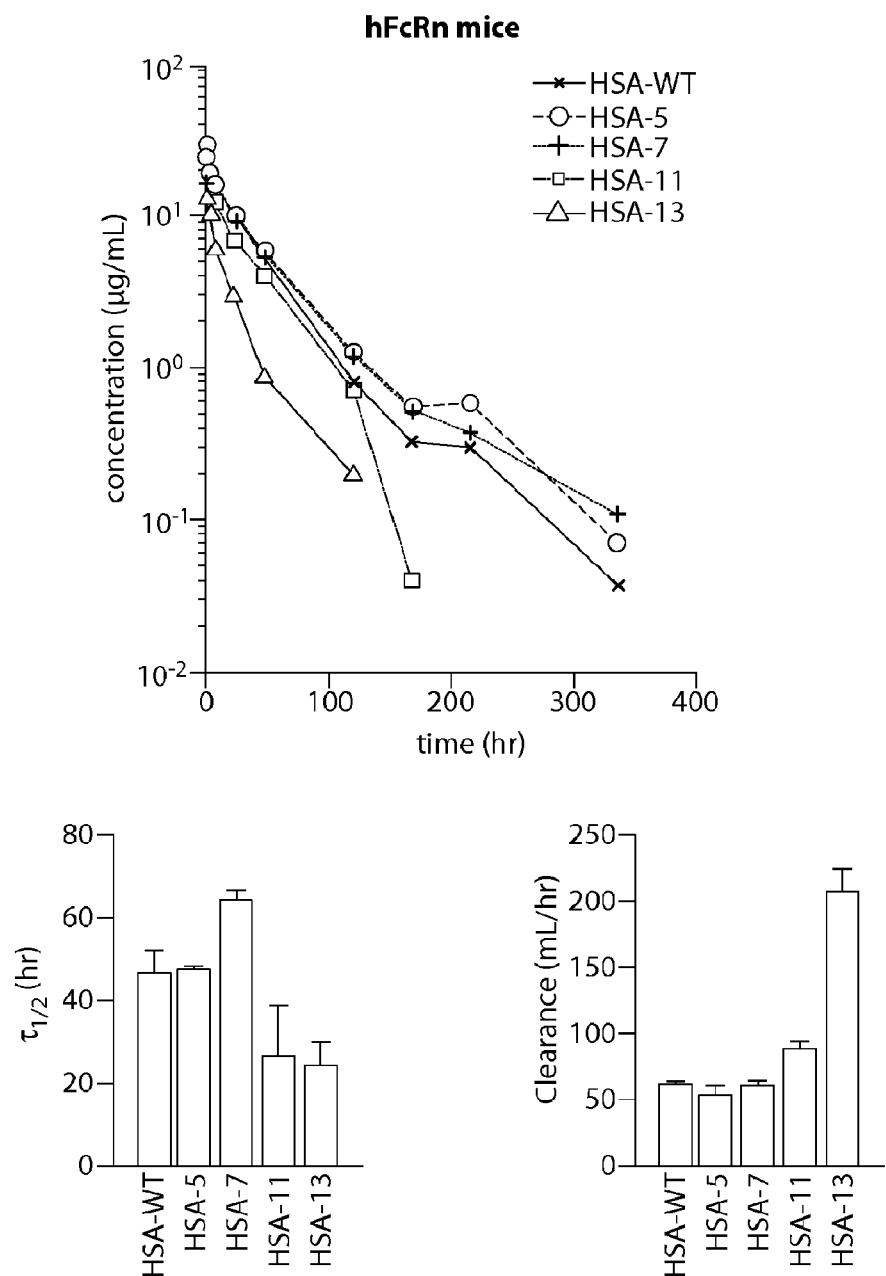

FIG. 5 is s set of graphs that depicting the pharmacokinetics of VSAs (HSA-5, HSA-11, and HSA-13) and wild type HSA in human FcRn transgenic mice. The left panel shows plasma concentration over time. The right upper panel shows half-life, and the right lower panel shows clearance.

FIG. 6 is a table depicting the PK parameters of a wild type HSA (HSA-wt) and a VSA (HSA-7) in a primate.

Figure 7:
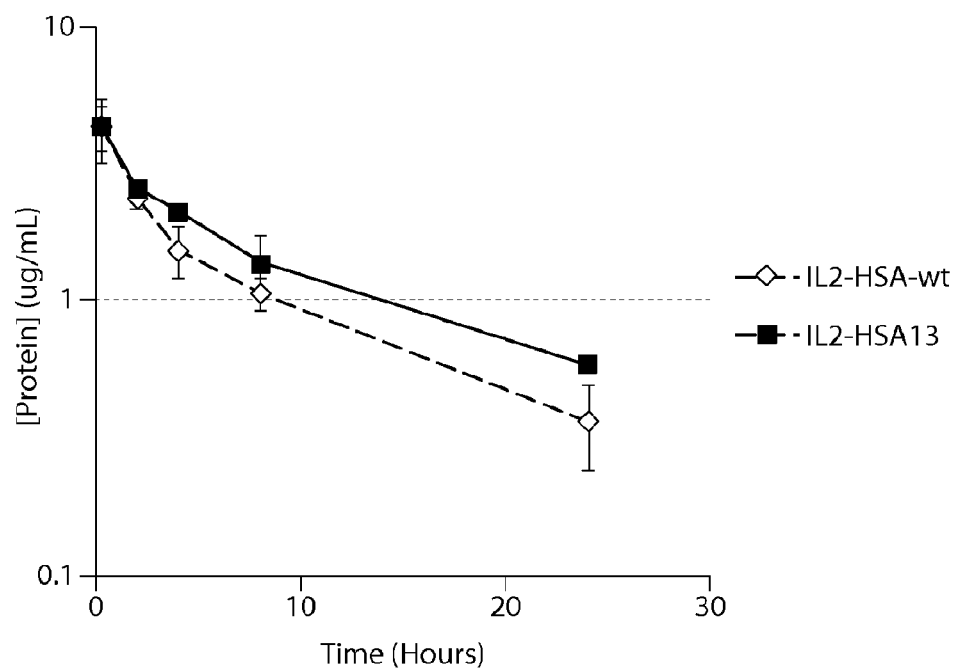

FIG. 7 is a graph and a table depicting the pharmacokinetics of IL-2 fused to wild type HSA and to a VSA (HSA-13) in C57Bl/6J mice.

DETAILED DESCRIPTION

One limitation of certain agents (e.g., therapeutic or diagnostic agents) can be their suboptimal pharmacokinetics (PK), particularly when administered systemically. Relatively short PKs (as assessed, e.g., by plasma half-life of the agents) can mean, for example, that a therapeutic must be administered at a relatively high frequency. The present disclosure provides VSAs that have improved functional properties, e.g., improved pharmacokinetics (e.g., increased half-life, reduced clearance, and/or reduced beta phase clearance). The VSAs can be useful themselves, e.g., for therapeutic or diagnostic uses. The VSAs can be used to improve the functional properties, e.g., the pharmacokinetics, of other agents.

The present disclosure provides variant serum albumin polypeptides (VSAs). As used herein, a variant serum albumin polypeptide (VSA) can refer to a variant of a full length native serum albumin or to a variant of a fragment of a native serum albumin (e.g., a variant of a functional fragment of a native serum albumin). Typically, a VSA that is a variant of a fragment of a native serum albumin has a minimal length that provides functionality (e.g., an ability to bind FcRnat endosomal pH). In some embodiments, the variant comprises or consists of a sequence that is a variant of the domain III sequence of a native serum albumin. In some embodiments, the variant comprises a sequence that is a variant of the domain III sequence of a native human serum albumin sequence. In some embodiments, the affinity of a VSA for an FcRn is increased at an endosomal pH (e.g., pH 5.5 or 6.0) compared to the affinity of wild type albumin corresponding to the VSA. In certain embodiments, the affinity of a VSA for an FcRn is increased at an endosomal pH (e.g., pH 5.5 or 6.0) compared to the affinity of wild type albumin corresponding to the VSA and the affinity of the VSA for FcRn at a neutral pH (e.g., pH 7.0 or 7.4) is the same or less than the affinity of a corresponding wild type albumin for an FcRn. In some cases, Applicants have found that in selecting a VSA that is useful, e.g., as a therapeutic, it is necessary to evaluate the affinity for FcRn at both endosomal and neutral pH, noting that a VSA with the greatest affinity for FcRn at endosomal pH may be unsuitable for use because it also has an increased affinity at a neutral pH.

In some embodiments, a VSA comprises an amino acid substitution or deletion at one or more (e.g., 1, 2, 3, 4, 5, or more) positions disclosed herein, e.g., at the positions that were mutated in the experiments disclosed in the Examples and Figures. In some embodiments, a VSA comprises a substitution described herein, e.g., one or more substitutions of a specific amino acid at a specific position as described herein, e.g., as disclosed in the Examples and Figures.

In some embodiments, a VSA has one or more of the following mutations (amino acid residue numbers defined in accordance with the mature human amino acid sequence of SEQ ID NO:2): V418M; T420A; V424I; N429D; M446V; A449V; T467M; E505(R/K/G); V547A; and A552T, wherein "(X/Z)" means that the amino acid sequence may alternatively comprise amino acid X or amino acid Z at that residue. In certain embodiments, the VSA can include one or more of the following mutations: V418M; T420A; V424I; E505(R/K/G); and V547A.

In some embodiments, a VSA comprises a mutation that is present in a VSA disclosed herein, e.g., a VSA selected from one or more of the following variants described herein: HSA-15, HSA-13, HSA-12, HSA-7, HSA-21, HSA-11, HSA-14, HSA-5, HSA-10, HSA-6, HSA-9, and HSA-18. In some embodiments, a VSA includes each of the mutations that are present in a variant described herein, e.g., a variant selected from HSA-15, HSA-13, HSA-12, HSA-7, HSA-21, HSA-11, HSA-2, HSA-14, HSA-5, HSA-10, HSA-6, HSA-9, and HSA-18. In some embodiments, a VSA has the sequence of HSA-15, HSA-13, HSA-12, HSA-7, HSA-21, HSA-11, HSA-14, HSA-5, HSA-10, HSA-6, HSA-9, or HSA-18.

Typically, the VSAs provided herein have improved functional properties (e.g., higher affinity for FcRn at endosomal pH and/or extended pharmacokinetics, e.g., increased half-life and/or reduced clearance) compared with a corresponding native serum albumin sequence. Such VSAs can be useful for therapeutic or diagnostic applications. For example, VSAs can be useful for treating, or for producing formulations that are useful for treating, conditions for which serum albumin is indicated. A VSA that has improved properties compared with a corresponding native serum albumin sequence has therapeutic advantages. For example, a VSA that has extended PK compared with a corresponding native serum albumin polypeptide can have therapeutic advantages, such as less frequent and/or reduced dosing and/or more consistent delivery levels. A VSA can also be less expensive to administer because fewer doses are required.

Native human serum albumin (HSA) binds to human FcRn at pH 6.0 with an affinity of about 1-10 micromolar, and about 400 micromolar affinity at pH 7.4. The VSAs described herein can have improved binding to FcRn at endosomal pH, e.g., at pH 6.0 compared with a native serum albumin (e.g., a corresponding native serum albumin, e.g., the corresponding full length native serum albumin or fragment thereof of which the VSA is a variant).

In some embodiments, the VSA binds to FcRn with a $K_D$ that is less than a value selected from 2 micromolar, 1.5 micromolar, 1 micromolar, and 0.5 micromolar. In some embodiments, the VSA binds to FcRn with a $K_D$ that is less than a value selected from 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, and 5 nM. The $K_D$ can be determined as described herein or using any method known in the art.

The $K_D$ is pH dependent. In some embodiments, the VSA exhibits improved binding to FcRn at a specified pH, e.g., at pH 5.0, 5.2, 5.5, 5.6, 5.7, 5.8, 5.9, 6.2, 6.0, or 6.2. In some embodiments, the VSA exhibits improved binding to FcRn at an endosomal pH, for example at pH 5.0-6.2, pH 5.0-6.2, pH 5.0-6.0, or pH 5.5-6.0. In some embodiments, the VSA exhibits improved binding to FcRn at pH 5.5 or 6.0. In some embodiments, the VSA binds to FcRn at an endosomal pH, e.g., at pH 5.5 or pH 6.0, with a $K_D$ that is less than a value selected from 2 micromolar, 1.5 micromolar, 1 micromolar, and 0.5 micromolar. In some embodiments, the VSA binds to FcRn at an endosomal pH, e.g., at pH 5.5 or pH 6.0 with a $K_D$ that is less than a value selected from 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, and 5 nM.

In some embodiments, the serum albumin variants have a $K_D$ for FcRn at pH 5.5 that is less than 23 nM. In some embodiments, the serum albumin variants have a $K_D$ for FcRn at pH 5.5 that is less or equal to 75 nM, 50 nM, 25 nM, 15 nM, 10 nM, 5 nM, or 3 nM.

In some embodiments, the VSA binds to FcRn at an endosomal pH, e.g., pH 5.5 or pH 6.0, but does not bind to FcRn at pH 7.4. In some embodiments, the VSA binds to FcRn at an endosomal pH, e.g., pH 5.5 or pH 6.0, and shows reduced binding to FcRn at pH 7.4 compared with its binding to FcRn at pH 5.5 (e.g., the binding to FcRn at pH 7.4 is less than 5%, 10%, 15%, 20%, 25%, 30%, 35%, 40%, 45%, 50%, 55%, or 60% of the level observed at pH 5.5).

In some embodiments, the VSA binds to FcRn at pH 5.5 and shows reduced binding to FcRn at pH 7.4 compared with its binding to FcRn at an endosomal pH, e.g., pH 5.5 or pH 6.0 (e.g., the binding to FcRn at pH 7.4 is less than 1%, 2%, 3%, 4%, 5%, 10%, 15%, 20%, 25%, 30%, 35%, 40%, 45%, 50%, 55%, or 60% of the level observed at pH 5.5), and the VSA has improved pharmacokinetics (e.g., increased plasma half-life and/or reduced clearance, e.g., reduced beta phase clearance) compared with a corresponding native serum albumin.

In some embodiments, the VSA has a decreased $K_D$ for FcRn at an endosomal pH, e.g. pH5.5 or pH 6.0, compared to the $K_D$ of a wild type albumin (e.g., an HSA) at endosomal pH, and has the same or increased $K_D$ for FcRn at a neutral pH, e.g., pH 7.0 or pH 7.4.

The ratio of the $K_D$s of wild type HSA to FcRn at pH 7.4 and 5.5 is 40-400, depending on the report. In some embodiments, the ratio of $K_D$s of the VSA to FcRn at pH 7.4 and 5.5 is greater than for wild type HSA (e.g., a ratio of 500; 1000; 5000; 10,000; 100,000; or 1 million). In some embodiments, the binding of VSA to FcRn is assessed using SPR. In some embodiments, the binding of VSA to FcRn is assessed using ELISA.

In some embodiments, the half life (T½) of the VSA is greater than the T½ of a corresponding native serum albumin. In some embodiments, the T½ of the VSA is increased by 10%, 20%, 30%, 40%, 50%, 60%, 70%, 80%, 90%, or 100% compared with the T½ of a corresponding native serum albumin. In some embodiments, the T½ of the VSA is at least two times, three times, or four times as long as the T½ of a corresponding native serum albumin. In some embodiments, the T½ of the VSA is at least twice as long as the T½ of a corresponding native serum albumin.

Wild type HSA has a half-life (T½) in plasma of about 15-20 days in humans. A variant serum albumin described herein can have a longer serum half-life than a corresponding albumin, e.g., T½ at least about 16, 17, 18, 19, 20, 21, 22, 23, 24, or 25 days. In some embodiments, the VSA. In some embodiments, the VSA has a longer serum T½ in an animal compared to the corresponding wild type VSA, e.g., a VSA has a longer serum T½ in a monkey than the T½ of a human wild type albumin in a monkey.

Wild type HSA (UniProt DB Accession No. P02768; SEQ ID NO:1 below) is a 609 amino acid protein, comprising an 18 amino acid signal peptide; a 6 amino acid propeptide, extending from amino acid 19 to 24; Domain 1, extending from amino acid 25 to 210; Domain 2, extending from amino acid 211 to 403; and Domain 3, extending from amino acid 404 to 601 or amino acid 404 to 609 of Sequence ID No. 1. An exemplary sequence of a human serum albumin (including its leader sequence) is as follows:

[SEQ ID NO: 1]
```
         10          20          30          40
MKWVTFISLL  FLFSSAYSRG  VFRRDAHKSE  VAHRFKDLGE
```

```
        50          60          70          80
ENFKALVLIA  FAQYLQQCPF  EDHVKLVNEV  TEFAKTCVAD 90         100         110         120
ESAENCDKSL  HTLFGDKLCT  VATLRETYGE  MADCCAKQEP 130         140         150         160
ERNECFLQHK  DDNPNLPRLV  RPEVDVMCTA  FHDNEETFLK 170         180         190         200
KYLYEIARRH  PYFYAPELLF  FAKRYKAAFT  ECCQAADKAA 210         220         230         240
CLLPKLDELR  DEGKASSAKQ  RLKCASLQKF  GERAFKAWAV 250         260         270         280
ARLSQRFPKA  EFAEVSKLVT  DLTKVHTECC  HGDLLECADD 290         300         310         320
RADLAKYICE  NQDSISSKLK  ECCEKPLLEK  SHCIAEVEND 330         340         350         360
EMPADLPSLA  ADFVESKDVC  KNYAEAKDVF  LGMFLYEYAR 370         380         390         400
RHPDYSVVLL  LRLAKTYETT  LEKCCAAADP  HECYAKVFDE 410         420         430         440
FKPLVEEPQN  LIKQNCELFE  QLGEYKFQNA  LLVRYTKKVP 450         460         470         480
QVSTPTLVEV  SRNLGKVGSK  CCKHPEAKRM  PCAEDYLSVV 490         500         510         520
LNQLCVLHEK  TPVSDRVTKC  CTESLVNRRP  CFSALEVDET 530         540         550         560
YVPKEFNAET  FTFHADICTL  SEKERQIKKQ  TALVELVKHK 570         580         590         600
PKATKEQLKA  VMDDFAAFVE  KCCKADDKET  CFAEEGKKLV

609
AASQAALGL
```

An exemplary sequence of a human serum albumin (HSA) (in its mature form) is a 585 amino acid polypeptide as follows in SEQ ID NO:2. In some embodiments, the VSAs as described herein comprise variant domain III regions. Typically, such variant domain III regions retain the three-dimensional fold of domain III of serum albumin.

Exemplary variant domain III regions are at least 80% identical to domain III of a naturally occurring serum albumin, e.g., at least 90% identical to the domain III of a human serum albumin (e.g., amino acids 404 to 609 of SEQ ID NO:1 or amino acids 380 to 585 of SEQ ID NO:2 below).

A variant serum albumin polypeptide can have one or more (e.g., 1, 2, 3, 4, 5, or more) substitutions, insertions, or deletions relative to a corresponding native serum albumin. For example, the variant polypeptide can include a domain III with at least one, two, three, four or five substitutions relative to a domain III of HSA.

```
                                    [SEQ ID NO: 2]
        10          20          30          40
DAHKSEVAHR  FKDLGEENFK  ALVLIAFAQY  LQQCPFEDHV 50          60          70          80
KLVNEVTEFA  KTCVADESAE  NCDKSLHTLF  GDKLCTVATL 90         100         110         120
RETYGEMADC  CAKQEPERNE  CFLQHKDDNP  NLPRLVRPEV 130         140         150         160
```
```
       170         180         190         200
DVMCTAFHDN  EETFLKKYLY  EIARRHPYFY  APELLFFAKR 210         220         230         240
YKAAFTECCQ  AADKAACLLP  KLDELRDEGK  ASSAKQRLKC 250         260         270         280
ASLQKFGERA  FKAWAVARLS  QRFPKAEFAE  VSKLVTDLTK 290         300         310         320
VHTECCHGDL  LECADDRADL  AKYICENQDS  ISSKLKECCE 330         340         350         360
KPLLEKSHCI  AEVENDEMPA  DLPSLAADFV  ESKDVCKNYA 370         380         390         400
EAKDVFLGMF  LYEYARRHPD  YSVVLLLRLA  KTYETTLEKC 410         420         430         440
CAAADPHECY  AKVFDEFKPL  VEEPQNLIKQ  NCELFEQLGE 450         460         470         480
YKFQNALLVR  YTKKVPQVST  PTLVEVSRNL  GKVGSKCCKH 490         500         510         520
PEAKRMPCAE  DYLSVVLNQL  CVLHEKTPVS  DRVTKCCTES 530         540         550         560
LVNRRPCFSA  LEVDETYVPK  EFNAETFTFH  ADICTLSEKE 570         580
RQIKKQTALV  ELVKHKPKAT  KEQLKAVMDD  FAAFVEKCCK

ADDKETCFAE  EGKKLVAASQ  AALGL
```

Typically, a VSA is a polypeptide that has a three-dimensional fold that is similar or identical to that of a native serum albumin, e.g., as described in PDB files 1AO6 (Sugio et al. (1999) Protein Eng. June; 12(6):439-46); or 1E78 (Bhattacharya et al., (2000) J. Biol. Chem., 275:38731)); or 1E7H (Bhattacharya et al., (2000) J. Mol. Biol., 303:721).

Exemplary variant serum albumin polypeptides are at least 70% identical to a naturally occurring serum albumin, e.g., at least 75%, 80%, 85%, 90%, or 95% identical to a human serum albumin (e.g., SEQ ID NO:1 above). A variant serum albumin polypeptide can have one or more substitutions, insertions, or deletions. For example, the variant polypeptide can have at least one, two, three, four, or five substitutions relative to HSA.

The sequences of serum albumins from other species, particularly mammalian species are also known. Exemplary sequences include albumin sequences from *Bos taurus* (CAA76847, P02769, CAA41735, 229552, AAF28806, AAF28805, AAF28804, AAA51411); *Sus scrofa* (P08835, CAA30970, AAA30988); *Equus caballus* (AAG40944, P35747, CAA52194); *Ovis aries* (P14639, CAA34903); *Salmo salar* (CAA36643, CAA43187); *Gallus gallus* (P19121, CAA43098); *Felis catus* (P49064, S57632, CAA59279, JC4660); *Canis familiaris* (P49822, 529749, CAB64867). Variations, e.g., substitutions described herein in HSA, can also be introduced at corresponding positions into serum albumins from other species, e.g., into mammalian serum albumins, including, e.g., bovine serum albumin.

Serum albumin can be divided into at least three domains, termed Domain I, Domain II, and Domain III. A serum albumin protein useful in the present invention typically includes at least a domain III, and can also include domain I and domain II. Exemplary domains I, II, and III can have at least 60, 65, 70, 75, 80, 85, 90, 95% identity to respective domains from a mammalian serum albumin. In some embodiments, the variant serum albumin polypeptide of the present invention comprises domain III of human HSA, that is, amino acids 404 to 601 or 404 to 609 of SEQ ID NO:1, or amino acids 380 to 585 of SEQ ID NO:2, into which at least one, two, three, four, or five substitutions have been engineered relative to domain III of HSA.

In some embodiments, a residue that is within less than 7 angstroms of position H464 is substituted with another amino acid. For example, the residue is amino acid 415, 418, 458, 459, 460, 461, 462, 463, 465, 466, 467, 468, 469, 470, 471, 472, 473, 474, 475, or 477. In some embodiments, a residue that is within less than 7 angstroms of position H510 is substituted with another amino acid. For example, the residue is amino acid 508, 509, 511, 512, 513, 514, 554, 555, 559, 564, 565, 568, or 569. In some embodiments, a residue that is within less than 7 angstroms of position H535 is substituted with another amino acid. For example, the residue is amino acid 412, 497, 498, 499, 500, 501, 502, 503, 507, 529, 530, 531, 532, 533, 534, 536, 537, 538, 580, or 583.

In some embodiments, residue V418 is altered, e.g., to a residue other than valine, e.g., to an hydrophobic residue such as methionine. In some embodiments, a residue that is within less than 7 angstroms of position V418 is substituted with another amino acid. For example, the residue is amino acid 411, 412, 415, 416, 417, 419, 420, 421, 422, 423, 424, 426, 460, 464, 469, 470, 473, 497, 530, or 534.

In some embodiments, residue T420 is altered, e.g., to a residue other than threonine, e.g., to an uncharged residue, e.g., a small uncharged residue such as alanine or glycine. In some embodiments, a residue that is within less than 7 angstroms of position T420 is substituted with another amino acid. For example, the residue is amino acid 408, 412, 416, 417, 418, 419, 421, 422, 423, 424, 425, 500, 526, 527, 528, 529, 530, 531, or 534.

In some embodiments, residue V424 is altered, e.g., to a residue other than valine, e.g., to an uncharged residue, e.g., to isoleucine. In some embodiments, a residue that is within less than 7 angstroms of position V424 is substituted with another amino acid. For example, the residue is amino acid 404, 408, 412, 418, 419, 420, 421, 422, 423, 425, 426, 427, 428, 429, 430, 522, 523, 524, 526, 527, 528, or 530.

In some embodiments, residue E505 is altered, e.g., to a residue other than glutamic acid, e.g., to an uncharged residue, e.g., a small uncharged residue such as alanine or glycine, or to a positively charged residue, e.g. lysine or arginine. In some embodiments, a residue that is within less than 7 angstroms of position E505 is substituted with another amino acid. For example, the residue is amino acid 502, 503, 504, 506, 507, 508, or 509.

In some embodiments, residue V547 is altered, e.g., to a residue other than valine, e.g., to an uncharged residue, e.g., a small uncharged residue such as alanine or glycine. In some embodiments, a residue that is within less than 7 angstroms of position V547 is substituted with another amino acid. For example, the residue is amino acid 529, 532, 542, 543, 544, 545, 546, 548, 549, 550, 551, or 552.

Variant serum albumin polypeptides can be incorporated into a fusion protein, with the N- or C-terminus thereof fused to the N- or C-terminus of a diagnostic or therapeutic protein, or variant thereof. In certain embodiments, the variant serum albumin polypeptide and the diagnostic or therapeutic protein are joined through a linker moiety, such as a peptide linker. Linkers useful in the present invention are described in greater detail further herein.

Therapeutic Uses of VSAs

A VSA can be used as a therapeutic, e.g., in uses for which albumin such as human albumin is typically used. For such uses, a VSA as described herein can have the advantage of extended PK, which can enable less frequent and/or reduced dosing for albumin replacement or supplementation. Such uses include, for example, hypovolemia, hypoalbuminemia, burns, adult respiratory distress syndrome, nephrosis, and hemolytic disease of the newborn. Hypoalbuminemia can result from, for example, inadequate production of albumin (e.g., due to malnutrition, burns, major injury, or infection), excessive catabolism of albumin (e.g., due to burn, major injury such as cardiopulmonary bypass surgery, or pancreatitis), loss through bodily fluids (e.g., hemorrhage, excessive renal excretion, or burn exudates), deleterious distribution of albumin within the body (e.g., after or during surgery or in certain inflammatory conditions). Typically, for such uses, a VSA for such uses is administered by injection or iv in a solution that is from 5%-50% VSA (w/v), for example, 10%-40%, 15%-30%, 20%-25%, 20%, or 25%. Typically, administration is sufficient to produce a total albumin plus VSA concentration in a treated subject's serum that is 3.4-5.4 grams per deciliter (g/dL). Methods of assaying albumin concentration are well known in the art and can generally be used to assay total albumin plus VSA concentration.

Also provided herein is a VSA, or a pharmaceutical composition comprising a VSA, for use in therapy. Also included is a VSA, or a pharmaceutica composition comprising a VSA, for use in the treatment of a disease, e.g., a disease or condition for which albumin is indicated. Other embodiments include the use of a VSA, or a pharmaceutical composition comprising a VSA, for the manufacture of a medicament for the treatment of a disease.

Uses of VSAs in Association with Other Agents

VSAs can also be used in association with other agents, e.g., therapeutic or diagnostic agents, to confer functional advantages, e.g., advantages of VSAs as described herein. The agent can be, e.g., any agent that is useful in the diagnosis or therapy of a disease or disorder, e.g., a disease or disorder that affects a human or a non-human animal.

Advantages of VSAs include, e.g., lack of Fc effector function, high solubility, potential for high expression, low immunogenicity, and ability to be fused to another moiety at both termini to generate bivalent, bispecific, or bifunctional molecules.

Disclosed herein are VSAs with improved binding to an FcRn at endosomal pH, thereby potentiating the ability of the VSA and an agent associated with that VSA to have improved PK.

A VSA that has an extended PK can be associated with an agent (e.g., a therapeutic or diagnostic agent) to extend the PK of the agent. The extended PK can have advantages; for example, the agent can be administered less frequently and/or at reduced concentrations and/or more consistent delivery levels of the agent can be achieved.

In some embodiments, associating a VSA with an agent improves the functional properties of the agent. In some embodiments, the dosage and/or frequency at which the agent is effective for producing a particular effect (e.g., a desired therapeutic effect) is reduced when the agent is used in association with the VSA. In some embodiments, associating a VSA with an agent improves the pharmacokinetic properties of the agent (e.g., increases its half-life and/or reduces its clearance). Any relevant pharmacokinetic parameters that are known in the art can be used to assess pharmacokinetic properties. The pharmacokinetics of a VSA or a VSA associated with an agent can be measured in any relevant biological sample, e.g., in blood, plasma, or serum.

In some embodiments, associating a VSA with an agent improves the half life (T½) of the agent. In some embodiments, the T½ of the agent is increased by 10%, 20%, 30%, 40%, 50%, 60%, 70%, 80%, 90%, or 100%. In some embodiments, the T½ is at least two times, three times, or four times as long as the T½ of the agent when it is not associated with the VSA. In some embodiments, the T½ of the VSA is at least twice as long as the T½ of the agent when it is not associated with the VSA.

In some embodiments, the dose at which the agent is effective for producing a particular effect (e.g., a desired therapeutic effect) is reduced when the agent is associated with the VSA. In some embodiments, the effective dose is reduced to 80%, 70%, 60%, 50%, 40%, 30%, 20%, or 10% of the dose that is required when the agent is not associated with the VSA.

In some embodiments, the frequency of dosing of the agent that is effective for producing a particular effect (e.g., a desired therapeutic effect) is reduced when the agent is associated with the VSA. In some embodiments, the frequency of dosing at which the agent is effective when it is associated with the VSA is decreased by 10%, 20%, 30%, 40%, 50%, or more compared with the frequency at which the agent is effective when it is not associated with the VSA.

In some embodiments, the frequency of dosing at which the agent is effective when it is associated with the VSA is decreased by at least 2 hours, 4 hours, 6 hours, 8 hours, 12 hours, 1 day, 2 days, 3 days, 4 days, 5 days, 6 days, 7 days, 10 days, 2 weeks, 3 weeks, or 4 weeks compared with the frequency at which the agent is effective when it is not associated with the VSA.

The improvement in the properties of the agent can be assessed relative to any appropriate control. For example, the improvement in the properties of an agent that is associated with a VSA can be assessed by comparing the properties of the agent that is associated with the VSA with the properties of the agent when it is not in an association with the VSA. Alternatively, the improvement in the properties of an agent that is associated with a VSA can be assessed by comparing the properties of the agent that is associated with the VSA with the properties of the agent when it is in an association with a corresponding native serum albumin polypeptide.

Also provided herein is a VSA, a VSA in association with another agent, a pharmaceutical composition comprising a VSA, or a pharmaceutical composition comprising a VSA in association with another agent, for use in therapy or for use in the treatment of a disease, e.g., a disease or condition described herein or described in U.S. Pat. Nos. 5,766,883, 5,875,969, U.S. Patent Publication No. US 2002/0151011, or International Publication No. WO 2011/103076, the entire contents of each of which are hereby incorporated herein by reference. Other embodiments include the use of a VSA, or a pharmaceutical composition comprising a VSA, a VSA in association with another agent, a pharmaceutical composition comprising a VSA, or a pharmaceutical composition comprising a VSA in association with another agent, for the manufacture of a medicament for the treatment of a disease.

The agent can be another protein, e.g., a heterologous protein. In some embodiments, the agent is a diagnostic agent. In some embodiments, the agent is a therapeutic agent. For example, a protein that comprises a VSA can be used to extend the PK of a systemically administered therapeutic agent. The heterologous protein can be, for example, a therapeutic protein or a diagnostic protein. The serum albumin polypeptide with altered FcRn binding properties or a domain thereof (e.g., domain III) can be associated with (e.g., attached covalently to) the therapeutic protein, or to an active fragment or variant of the therapeutic protein. The variant serum albumin or a domain thereof can be in the same polypeptide chain as is at least a component of the therapeutic protein.

A variant serum albumin (VSA) can be associated with another agent, e.g., a therapeutic agent or a diagnostic agent. The other agent (e.g., therapeutic agent) can be an entire protein (e.g., an entire therapeutic protein) or a biologically active fragment thereof. The activity of the agent (e.g., therapeutic agent) can be evaluated in an appropriate in vitro or in vivo assay for the agent's activity. In general, the activity of the agent fused to a VSA is not reduced, for example, by more than 50%, by more than 40%, by more than 30%, by more than 20%, by more than 10%, by more than 5%, or by more than 1% compared with the activity of the agent when it is not in association with the agent. Examples of methods for assessing the activity of certain agents are provided herein.

In some embodiments, the VSA is attached to the agent by one or more covalent bonds to form a variant serum albumin fusion molecule. Any agent that can be linked to a VSA described herein can be used as the agent in a variant serum albumin fusion molecule. The agent can be a therapeutic or diagnostic agent. For example, the agent can be any polypeptide or drug known to one of skill in the art.

In some embodiments, an agent (e.g., therapeutic or diagnostic agent) is stably associated with a VSA, but the agent is not fused to the VSA. In such embodiments, the agent can be associated with the VSA by any means known in the art. For example, the agent can be conjugated to a moiety that is capable of binding the VSA. In some embodiments, the moiety is an albumin binding protein. In some embodiments the moiety is a fatty acid. In some embodiments, the agent is non-covalently bound to the VSA, generally via the affinity of the VSA for small lipophilic moieties. In embodiments wherein the agent is not fused to the VSA, the agent can be administered before, after, or concurrently with the VSA. In some embodiments, the agent is administered concurrently with the VSA. In some embodiments, the agent is administered at the same frequency as is the VSA. In some embodiments, the agent is administered more or less frequently than the VSA.

In some embodiments, the agent is a polypeptide consisting of at least 5, for example, at least 10, at least 20, at least 30, at least 40, at least 50, at least 60, at least 70, at least 80, at least 90 or at least 100 amino acid residues. The agent can be derived from any protein for which an improved property is desired, e.g., an increase in serum levels and/or serum half-life of the agent; or a modified tissue distribution and/or tissue-targeting of the agent.

In some embodiments, the agent is a cytokine or a variant thereof. Generally, a cytokine is a protein released by one cell population that acts on another cell as an intercellular mediator. Examples of such cytokines include lymphokines, monokines, and traditional polypeptide hormones. Specific examples include: interleukins (ILs) such as IL-1 (IL-1α and IL1β), IL-2, IL-3, IL-4, IL-5, IL-6, IL-7, IL-8, IL-9, IL-10, IL-11, IL-12; IL-15, IL-18, and IL-37; a tumor necrosis factor such as TNF-alpha or TNF-beta; growth hormone such as human growth hormone (HGH); somatotropin; somatrem; N-methionyl human growth hormone, and bovine growth hormone; parathyroid hormone; thyroxine; insulin; proinsulin; insulin-like growth factors, such as insulin-like growth factors-1, -2, and -3 (IGF-1; IGF-2; IGF-3); proglucagon; glucagon and glucagon-like peptides, such as glucagon-like peptide-1 and -2 (GLP-1 and GLP-2); exendins, such as exendin-4; gastric inhibitory polypeptide (GIP); secretin; pancreatic polypeptide (PP); nicotinamide phosphoribosyltransferase (also known as visfatin); leptin; neuropeptide Y (NPY); interleukin IL-1Ra, including (N140Q); ghrelin; orexin; adiponectin; retinol-binding protein-4 (RBP-4); adropin; relaxin; prorelaxin; neurogenic differentiation factor 1 (NeuroD1); glicentin and glicentin-related peptide; cholecystokinin (previously known as pancreozymin); glycoprotein hormones such as follicle stimulating hormone (FSH), thyroid stimulating hormone (TSH), and luteinizing hormone (LH); hepatic growth factor; fibroblast growth factors (FGF) such as FGF-19, FGF-21 and FGF-23; prolactin; placental lactogen; tumor necrosis factor-alpha and -beta; mullerian-inhibiting substance; gonadotropin-associated peptide; luteinizing-hormone-releasing hormone (LHRH); inhibin; activin; vascular endothelial growth factor; integrin; thrombopoietin (TPO); growth factors (e.g., platelet-derived growth factor, PDGF and its receptor, EGF and its receptor, nerve growth factors, such as NGF-beta and its receptor, and KGF, such as palifermin, and its receptor); platelet-growth factor (PGF); transforming growth factors (TGFs) such as TGF-alpha and TGF-beta; osteoinductive and growth and differentiation factors, such as osteocalcin, BMP-4, BMP-6 and BMP-7; interferons such as interferon-alpha, beta, and -gamma, including interferon-alpha2B; colony stimulating factors (CSFs) such as macrophage-CSF (M-CSF); granulocyte-macrophage-CSF (GM-CSF); and granulocyte-CSF (G-CSF); erythropoietin (EPO); darbepoeitin alfa; tissue plasminogen activator (TPA) or alteplase; tenecteplase; dornase alfa; entanercept; calcitonin, oxyntomodulin; glucocerebrosidase; arginine deiminase, Arg-vasopressin, natriuretic peptides, including A-type natriuretic peptide; B-type natriuretic peptide, C-type natriuretic peptide and Dendroapsis natriuretic peptide (DNP); gonadotropin-releasing hormone (GnRH); endostatin; angiostatin, including (N211Q); Kiss-1; hepcidin; oxytocin; pancreatic polypeptide; calcitonin gene-related protein (CGRP); parathyroid hormone (PTH); adrenomedulin; delta-opioids; K-opioids; mu-opioids; deltorphins; enkephalins; dynorphins; endorphins; CD276, including (B7-H3); ephrin-B1; tweak-R, cyanovirin, including cyranovirin-N; gp41 peptides; 5-helix protein; prosaptide; apo-lipoprotein A1; BDNF; brain-derived neural protein; CNTF (Axokine®); Antithrombin III; FVIII A1 domain; Kringle-5; Apo A-1 Milano; Kunitz domains; vWF A1 domain; Peptide YY, including PYY1-36 and PYY3-36; urate oxidase; and other polypeptide factors including LIF and kit ligand (KL).

In one embodiment, the agent is BMP peptide analogue (e.g., THR-184, Thrasos Therapeutics, Inc.).

In one embodiment, the agent is GLP-2.

In some embodiments, the therapeutic protein is a monomeric protein (such as a monomeric cytokine, e.g., an IL-1Ra, or an scFv). Albumin fusion proteins are known in the art; the variant serum albumin polypeptides with altered FcRn binding properties, described herein, can be used in place of serum albumin and linked to a therapeutic agent to form fusion proteins with improved properties, such as increased half-life.

Examples of other polypeptides useful as the active agent include, but are not limited to, various types of antibodies, antibody fragments, such as antigen binding domains (e.g., scFv, Fv, Fab, F(ab)2, domain antibodies, and the like); Surrobodies, Adnectins™, anti-calin, affibody, or fragments of the foregoing. Also useful as active agents are receptor antagonists, such as IL-1Ra (e.g., anakinra), cell adhesion molecules (e.g., cadherins, such as cadherin-11, CTLA4, CD2, and CD28); anti-angiogenic factors such as endostatin; receptors, as well as soluble fragments of tissue-bound receptors.

The agent, e.g., therapeutic moiety included in a fusion protein as described herein, can also be a therapeutic moiety such as a cytotoxin (e.g., a cytostatic or cytocidal agent), a non-peptide therapeutic agent or a radioactive element (e.g., alpha-emitters, gamma-emitters, etc.). Examples of cytostatic or cytocidal agents include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Non-peptide therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and antimitotic agents (e.g., vincristine and vinblastine). The present invention also encompasses fusing the variant serum albumin (VSA) moiety to an active agent that is a diagnostic agent. The VSA-diagnostic molecule of the invention can be used diagnostically to, for example, monitor the development or progression of a disease, disorder or infection as part of a clinical testing procedure to, e.g., determine the efficacy of a given 5 treatment regimen. Detection can be facilitated by coupling the pharmacologic enhancing molecule to a detectable substance. Examples of detectable substances include enzymes, prosthetic groups, fluorescent materials, luminescent materials, bioluminescent materials, radioactive materials, positron emitting metals, and nonradioactive paramagnetic metal ions. The detectable substance can be coupled or conjugated either directly to the antibody or indirectly, through an intermediate (such as, for example, a linker known in the art) using techniques known in the art. See, for example, U.S. Pat. No. 4,741,900 for metal ions that can be conjugated to antibodies for use as a diagnostic according to the methods and compositions described herein. Examples of suitable enzymes include, e.g., horseradish peroxidase, alkaline phosphatase, O-galactosidase, or acetylcholinesterase; examples of suitable prosthetic groups include, e.g., complexes including, e.g. streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include, e.g., $^{125}$I, $^{131}$I, $^{111}$In or 99mTc. See, for example, Plumridge et al., WO2011/051489; Lubman et al.; WO2010/141329.

The nucleotide and amino acid sequences and structures for the above molecules that are useful as, or in preparing the active moiety to be fused to the variant serum albumin moiety in the present invention are known, and all of the publications and websites described as providing such information, such as Genbank, the protein database and Uniprot (www.ncbi.nlm.nih.gov/genbank; www.pdb.org; and www.uniprot.org, respectively), are incorporated herein by reference for this purpose. Non-limiting examples of therapeutic proteins that can be used in preparing some of the embodiments of the present invention are described in further detail below.

Glucagon-Like Peptide 1 (GLP-1).

In one embodiment, the therapeutic agent includes a GLP-1 or a biologically active variant or fragment thereof. GLP-1 is a 37 amino acid peptide that is formed from cleavage of glucagon, secreted by the L-cells of the intestine in response to food ingestion (Uniprot accession number: P01275). GLP-1 can stimulate insulin secretion, causing glucose uptake by cells and decreased serum glucose levels (e.g., Mojsov, Int. J. Peptide Protein Research, 40:333-343 (1992)). GLP-1 can be cleaved to produce a biologically active peptide GLP-1(7-37)OH. In addition, numerous GLP-1 analogs and derivatives are known and include, e.g., exendins which are peptides found in Gila monster venom. Exendins have sequence homology to native GLP-1 and can bind the GLP-1 receptor and initiate the signal transduction cascade of GLP-1(7-37)OH. GLP-1 compounds can have one or more of the following biological properties: ability to stimulate insulin release, lower glucagon secretion, inhibit gastric emptying, and enhance glucose utilization. (e.g., Nauck et al., Diabetologia 36:741-744 (1993); Gutniak et al., New England J. of Med. 326:1316-1322 (1992); Nauck et al., J. Clin. Invest. 91:301-307 (1993)). A therapeutic agent including GLP-1, GLP-1(7-37)OH, an exendin, or biologically active variants or fragments thereof can be used for treating a diabetic disorder, e.g., non-insulin dependent diabetes mellitus (NIDDM).

The amino acid sequence of human GLP-1 is as follows:

[SEQ ID NO: 3]
HDEFERHAEG TFTSDVSSYL EGQAAKEFIA WLVKGRG

Advantages of using a VSA in association with a GLP-1 (e.g., using a VSA-GLP-1 fusion protein) include, e.g., extending the PK of the GLP-1. The extended PK can have advantages; for example, the GLP-1 can be administered less frequently and/or at reduced concentrations and/or more consistent delivery levels of the GLP-1 can be achieved.

Insulin.

In one embodiment, the therapeutic agent is an insulin. The insulin can be a full length insulin polypeptide or a biologically active variant or fragment thereof. For example, the insulin can be a glucose sensitive molecule that includes an insulin receptor agonist. An exemplary insulin polypeptide (110 amino acids) has the sequence:

[SEQ ID NO: 4]
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN.

The B-chain (1-30 or FVNQHL CGSHLVEALY LVCGERGFFY TPKT) [SEQ ID NO:5] is present at amino acids 25-54. The A-chain (1-21 or G IVEQCCTSIC SLYQLENYCN) [SEQ ID NO:6] is present at amino acids 90-110. (See, Uniprot accession no. P01308). The C-peptide (RREAED LQVGQVELGG GPGAGSLQPL ALEGSLQKR) [SEQ ID NO:7] which links the B-chain and A-chain is present at amino acids 55-89. Therapeutic proteins as disclosed herein can include the B-chain and A-chain of insulin, linked by the C-peptide of insulin or another natural or artificial sequence, such as a peptide linker. A number of adipose and muscle related cell lines can be used to test for glucose uptake/transport activity in the absence or presence of a combination of any one or more of the therapeutic drugs listed for the treatment of diabetes mellitus. In particular, the 3T3-L1 murine fibroblast cells and the L6 murine skeletal muscle cells can be differentiated into 3T3-L1 adipocytes and into myotubes, respectively, to serve as appropriate in vitro models for the [$^3$H]-2-deoxyglucose uptake assay (Urso et al., J Biol Chem, 274:30864-73 (1999); Wang et al., J Mol Endocrinol, 19:241-8 (1997); Haspel et al., J Membr Biol, 169:45-53 (1999); Tsakiridis et al., Endocrinology, 136:4315-22 (1995)). Female NOD (non-obese diabetic) mice are characterized by displaying IDDM with a course which is similar to that found in humans, although the disease is more pronounced in female than male NOD mice.

Advantages of using a VSA in association with an insulin (e.g., using a VSA-insulin fusion protein) include, e.g., extending the PK of the insulin. The extended PK can have advantages; for example, the insulin can be administered less frequently and/or at reduced concentrations and/or more consistent delivery levels of the insulin can be achieved.

Fibroblast Growth Factor 19 (FGF-19).

In one embodiment, the therapeutic agent is an FGF-19 (e.g., human FGF-19) or a biologically active variant or fragment thereof. Human FGF-19 is a 216 amino acid protein, including a 24 amino acid N-terminal signal peptide. An exemplary FGF-19 peptide sequence is the sequence of human FGF-19 (Uniprot accession number: O95750):

[SEQ ID NO: 8]
MRSGCVVVHV WILAGLWLAV AGRPLAFSDA GPHVHYGWGD

PIRLRHLYTS GPHGLSSCFL RIRADGVVDC ARGQSAHSLL

EIKAVALRTV AIKGVHSVRY LCMGADGKMQ GLLQYSEEDC

AFEEEIRPDG YNVYRSEKHR LPVSLSSAKQ RQLYKNRGFL

PLSHFLPMLP MVPEEPEDLR GHLESDMFSS PLETDSMDPF

GLVTGLEAVR SPSFEK

FGF-19 is active in the suppression of bile acid biosynthesis and stimulates glucose uptake in adipocytes. Holt et al., Genes Dev. 17:1581-91 (2003). FGF-19 can be used for treatment of dietary and leptin-deficient diabetes. Fu et al., Endocrinology, 145:2594-603 (2004).

Advantages of using a VSA in association with FGF-19 (e.g., using a VSA-FGF-19 fusion protein) include, e.g., extending the PK of the FGF-19. The extended PK can have advantages; for example, the FGF-19 can be administered less frequently and/or at reduced concentrations and/or more consistent delivery levels of the FGF-19 can be achieved.

Fibroblast Growth Factor 21 (FGF-21).

In one embodiment, the therapeutic agent is an FGF-21 (e.g., human FGF-21) or a biologically active variant or fragment thereof. Human FGF-21 is a 209 amino acid protein, including a 28 amino acid N-terminal signal peptide. An exemplary FGF-21 peptide sequence is the sequence of human FGF-21 (Uniprot accession number: Q9NSA1):

[SEQ ID NO: 9]
MDSDETGFEH SGLWVSVLAG LLLGACQAHP IPDSSPLLQF

GGQVRQRYLY TDDAQQTEAH LEIREDGTVG GAADQSPESL

-continued

```
LQLKALKPGV IQILGVKTSR FLCQRPDGAL YGSLHFDPEA

CSFRELLLED GYNVYQSEAH GLPLHLPGNK SPHRDPAPRG

PARFLPLPGL PPALPEPPGI LAPQPPDVGS SDPLSMVGPS

QGRSPSYAS
```

FGF-21 stimulates glucose uptake in differentiated adipocytes via the induction of the insulin-independent glucose transporter GLUT1. In ob/ob mice, FGF-21 has been demonstrated to have durable glucose control and triglyceride lowering effects with minimal adverse side effects. Kharitonenkov et al., J. Clin. Invest. 115:1627-35 (2005). Accordingly, FGF-21 is useful in treatment of diabetes.

Advantages of using a VSA in association with FGF-21 (e.g., using a VSA-FGF-21 fusion protein) include, e.g., extending the PK of the FGF-21. The extended PK can have advantages; for example, the FGF-21 can be administered less frequently and/or at reduced concentrations and/or more consistent delivery levels of the FGF-21 can be achieved.

Fibroblast Growth Factor 23 (FGF-23).

In one embodiment, the therapeutic agent is an FGF-23 (e.g., human FGF-23) or a biologically active variant or fragment thereof. Human FGF-23 is a 251 amino acid protein, including a 24 amino acid N-terminal signal peptide. FGF-23 is cleaved by protein convertases into an N-terminal peptide of approximately 155 amino acids (amino acid 25-179); and a C-terminal peptide of approximately 72 amino acids (amino acids 180-251). An exemplary FGF-23 peptide sequence is the sequence of human FGF-23 (Uniprot accession number: Q9GZV9):

```
                                       [SEQ ID NO: 10]
MLGARLRLWV CALCSVCSMS VLRAYPNASP LLGSSWGGLI

HLYTATARNS YHLQIHKNGH VDGAPHQTIY SALMIRSEDA

GFVVITGVMS RRYLCMDFRG NIFGSHYFDP ENCRFQHQTL

ENGYDVYHSP QYHFLVSLGR AKRAFLPGMN PPPYSQFLSR

RNEIPLIHFN TPIPRRHTRS AEDDSERDPL NVLKPRARMT

PAPASCSQEL PSAEDNSPMA SDPLGVVRGG RVNTHAGGTG

PEGCRPFAKF I
```

FGF-23 is involved in regulating phosphate homeostasis. FGF-23 has been shown to inhibit renal tubule phosphate transport (Bowe et al., Biochem. Biophys. Res. Commun., 284:977-81 (2001)); to regulate vitamin D metabolism (Shimada et al., J. Bone Miner. Res., 19:429-35 (2004)); and to negatively regulate osteoblast differentiation and matrix mineralization (Wang et al., J. Bone Miner. Res., 23:939-48 (2008)). Accordingly, FGF-23 can be used in treatment of autosomal dominant hypophosphatemic rickets (ADHR) and tumor-induced osteomalacia (Riminucci et al., J. Clin. Invest., 112:683-92 (2003)).

Advantages of using a VSA in association with FGF-23 (e.g., using a VSA-FGF-23 fusion protein) include, e.g., extending the PK of the FGF-23. The extended PK can have advantages; for example, the FGF-23 can be administered less frequently and/or at reduced concentrations and/or more consistent delivery levels of the FGF-23 can be achieved.

Interleukin-2 (IL-2).

In one embodiment, the therapeutic agent is an IL-2 (e.g., human IL-2) or a biologically active variant or fragment thereof. Human IL-2 is a 153 amino acid protein, including a 20 amino acid N-terminal signal peptide. An exemplary IL-2 peptide sequence is the sequence of human IL-2 (Uniprot accession number: P60568):

```
                                       [SEQ ID NO: 11]
MYRMQLLSCI ALSLALVTNS APTSSSTKKT QLQLEHLLLD

LQMILNGINN YKNPKLTRML TFKFYMPKKA TELKHLQCLE

EELKPLEEVL NLAQSKNFHL RPRDLISNIN VIVLELKGSE

TTFMCEYADE TATIVEFLNR WITFCQSIIS TLT
```

IL-2 can induce proliferation of antigen-activated T cells and stimulates natural killer (NK) cells, as well as stimulates proliferation of regulatory T cells (Tregs). The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD122 in humans) and p64 (IL-2Rγ, the gamma subunit, also known as CD132 in humans). IL-2-derived polypeptides can be used in cancer immunotherapies and to deliver therapeutic agents to CD25-positive cells in vivo or in cell culture. For example, Proleukin® is an approved biologic that contains IL-2. Exemplary agonists are described by Rao et al., Protein Engineering 16:1081-1087 (2003) and Rao et al., Biochemistry 44:10696-701 (2005), and in US Patent Application Publication 2005/0142106; see also U.S. Pat. Nos. 7,569,215 and 7,951,360. The therapeutic agent can also further include an IL-2 binding fragment of CD25, e.g., the sushi domain of IL-2Rα. The IL-2 binding fragment of CD25 can be covalently linked to the biologically active portion of IL-2 or can be non-covalently linked. Exemplary IL-2 antagonists that bind CD25 but do not activate the IL-2 receptor are described in US 2011/0091412. The IL-2 antagonists can be used to specifically target T regulatory cells and/or specifically inhibit T regulatory cell function. The ability of low-dose IL-2 to reduce inflammation and/or immune response may be particularly surprising in light of previous publications advocating low doses of IL-2 for stimulation of immune response. See, U.S. Pat. No. 6,509,313. Low-dose IL-2 can be used to specifically induce Treg proliferation and promote an anti-inflammatory state. In particular embodiments, low-dose IL-2 can be administered subcutaneously, for example using a self-administered pen or cartridge device, such as is used with other self-administered peptide biotherapeutic drugs, such as long-acting insulin. Particular indications for which low-dose IL-2 can be appropriate include, for example, graft-vs-host-disease; for example, in connection with bone marrow transplantation. Administration of low-dose IL-2 can be advantageous in reducing the need for pre-graft conditioning and/or post-graft treatment with immunosuppressant drugs. Ferrara et al., Biology of Blood and Marrow Transplantation, 5:347-56 (1999). Additional advantages can include avoiding the adverse effects of short-term, high dose IL-2. See Sykes et al., Blood, 83:2560-69 (1994).

Advantages of using a VSA in association with IL-2 (e.g., using a VSA-IL-2 fusion protein) include, e.g., extending the PK of the IL-2. The extended PK can have advantages; for example, the IL-2 can be administered less frequently and/or at reduced concentrations and/or more consistent delivery levels of the IL-2 can be achieved.

Interleukin-15 (IL-15).

In one embodiment, the therapeutic agent is an IL-15 (e.g., human IL-15) or a biologically active variant or fragment thereof. Human IL-15 is a 162 amino acid protein, including a 29 amino acid N-terminal signal peptide. An exemplary IL-15 peptide sequence is the sequence of human IL-15 (Uniprot accession number: P40933):

```
                                            [SEQ ID NO: 12]
    MRISKPHLRS ISIQCYLCLL LNSHFLTEAG IHVFILGCFS

AGLPKTEANW VNVISDLKKI EDLIQSMHID ATLYTESDVH

PSCKVTAMKC FLLELQVISL ESGDASIHDT VENLIILANN

SLSSNGNVTE SGCKECEELE EKNIKEFLQS FVHIVQMFIN TS
```

IL-15 can induce proliferation of antigen-activated T cells and stimulate natural killer (NK) cells. The biological activity of IL-15 is mediated through a multi-subunit receptor complex (IL-15R) which shares the beta (CD122) and gamma (CD132) subunits of the IL-2 receptor complex, but has a unique alpha subunit (IL-15Rα, also known as CD215 in humans). IL-15 derived polypeptides can be used in cancer immunotherapies. The therapeutic agent can also further include an IL-15 binding fragment of the IL-15Ra receptor, e.g., the sushi domain of IL-2Ra. The IL-15 binding fragment of IL-15Ra can be covalently linked to the biologically active portion of IL-15 or can be non-covalently linked.

Advantages of using a VSA in association with IL-15 (e.g., using a VSA-IL-15 fusion protein) include, e.g., extending the PK of the IL-15. The extended PK can have advantages; for example, the IL-15 can be administered less frequently and/or at reduced concentrations and/or more consistent delivery levels of the IL-15 can be achieved.

Hepcidin.

In certain embodiments, the therapeutic agent is a hepcidin (e.g., human hepcidin), or a biologically active variant of hepcidin. Human hepcidin is an 84 amino acid protein (Uniprot Accession number P81172), including a 24 amino acid N-terminal signal peptide, a thirty amino acid propeptide, and a 25 amino acid mature peptide (amino acids 60 to 84); hepcidin can be alternately cleaved to form a 20 amino acid mature peptide (amino acids 65 to 84).

```
                                            [SEQ ID NO: 13]
    MALSSQIWAA CLLLLLLLAS LTSGSVFPQQ TGQLAELQPQ

DRAGARASWM PMFQRRRRRD THFPICIFCC GCCHRSKCGM CCKT
```

Hepcidin is known to be involved in iron homeostasis (e.g., Laftah et al., Blood, 103:3940-44 (2004); U.S. Pat. No. 7,169,758). Accordingly, hepcidin can be used an agent for regulation of iron absorption and homeostasis. It can be used to treat abnormal iron absorption, e.g., in individuals with β-thalassemia and related disorders.

The therapeutic agent can comprise a hepcidin peptide, or a variant of such peptide containing one or more amino acid variations from the mature hepcidin peptide. In a particular embodiment, two mature hepcidin peptides are fused or joined to each end of an albumin moiety, such as a VSA, such that the hepcidin molecules are able to interact with the natural binding partner for hepcidin, ferroportin. Ferroportin is known to exist in dimers, and both monomers must be capable of binding hepcidin for Jak2 to bind to ferroportin.

Advantages of using a VSA in association with a hepcidin (e.g., using a VSA-hepcidin fusion protein) include, e.g., extending the PK of the hepcidin. The extended PK can have advantages; for example, the hepcidin can be administered less frequently and/or at reduced concentrations and/or more consistent delivery levels of the hepcidin can be achieved.

Coagulation Factor VII (FVII).

In certain embodiments, the therapeutic agent is an FVII (e.g., a human FVII) or a biologically active variant or fragment thereof. Human FVII is a 466 amino acid protein, including a 20 amino acid N-terminal signal peptide and a 40 amino acid propeptide, a 152 amino acid light chain and a 254 amino acid heavy chain. Thim et al., Biochemistry, 27:7785-93 (1998); Hagen et al., PNAS USA 83:2412-16 (1986); O'Hara et al., PNAS USA 84:5158-62 (1987) and Sabater-Lleal et al., Hum Genet 118:741-51 (2006); Hagen, U.S. Pat. No. 4,784,950; Uniprot Accession No. P08709. Thus, the mature FVII is a single chain glycoprotein (mol. wt. 50,000) of 406 amino acids that is secreted into the blood where it circulates in a zymogen form. FVII comprises a 45 amino acid Gla domain (amino acids 61 through 105); a potentially calcium-binding 37 amino acid EGF-like domain (amino acids 106 through 142); a 42 amino acid EGF-like domain (amino acids 147 through 188) and a 240 amino acid serine peptidase domain (amino acids 213 through 452). In vitro, FVII can be proteolytically cleaved to form activated FVII, or FVIIa, by the action of activated coagulation factors Factor X (FXa), Factor IX (FIXa), Factor XII (FXIIa) or Factor II (FIIa). FVIIa does not promote coagulation by itself, but can complex with tissue factor (TF) exposed at the site of injury. The FVIIa/TF complex can convert FX to FXa, and FIX to FIXa, thereby inducing local hemostasis at the site of injury. Activation of FVII to FVIIa involves proteolytic cleavage at a single peptide bond between Arg-152 and Ile-153, resulting in a two-chain molecule consisting of a light chain of 152 amino acid residues and a heavy chain of 254 amino acid residues held together by a single disulfide bond. Persons with hemophilia may have normal levels of FVII. However, they suffer from a relative deficiency in FVIIa and other activated clotting factors.

It is known that basal levels of Factor VIIa in plasma are greatly reduced in subjects with hemophilia B (Factor IX deficiency) and, to a lesser extent, subjects with hemophilia A (Factor VIII deficiency). Wildgoose et al., Blood 1:25-28 (1992). In the absence of activated FVIIa, the intrinsic blood clotting pathway involving FVII and FIX, is severely limited in effective coagulation. Recently, recombinant activated Factor VII (rFVIIa, NovoSeven®, Novo, Nordisk) has been shown to have therapeutic value to bypass or correct the coagulation defects in hemophilia A and B subjects with inhibitors, especially in subjects with inhibitors who were undergoing surgical procedures. NovoSeven® is a 406 amino acid glycoprotein that is structurally similar to plasma-derived FVIIa. However, recombinant FVIIa is expensive to manufacture. Another critical problem is the short half-life (2 hours) of recombinant FVIIa. Therefore, recombinant FVIIa therapy requires an intravenous infusion of high doses of the protein every 2 hours. Accordingly, sequences useful as the therapeutic agent in the present invention include sequences encoding FVII and FVIIa.

In particular embodiments, the agent used herein can be a Factor VII or Factor VIIa peptide. In particular embodiments, the Factor VII peptide can contain one or more mutations to provide an enzymatic cleavage site, such as an enzymatic cleavage site susceptible to cleavage by SKI-1 or furin (e.g., U.S. Pat. No. 7,615,537).

Advantages of using a VSA in association with a FVII (e.g., using a VSA-FVII fusion protein) include, e.g., extending the PK of the FVII. The extended PK can have advantages; for example, the FVII can be administered less frequently and/or at reduced concentrations and/or more consistent delivery levels of the FVII can be achieved.

Coagulation Factor VIII (FVIII).

In certain embodiments, the therapeutic agent is an FVIII (e.g., human FVIII) or a biologically active variant or fragment thereof. For example, Toole, U.S. Pat. No. 4,757,006 discloses the amino acid sequence of the full-length wild-type human FVIII, and for example, Toole, U.S. Pat. No. 4,868,112 discloses the amino acid sequence of human FVIII, wherein the B-domain has been deleted. FVIII, also commonly referred to as antihemophilic factor (AHF) is a large, 2351 amino acid protein that is processed into multiple chains in a complex manner, including a 19 amino acid signal peptide (amino acids 1 to 19); a 1313 amino acid (amino acids 20 through 1332) or 740 amino acid (amino acids 20 through 759) light chain; a 573 amino acid B chain (amino acids 760 through 1332); and a 684 amino acid light chain (amino acids 1668 through 2351). Wood et al., Nature 312:330-37 (1984); Toole et al., Nature, 312:342-47 (1984); UniProt Accession No. P00451. AHF molecules have been approved as therapeutic treatments for subjects with hemophilia A (Recombinate®, Baxter Healthcare/Wyeth BioPharma; Advate®, Baxter Healthcare; Kogenate®, Bayer Healthcare; Xyntha® Wyeth Pharmaceuticals; Monoclate-P®, CSL Behring LLC). It has been found that the B-domain is not essential to activity, Pittman et al., Blood, 81:2925-35 (1993), and therefore, B-domain-deleted Factor VIII molecules have also been approved as a therapeutic treatment for hemophilia A (ReFacto®; Genetics Institute/Wyeth Pharmaceuticals). See, also, U.S. Pat. No. 7,572,619. Accordingly, sequences useful as the therapeutic agent in the present invention include sequences encoding FVIII and B-domain deleted FVIII.

FVIII and B-domain-deleted FVIII may be expressed and/or administered in conjunction with von Willebrand's Factor (VWF). VWF is a large (2,813 amino acid) protein comprising multiple repetitive domains which form multimers and acts as a chaperone protein for FVIII. Accession number P04275. VWF/FVIII complex has been approved as a therapeutic treatment for spontaneous or trauma-induced bleeding episodes in patients with moderate or severe von Willebrand Disease (Wilate®, Octapharma).

Advantages of using a VSA in association with a FVIII (e.g., using a VSA-FVIII fusion protein) include, e.g., extending the PK of the FVIII. The extended PK can have advantages; for example, the FVIII can be administered less frequently and/or at reduced concentrations and/or more consistent delivery levels of the FVIII can be achieved.

Coagulation Factor IX (FIX).

In certain embodiments, the therapeutic agent is an FIX (e.g., a human FIX) or a biologically active variant or fragment thereof. Human FIX is a 461 amino acid secreted protein, including a 28 amino acid N-terminal signal peptide and an 18 amino acid propeptide. The protein comprises a 415 amino acid chain [amino acids 47 through 461]; or can be processed by human Factor XIa to form a 145 amino acid Factor IXa light chain [amino acids 47 through 191]; a 35 amino acid propeptide/activation peptide [amino acids 192 through 226]; and a 235 amino acid Factor IXa heavy chain [amino acids 227 through 461]. Kurachi and Davie, PNAS USA 79:6461-64 (1982); Anson et al., Nucleic Acids Res. 11:2325-35 (1983); UniProt Accession No. P00740. Coagulation Factor IX therapy has been approved as therapeutic treatment for subjects suffering from hemophilia B, including BeneFIX® (Wyeth); Mononine® (Behring); and Alphanine® (Grifols Biologics). Accordingly, sequences useful as the therapeutic agent in the present invention include sequences encoding FIX (below) and FIXa.

```
                                              [SEQ ID NO: 14]
MQRVNMIMAE SPGLITICLL GYLLSAECTV FLDHENANKI

LNRPKRYNSG KLEEFVQGNL ERECMEEKCS FEEAREVFEN

TERTTEFWKQ YVDGDQCESN PCLNGGSCKD DINSYECWCP

FGFEGKNCEL DVTCNIKNGR CEQFCKNSAD NKVVCSCTEG

YRLAENQKSC EPAVPFPCGR VSVSQTSKLT RAETVFPDVD

YVNSTEAETI LDNITQSTQS FNDFTRVVGG EDAKPGQFPW

QVVLNGKVDA FCGGSIVNEK WIVTAAHCVE TGVKITVVAG

EHNIEETEHT EQKRNVIRII PHHNYNAAIN KYNHDIALLE

LDEPLVLNSY VTPICIADKE YTNIFLKFGS GYVSGWGRVF

HKGRSALVLQ YLRVPLVDRA TCLRSTKFTI YNNMFCAGFH

EGGRDSCQGD SGGPHVTEVE GTSFLTGIIS WGEECAMKGK

YGIYTKVSRY VNWIKEKTKL T
```

Advantages of using a VSA in association with a FIX (e.g., using a VSA-FIX fusion protein) include, e.g., extending the PK of the FIX. The extended PK can have advantages; for example, the FIX can be administered less frequently and/or at reduced concentrations and/or more consistent delivery levels of the FIX can be achieved.

Erythropoietin (EPO).

In one embodiment, the therapeutic agent is an EPO (e.g., a human EPO) or a biologically active variant or fragment thereof. Human EPO is a 193 amino acid protein, including a 27 amino acid N-terminal signal peptide. (Uniprot Accession Number: P01588). For example, the therapeutic agent can have the ability to increase red blood cell production. EPO is an approved therapeutic for treatment of anemia, and is marketed as Epogen® (Amgen, Thousand Oaks, Calif.); Recormon® (Roche, South San Francisco, Calif.) and under a number of other marketed names. An exemplary amino acid sequence encoding human EPO is:

```
                                              [SEQ ID NO: 15]
MGVHECPAWL WLLLSLLSLP LGLPVLGAPP RLICDSRVLE

RYLLEAKEAE NITTGCAEHC SLNENITVPD TKVNFYAWKR

MEVGQQAVEV WQGLALLSEA VLRGQALLVN SSQPWEPLQL

HVDKAVSGLR SLTTLLRALG AQKEAISPPD AASAAPLRTI

TADTFRKLFR VYSNFLRGKL KLYTGEACRT GDR
```

Advantages of using a VSA in association with an EPO (e.g., using a VSA-EPO fusion protein) include, e.g., extending the PK of the EPO. The extended PK can have advantages; for example, the EPO can be administered less frequently and/or at reduced concentrations and/or more consistent delivery levels of the EPO can be achieved.

Granulocyte Colony Stimulating Factor (G-CSF).

In one embodiment, the therapeutic agent is a G-CSF (e.g., human G-CSF) or a biologically active variant or fragment thereof. Human G-CSF is a 207 amino acid protein, including a 29 amino acid N-terminal signal peptide. (Uniprot Accession No. P09919). For example, the therapeutic agent can have the ability to increase the level of neutrophils in the blood. G-CSF is an approved therapeutic for the treatment of neutropenia, that is low neutrophil levels, and is marketed as Neupogen® (Amgen); and as Granocyte® (Chugai, Turnham Green, UK). An exemplary amino acid sequence encoding human G-CSF is:

```
                                       [SEQ ID NO: 16]
MAGPATQSPM KLMALQLLLW HSALWTVQEA TPLGPASSLP

QSFLLKCLEQ VRKIQGDGAA LQEKLVSECA TYKLCHPEEL

VLLGHSLGIP WAPLSSCPSQ ALQLAGCLSQ LHSGLFLYQG

LLQALEGISP ELGPTLDTLQ LDVADFATTI WQQMEELGMA

PALQPTQGAM PAFASAFQRR AGGVLVASHL QSFLEVSYRV

LRHLAQP
```

Advantages of using a VSA in association with an G-CSF (e.g., using a VSA-G-CSF fusion protein) include, e.g., extending the PK of the G-CSF. The extended PK can have advantages; for example, the G-CSF can be administered less frequently and/or at reduced concentrations and/or more consistent delivery levels of the G-CSF can be achieved.

Interferon.

In one embodiment, the therapeutic agent is an interferon (e.g., a human interferon) or a biologically active variant or fragment thereof. In some embodiments, the interferon is a human alpha interferon, beta interferon or gamma interferon. For example, the therapeutic can have antiviral, antibacterial or anticancer activities, and important immunoregulatory activity, such as activation of macrophages.

Alpha interferons are a family of closely related proteins. Alpha interferon-2 is a 188 amino acid protein, including a 23 amino acid N-terminal signal peptide. (Uniprot Accession No. P01563). Alpha interferon-2 is an approved therapeutic for the treatment of various cancers, and is marketed as Roferon-A® (Roche); and Intron-A® (Schering-Plough). An exemplary amino acid sequence of human alpha interferon-2 is:

```
                                       [SEQ ID NO: 17]
MALTFALLVA LLVLSCKSSC SVGCDLPQTH SLGSRRTLML

LAQMRKISLF SCLKDRHDFG FPQEEFGNQF QKAETIPVLH

EMIQQIFNLF STKDSSAAWD ETLLDKFYTE LYQQLNDLEA

CVIQGVGVTE TPLMKEDSIL AVRKYFQRIT LYLKEKKYSP

CAWEVVRAEI MRSFSLSTNL QESLRSKE
```

Beta interferon is a 187 amino acid protein, including a 21 N-terminal amino acid signal peptide. (Uniprot Accession No. P01574). Beta interferon is an approved therapeutic for the treatment of multiple sclerosis, and is marketed as Avonex® (Biogen Idec, Cambridge, Mass.); Betaseron® (Berlex) and Rebif® (Ares-Serono). See also, Houghton et al., Nucleic Acids Res., 8:2885-94 (1980). An exemplary amino acid sequence of human beta interferon is:

```
                                       [SEQ ID NO: 18]
MTNKCLLQIA LLLCFSTTAL SMSYNLLGFL QRSSNFQCQK

LLWQLNGRLE YCLKDRMNFD IPEEIKQLQQ FQKEDAALTI

YEMLQNIFAI FRQDSSSTGW NETIVENLLA NVYHQINHLK
```

```
                                       -continued
TVLEEKLEKE DFTRGKLMSS LHLKRYYGRI LHYLKAKEYS

HCAWTIVRVE ILRNFYFINR LTGYLRN
```

Gamma interferon is a 166 amino acid protein, including a 23 amino acid N-terminal signal peptide, and a 5 amino acid propeptide [residues 162-166]. (Uniprot Accession No. P01579). Gamma interferon is an approved therapeutic for the treatment of serious infections, such as those associated with chronic granulomatous disease, and is marketed as Actimmune® (Genentech). See also, Rinderknecht et al., J. Biol. Chem., 259:6790-97 (1984). An exemplary amino acid sequence of human gamma interferon is:

```
                                       [SEQ ID NO: 19]
MKYTSYILAF QLCIVLGSLG CYCQDPYVKE AENLKKYFNA

GHSDVADNGT LFLGILKNWK EESDRKIMQS QIVSFYFKLF

KNFKDDQSIQ KSVETIKEDM NVKFFNSNKK KRDDFEKLTN

YSVTDLNVQR KAIHELIQVM AELSPAAKTG KRKRSQMLFR GRRASQ
```

Advantages of using a VSA in association with an interferon (e.g., using a VSA-interferon fusion protein) include, e.g., extending the PK of the interferon. The extended PK can have advantages; for example, the interferon can be administered less frequently and/or at reduced concentrations and/or more consistent delivery levels of the interferon can be achieved.

Cytokine Antagonists.

In some embodiments, the therapeutic agent is an antagonist of cytokine signaling, e.g., an antagonist of interleukin or interferon signaling. For example, the therapeutic agent is an IL-1 receptor antagonist (IL-1ra) such as Kineret® (Amgen) or a variant thereof (see, e.g., U.S. Pat. No. 6,599,873). Human IL-1Ra is a 177 amino acid protein, including a 25 amino acid N-terminal signal peptide (Uniprot Accession No. P018510). IL1-Ra is an approved therapeutic for rheumatoid arthritis. An exemplary IL-1 receptor antagonist (IL-1ra) includes the following human amino acid sequence:

```
                                       [SEQ ID NO: 20]
MEICRGLRSH LITLLLFLFH SETICRPSGR KSSKMQAFRI

WDVNQKTFYL RNNQLVAGYL QGPNVNLEEK IDVVPIEPHA

LFLGIHGGKM CLSCVKSGDE TRLQLEAVNI TDLSENRKQD

KRFAFIRSDS GPTTSFESAA CPGWFLCTAM EADQPVSLTN

MPDEGVMVTK FYFQEDE
```

In some embodiments, the antagonist is a variant cytokine can be a cytokine with altered function, e.g., a dominant negative cytokine. Exemplary variant cytokines include IL-17 molecules described in WO2011/044563 and IL-23 molecules described in WO2011/011797.

Advantages of using a VSA in association with a cytokine antagonist (e.g., using a VSA-cytokine antagonist fusion protein) include, e.g., extending the PK of the cytokine antagonist. The extended PK can have advantages; for example, the cytokine antagonist can be administered less frequently and/or at reduced concentrations and/or more consistent delivery levels of the cytokine antagonist can be achieved.

Urate Oxidase

In one embodiment, the therapeutic agent is a urate oxidase, also known as uricase, or a biologically active variant or fragment thereof. An exemplary urate oxidase sequence is the sequence from *Aspergillus flavus*:

[SEQ ID NO: 21]
```
MSAVKAARYG KDNVRVYKVH KDEKTGVQTV YEMTVCVLLE

GEIETSYTKA DNSVIVATDS IKNTIYITAK QNPVTPPELF

GSILGTHFIE KYNHIHAAHV NIVCHRWTRM DIDGKPHPHS

FIRDSEEKRN VQVDVVEGKG IDIKSSLSGL TVLKSTNSQF

WGFLRDEYTT LKETWDRILS TDVDATWQWK NFSGLQEVRS

HVPKFDATWA TAREVTLKTF AEDNSASVQA TMYKMAEQIL

ARQQLIETVE YSLPNKHYFE IDLSWHKGLQ NTGKNAEVFA

PQSDPNGLIK CTVGRSSLKS KL
```

Both humans and certain other primates lack a naturally occurring urate oxidase protein, presumably due to an adaptive evolution. (Wu et al., PNAS USA, 86:9412-16 (1989)). However, many mammalian species of urate oxidase are known, including pig (Uniprot Accession No. P16164); cynomogus monkey (Uniprot Accession No. Q8MHW6); baboon (Uniprot Accession No. P25689); rabbit (Uniprot Accession No. P011645); rat (Uniprot Accession No. P09118); and mouse (Uniprot Accession No. P25688). Urate oxidase catalyzes the oxidation or uric acid to 5-hydroxyisourate, leading to increased solubility and renal excretion, which can prevent symptoms of gout. Urate oxidase is an approved therapeutic for the treatment of hyperuricaemia, and is marketed as Rasburicase® (recombinant uricase from *Aspergillus flavus* produced in *Saccharomyces cerevisiae*; Sanofi-Aventis) or Krystexxa® (recombinant pegylated chimeric uricase, sequence from pig/baboon, produced in *Saccharomyces cerevisiae*, Savient Pharmaceuticals, Inc.). These products have been reported to be immunogenic, which can limit the ability to treat patients repeatedly. For this reason, the approaches provided herein can have additional advantages in that the VSA can serve to prevent or impede the native immune system from readily accessing the biologically active uricase moiety, and thereby can reduce or prevent the formation of antibodies to the biologically active uricase moiety after administration.

Advantages of using a VSA in association with a urate oxidase (e.g., using a VSA-urate oxidase fusion protein) include, e.g., extending the PK of the urate oxidase. The extended PK can have advantages; for example, the urate oxidase can be administered less frequently and/or at reduced concentrations and/or more consistent delivery levels of the urate oxidase can be achieved.

C-Natriuretic Peptide (CNP).

In one embodiment, the therapeutic agent is a CNP (e.g., human CNP) or a biologically active variant or fragment thereof. Human CNP is a 126 amino acid protein, including a 23 amino acid N-terminal signal peptide; a 50 amino acid propeptide (amino acids 24-73); and a 53 amino acid CNP-53 peptide (amino acids 74-126). The 53 amino acid CNP-53 peptide may be further processed to a 29 amino acid CNP-29 peptide (amino acids 98-126) or a 22 amino acid CNP-22 peptide (amino acids 105-126) (Uniprot Accession No. P23582). An exemplary amino acid sequence encoding human CNP is:

[SEQ ID NO: 22]
```
MHLSQLLACA LLLTLLSLRP SEAKPGAPPK VPRTPPAEEL

AEPQAAGGGQ KKGDKAPGGG GANLKGDRSR LLRDLRVDTK

SRAAWARLLQ EHPNARKYKG ANKKGLSKGC FGLKLDRIGS

MSGLGC
```

CNP has been implicated in a number of physiological processes, including vasorelaxant with powerful venodilator effects, exhibiting the ability to reduce mean arterial pressure, atrial pressure and cardiac output in mammals; dose-dependent relaxant effects on bronchial smooth muscle and pulmonary arterial relaxation; and can also have involvement in neurotransmission. See, Barr et al., Peptides 17:1243-51 (1996).

Advantages of using a VSA in association with a CNP (e.g., using a VSA-CNP fusion protein) include, e.g., extending the PK of the CNP. The extended PK can have advantages; for example, the CNP can be administered less frequently and/or at reduced concentrations and/or more consistent delivery levels of the CNP can be achieved.

Production

A variety of molecular biology techniques can be used to design nucleic acid constructs encoding a protein that includes a serum albumin or a domain thereof. The nucleic acid sequences can be any sequences that code for the VSA of interest. For example, a nucleic acid sequence can be based on a known sequence that enclodes a corresponding native (e.g., wild type) serum albumin. For example, a sequence that encodes a wild type albumin can be that corresponding to UniProt DB Accession No. P02768, e.g., ENI database sequence V00494.1 (www.ebi.ac.uk/ena/data/view/V00494).

The coding sequence can include, e.g., a sequence encoding a protein described herein, a variant of such sequence, or a sequence that hybridizes to such sequences. An exemplary coding sequence for mammalian expression can further include an intron. Coding sequences can be obtained, e.g., by a variety of methods including direct cloning, PCR, and the construction of synthetic genes. Various methods are available to construct useful synthetic genes, see, e.g., the GeneArt® GeneOptimizer® from Life Technologies, Inc. (Carlsbad, Calif.), Sandhu et. al. (2008) In Silico Biology 8: 0016; Gao et al. (2004) Biotechnol Prog, 20: 443-8.; Cai et al. (2010) J Bioinformatics Sequence Analysis 2: 25-29; and Graf et al (2000), J Virol 74: 10822-10826.

The coding sequence generally employs one or more codons according to the codon tables for eukaryotic or prokaryotic expression. A coding sequence can be generated with specific codons (e.g., preferred codons) and/or one or more degenerate codons. A possible set of degenerate codons is set forth in the table below.

TABLE 1

| Amino acid | Code | Codons | Degenerate |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |

TABLE 1-continued

| Amino acid | Code | Codons | Degenerate |
|---|---|---|---|
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Stop | . | TAA TAG TGA | TRR |

The degenerate codon can be representative of all possible codons encoding each amino acid, but may not always be unambiguous. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences disclosed herein. Variant sequences can be readily tested for functionality as described herein.

In some embodiments, the coding sequence includes one or more preferred codons for the cell in which it is to be expressed. Generally preferred codons are those that are translated most efficiently and can include the codons that are most frequently used by cells of the species in question. Each species can exhibit its own codon preferences. See, e.g. Gustafsson et al. (2004) Trends in Biotechnol. 22:346-353; Grantham et al. (1980) Nuc. Acids Res. 8:1893 912; Haas et al. (1996) Curr. Biol. 6:315 24; Wain-Hobson et al. (1981) Gene 13:355 64; Grosjean and Fiers (1982) Gene 18:199 209; Holm (1986) Nuc. Acids Res. 14:3075 87; Ikemura (1982) J. Mol. Biol. 158:573 97. For example, the amino acid threonine (Thr) can be encoded by ACA, ACC, ACG, or ACT. In mammalian cells, ACC is the most commonly used Thr codon, whereas different Thr codons may be preferred in other species. Preferred codons for a particular species can be introduced into coding sequences by a variety of methods, including direct cloning, PCR mutagenesis, and the construction of synthetic genes. Introduction of preferred codon sequences into recombinant DNA can increase translational efficiency. In some embodiments, at least 10, 20, 30, 50, 60, 70, or 80% of the codons in a coding sequence are preferred codons. Sequences containing preferred codons can be constructed, and tested for expression in various species.

A protein described herein, such as a protein containing a serum albumin domain described herein, can be expressed in bacterial, yeast, plant, insect, or mammalian cells.

Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell can be a mammary epithelial cell.

Coding nucleic acid sequences can be maintained in recombinant expression vectors that include additional nucleic acid sequences, such as a sequence that regulate replications of the vector in host cells (e.g., origins of replication) and a selectable marker gene. The selectable marker gene facilitates selection of host cells into which the vector has been introduced. Exemplary selectable marker genes appropriate for mammalian cells include the dihydrofolate reductase (DHFR) gene (for use in dhfr⁻ host cells with methotrexate selection/amplification) and the neo gene (for G418 selection).

Within the recombinant expression vector, the coding nucleic acid sequences can be operatively linked to transcriptional control sequences (e.g., enhancer/promoter regulatory elements) to drive high levels of transcription of the genes. Examples of eukaryotic transcriptional control sequences include the metallothionein gene promoter, promoters and enhancers derived from eukaryotic viruses, such as SV40, CMV, adenovirus and the like. Specific examples include sequences including a CMV enhancer/AdMLP promoter regulatory element or an SV40 enhancer/AdMLP promoter regulatory element.

An exemplary recombinant expression vector also carries a DHFR gene, which allows for selection of CHO cells that have been transfected with the vector using methotrexate selection/amplification. The selected transformant host cells are cultured to allow for expression of the protein.

An adenovirus system can also be used for protein production. By culturing adenovirus-infected non-293 cells under conditions where the cells are not rapidly dividing, the cells can produce proteins for extended periods of time. For instance, BHK cells are grown to confluence in cell factories, and exposed to the adenoviral vector encoding the secreted protein of interest. The cells are then grown under serum-free conditions, which allows infected cells to survive for several weeks without significant cell division. In another method, adenovirus vector-infected 293 cells can be grown as adherent cells or in suspension culture at relatively high cell density to produce significant amounts of protein (See Garnier et al., (1994) Cytotechnol. 15:145-55, and Liu et al., (2009) J. Bioscience and Bioengineering, 107:524-529). The expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art. Recombinant baculovirus can be produced through the use of a transposon-based system described by Luckow et al. (J. Virol. 67:4566-4579, 1993). This system, which utilizes transfer vectors, is commercially available in kit form (Bac-to-Bac™ kit; Life Technologies, Rockville, Md.). An exemplary transfer vector (e.g., pFastBac1™ Life Technologies) contains a Tn7 transposon to transfer the DNA encoding the protein of interest into a baculovirus genome maintained in *E. coli* as a bacmid. See, Condreay et al., (2007) Current Drug Targets 8:1126-1131. In addition, transfer vectors can include an in-frame fusion with DNA encoding a polypeptide extension or affinity tag as disclosed above. Using techniques known in the art, a transfer vector containing nucleic acid sequence encoding a variant serum albumin fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses a protein containing a serum albumin domain is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately $2-5\times10^5$ cells to a density of $1-2\times10^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. *Agrobacterium rhizogenes* can be used as a vector for expressing genes in plant cells. See e.g., O'Neill et al. (2008) Biotechnol. Prog. 24:372-376.

Fungal cells, including yeast cells, can also be used within the present invention. Yeast species of particular interest in this regard include *Saccharomyces cerevisiae, Hansenula polymorpha, Kluyveromyces lactis, Pichia pastoris,* and *Pichia methanotica*. Transformed cells are selected by phenotype determined by the selectable marker, commonly drug resistance or the ability to grow in the absence of a particular nutrient (e.g., leucine). Production of recombinant proteins in *Pichia methanolica* is described, e.g., in U.S. Pat. Nos. 5,716,808, 5,736,383, 5,854,039, and 5,888,768.

The binding protein is recovered from the culture medium and can be purified. Various methods of protein purification can be employed and such methods are known in the art and described for example in Deutscher, *Methods in Enzymology*, 182 (1990); and Scopes, *Protein Purification: Principles and Practice*, Springer-Verlag, New York (2010) (ISBN: 1441928332). Purified variant serum albumin fusion proteins can be concentrated using standard protein concentration techniques.

Exemplary of purification procedures include: ion exchange chromatography, size exclusion chromatography, and affinity chromatography as appropriate. For example, variant serum albumin fusion proteins can be purified with a HSA affinity matrix.

To prepare the pharmaceutical composition a variant serum albumin fusion protein is typically at least 10, 20, 50, 70, 80, 90, 95, 98, 99, or 99.99% pure and typically free of other proteins including undesired human proteins and proteins of the cell from which it is produced. It can be the only protein in the composition or the only active protein in the composition or one of a selected set of purified proteins. Purified preparations of a variant serum albumin fusion protein described herein can include at least 50, 100, 200, or 500 micrograms, or at least 5, 50, 100, 200, or 500 milligrams, or at least 1, 2, or 3 grams of the binding protein. Accordingly, also featured herein are such purified and isolated forms of the binding proteins described herein. The term "isolated" refers to material that is removed from its original environment (e.g., the cells or materials from which the binding protein is produced).

Linkers

In some embodiments described herein, a VSA is associated with an agent (e.g., a diagnostic or therapeutic agent), e.g., for the purpose of improving a functional property (e.g., extending the PK) of the agent. In some embodiments, the VSA is physically attached to the agent. The VSA can be directly attached to the agent or it can be attached to the agent via a linker.

In some embodiments, a heterologous protein that comprises a VSA and an additional agent (e.g., a diagnostic or therapeutic agent) is made using recombinant DNA techniques. In some embodiments, the VSA is produced (e.g., using recombinant DNA techniques) and subsequently linked to the agent, e.g., by chemical means.

A variety of linkers can be used to join a polypeptide component of an agent to domain III or a variant serum albumin. The linker can be a molecule or group of molecules (such as a monomer or polymer) that connects two molecules and optionally to place the two molecules in a particular configuration. Exemplary linkers include polypeptide linkages between N- and C-termini of proteins or protein domains, linkage via disulfide bonds, and linkage via chemical cross-linking reagents.

In some embodiments, the linker includes one or more peptide bonds, e.g., generated by recombinant techniques or peptide synthesis. The linker can contain one or more amino acid residues that provide flexibility. In some embodiments, the linker peptide predominantly includes the following amino acid residues: Gly, Ser, Ala, and/or Thr. The linker peptide should have a length that is adequate to link two molecules in such a way that they assume the correct conformation relative to one another so that they retain the desired activity. Suitable lengths for this purpose include at least one and not more than 30 amino acid residues. For example, the linker is from about 1 to 30 amino acids in length. A linker can also be, for example, 1, 2, 3, 4, 5, 6, 7, 8, 9, 10, 11, 12, 13, 14, 15, 16, 17, 18, 19 and 20 amino acids in length.

Exemplary linkers include glycine-serine polymers (including, for example, (GS)n, (GSGGS)n, (SEQ ID NO: 23), (GGGGS)n (SEQ ID NO: 24) and (GGGS)n (SEQ ID NO: 25), where n is an integer of at least one, e.g., one, two, three, or four), glycine-alanine polymers, alanine-serine polymers, and other flexible linkers. Glycine-serine polymers can serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers can also be identified from three-dimensional structures in structure databases for natural linkers that bridge the gap between two polypeptide chains. In some embodiments, the linker is from a human protein and/or is not immunogenic in a human. Thus linkers can be chosen such that they have low immunogenicity or are thought to have low immunogenicity. For example, a linker can be chosen that exists naturally in a human. In certain embodiments the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n (SEQ ID NO: 24), through random mutagenesis. Alternatively, once a suitable polypeptide linker is defined, additional linker polypeptides can be created to select amino acids that more optimally interact with the domains being linked. Other types of linkers include artificial polypeptide linkers and inteins. In another embodiment, disulfide bonds are designed to link the two molecules. Other examples include peptide linkers described in U.S. Pat. No. 5,073,627, the disclosure of which is hereby incorporated by reference. In certain cases, the diagnostic or therapeutic protein itself can be a linker by fusing tandem copies of the peptide to a variant serum albumin polypeptide. In certain embodiments, charged residues including arginine, lysine, aspartic acid, or glutamic acid can be incorporated into the linker sequence in order to form a charged linker.

In another embodiment, linkers are formed by bonds from chemical cross-linking agents. For example, a variety of bifunctional protein coupling agents can be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Chemical linkers can enable chelation of an isotope. For example, $C^{14}$ 1-isothiocyanatobenzyl-3-methyldiethylene triaminepentaacetic acid (MX-DTPA) is an exemplary chelating agent for conjugation of radionucleotide to the antibody (see PCT WO 94/11026).

The linker can be cleavable, facilitating release of a payload, e.g., in the cell or a particular milieu. For example, an acid-labile linker, peptidase-sensitive linker, dimethyl linker or disulfide-containing linker (Chari et al., Cancer Research 52:127-131 (1992)) can be used. In some embodiments, the linker includes a non-proteinaceous polymer, e.g., polyethylene glycol (PEG), polypropylene glycol, polyoxyalkylenes, or copolymers of polyethylene glycol and polypropylene glycol.

In one embodiment, the variant serum albumin fusion of the present invention is conjugated or operably linked to another therapeutic compound, referred to herein as a conjugate. The conjugate can be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents can find use as variant serum albumin fusion conjugates. In an alternate embodiment, the variant serum albumin fusion is conjugated or operably linked to a toxin, including but not limited to small molecule toxins and enzymatically active toxins of bacterial, fungal, plant or animal origin, including fragments and/or variants thereof. Small molecule toxins include but are not limited to calicheamicin, maytansine (U.S. Pat. No. 5,208,020), trichothene, and CC1065. In one embodiment of the invention, the variant serum albumin fusion is conjugated to one or more maytansine molecules (e.g. about 1 to about 10 maytansine molecules per antibody molecule). Maytansine can, for example, be converted to May-SS-Me which can be reduced to May-SH3 and reacted with a variant serum albumin fusion (Chari et al., 1992, Cancer Research 52: 127-131) to generate a maytansinoid-antibody or maytansinoid-Fc fusion conjugate. Another conjugate of interest comprises a variant serum albumin fusion conjugated to one or more calicheamicin molecules. The calicheamicin family of antibiotics are capable of producing double-stranded DNA breaks at sub-picomolar concentrations. Structural analogues of calicheamicin that can be used include but are not limited to $\gamma_1^1$, $\alpha_2^1$, $\alpha alpha_3$, N-acetyl-$\gamma_1^1$, PSAG, and $f_1^1$, (Hinman et al., 1993, Cancer Research 53:3336-3342; Lode et al., 1998, Cancer Research 58:2925-2928) (U.S. Pat. Nos. 5,714,586; 5,712,374; 5,264,586; 5,773,001). Dolastatin 10 analogs such as auristatin E (AE) and monomethyl-auristatin E (MMAE) can find use as conjugates for the variant serum albumin fusions of the present invention (Doronina et al., 2003, Nat Biotechnol 21:778-84; Francisco et al., 2003 Blood 102:1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, PCT WO 93/21232. The present invention further contemplates a conjugate or fusion formed between a variant serum albumin fusion of the present invention and a compound with nucleolytic activity, for example a ribonuclease or DNA endonuclease such as a deoxyribonuclease (DNase).

In an alternate embodiment, a variant serum albumin fusion of the present invention can be conjugated or operably linked to a radioisotope to form a radioconjugate. A variety of radioactive isotopes are available for the production of radioconjugate variant serum albumin fusions. Examples include, but are not limited to, $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu.

Screening Methods
Assays

Binding of a serum albumin or a domain thereof to FcRn can be evaluated in vitro, e.g., by surface plasmon resonance, (see, e.g., Example 2), ELISA (see, e.g., Example 4) or other binding assay known in the art.

FcRn can be produced as a single chain molecule, e.g., in CHO cells. An exemplary method for producing single chain FcRn is described in Feng et al., Protein Expression and Purification, 79:66-71 (2011).

The half-life of a protein that includes serum albumin or a domain thereof in vivo can be evaluated in a mammal, e.g., a murine model that includes a human FcRn. See e.g., Example 3. For example, the protein that is evaluated can be a protein that includes serum albumin or a domain thereof and a therapeutic agent.

Activity Assays

To assess the activity of an agent (e.g., a therapeutic agent) that is associated with a VSA as described herein, methods known in the art for testing the activity of the agent can be used. The following description provides examples of such methods.

Assays for Testing the Activity of a FVII

Examples of assays that can be used to test the activity of a FVII entity are known in the art. The following exemplary coagulation assays are adapted from Wildgoose et al., Blood, 80:25-28 (1992). All plasma factor VIIa levels are measured in a one-stage clotting assay using an ACL300R automated coagulation instrument which can be purchased from Instrumentation Laboratories (Ascoli Piceno, Italy). Test samples are diluted fivefold in 0.1 mol/L NaCl10.05 mol/L Tris-HCl/ 0.1% BSA pH 7.4 (TBSIBSA) and mixed with an equal volume of hereditary factor VII deficient plasma to yield a total volume of 100 pL. Each aliquot is subsequently incubated for 5 minutes at 37° C. with 50 KL of bovine phospholipids (Thrombofax). Coagulation is then initiated by the addition of a 100-kL aliquot of 10 nmol/L TF1.218 diluted in 12.5 mmol/L CaC12/0.1 mol/L NaCl/0.05 mol/L Tris/1% BSA pH 7.4. Coagulation times are subsequently converted to factor VIIa concentration (nanograms per milliliter) by comparison to a standard curve constructed with varying concentrations (0.05 to 50 ng/mL) of purified recombinant factor VIIa diluted in TBS/BSA.

Venipunctures are performed atraumatically and blood samples drawn into citrated vacutainers. The citrated samples are centrifuged for 15 minutes at 1,200×g after which time the plasma is removed with a plastic pipette and stored at −80° C. Normal plasma samples are collected from 10 fasting and 10 nonfasting individuals who have a negative history for bleeding as well as thrombosis and are not taking any medications at the time of sample collection. Samples are obtained from 13 severe hemophilia A and seven hemophilia B subjects (<1% FVIII:C and <1% FIXC). Subjects are excluded from the study if they have received factor concentrates, cryoprecipitate, and/or antifibrinolytics within the previous 48 hours.

The following assay is adapted from Silveira et al., Arteriosclerosis and Thrombosis, 14:60-69 (1994). Coagulation factor VII is assessed in plasma samples drawn before ingestion of the test meal and 3, 6, and 12 hours thereafter. Factor VIIc is determined as described in van Deijk et al., Haemostasis, 13:192-97 (1983) in an LODE coagulometer (Groningen, the Netherlands). Briefly, 100/iL of diluted plasma sample, 100/xh of factor Vll-deficient plasma (Helena Laboratories, Beaumont, Tex.), and 100 pL of human brain thromboplastin (prepared according to Owren and Aas, Scand J. Clin Lab Invest 3:201-18 (1951) are incubated together at 37° C. for 30 seconds. Calcium, 100 $\square$L of a 33 mmol/L solution, is added and the clotting time recorded. Factor VIIa is determined with either Thrombotest (a bovine brain thromboplastin preparation that also contains adsorbed bovine plasma; Nyegaard & Co, Oslo, Norway) (VIIa:A) or bovine brain thromboplastin (Diagnostic Reagents Ltd, Thames, Oxon, UK) (VIIa:B) in clotting assays that are otherwise essentially as described above. Factor VII amidolytic activity (VIIam) is determined with a commercially available kit (Coa-Set FVII; Chromogenix, M6lndal, Sweden). Factor VII antigen (VII:Ag) concentration is determined with an enzyme immunoassay kit (Novoclone Factor VII EIA kit, Novo Nordic A/S, Bagsvaerd, Denmark). Results are expressed in units per milliliter, one unit being the amount or activity of factor VII present in 1 mL of a standard pooled plasma. Ratios of VIIa:B to VIIc and of VIIa:B to VII:Ag are also calculated for evaluation of the activity state of factor VII in plasma. Control experiments are performed to rule out the possibility of a direct effect of high plasma concentrations of TG-rich lipoproteins on the factor VII levels obtained in the different assays. An Sf 20 to 400 lipoprotein fraction is isolated from blood that had been drawn from a healthy control subject 3 hours after intake of a fat load. Addition of this lipoprotein fraction to control plasma to a final plasma level 500% of normal does not influence factor VII measurements.

Additional examples of clotting assays that can be adapted for use to assess the activity of a FVII in association with a VSA are described in the following publications: Broze and Majerus, J. Biol. Chem. 255:1242-47 (1980); Morrissey et al., Blood, 81:734-44 (1993); Herzog et al., Nature Medicine, 5:56-63 (1999); and Sorensen and Ingerslav, J. Thrombosis and Haemostasis, 2:102-110 (2004).

Assays for Assessing the Activity of a Hepcidin

Several significant factors can be assayed to evaluate a subject for iron overload and/or risk of iron overload. First, serum iron levels can be used as an indicator of iron overload. Tests include the serum ferritin test. A subject can be considered to be suffering from iron overload if their serum iron levels are in excess of about 350 $\square$g/dL (mild iron toxicity); generally in excess of about 500 $\square$g/dL (serious iron toxicity). A subject is considered to be at risk of iron overload if their serum iron levels are high normal or above normal ranges. Normal iron range is considered to be from about 40 to about 220 $\square$g/dL; for example, from about 50 to about 160 $\square$g/dL for adult males. Normal iron ranges for adult females are approximately 5 to 10 percent lower than that for adult males. 'High normal' iron concentration is considered to be in the upper quarter (25%) of the normal range; generally in the upper tenth (10%) of the normal range. See, Jacobs & DeMott, *Laboratory Test Handbook*, $5^{th}$ ed., (LexiComp Inc, Hudson, Ohio) (2001) at p. 203-205). As is known to those skilled in the art, 'normal ranges' of iron and iron binding capacity can vary depending upon the specific laboratory and test. Other parameters that can be used to evaluate a patient for iron overload and/or risk of overload include: measurement of hepcidin levels (see U.S. Pat. No. 7,998,691); genetic testing for the presence of mutations in one or more genes related to hemochromatosis, such as juvenile hemochromatosis (HFE2A and HFE2B genes) (see U.S. Pat. No. 8,080,651)

Assays for Assessing the Activity of a GLP-1

Culture of BRIN-BD11 Cells.

BRIN-BD11 cells are cultured in RPMI-1640 tissue culture medium containing 10% (v/v) foetal calf serum, 1% (v/v) antibiotics (100 U/ml penicillin, 0.1 mg/ml streptomycin), and 11.1 mM glucose. BRIN-BD11 cells are produced by electrofusion of a New England Deaconess Hospital (NEDH) rat pancreatic β-cell with RINm5F cell to produce and immortal, glucose sensitive cell line which is described in detail elsewhere. McClenaghan et al., Diabetes (1996) 45:1132-40. All cells are maintained in sterile tissue culture flasks (Corning Glass Works, Sunderland, UK) at 37° C. in an atmosphere of 5% $CO_2$ and 95% air using a LEEC incubator (Laboratory Technical Engineering, Nottingham, UK). [Green et al., Id.]

Stimulation of Adenylate Cyclase.

BRIN-BD11 cells are seeded into 24-well plates ($3 \times 10^5$/well) and cultured for 48 h before being pre-incubated in media supplemented with tritiated adenine (2 $mC_j$) for 16 h. The cells are washed twice with cold Hanks' buffered saline (HBS) and test solution (400 μl; 37° C.) is added. The cells are then exposed to varying concentrations ($10^{-10}$-$10^{-5}$ M) of GLP-1 glycopeptides in HBS buffer, in the presence of 1 mM IBMX and 5.6 mM glucose (20 min; 37° C.). Following incubation, test solutions are removed and 300 μl of lysis solution (5% TFA, 3% SDS, 5 mM of unlabelled ATP, and 300 μM of unlabelled cAMP) is added. Dowex and alumina exchange resins are used to separate tritiated cAMP from tritiated adenine and ATP in the cell lysate, as described previously. [Miguel et al., Biochem Pharm. (2003) 65:283-92]. The highest concentration of GLP-1 ($10^{-5}$M) is used as a maximum. Each peptide is tested by single experiment (n=3) which incorporated an internal control incubation of GLP-1 (60 nM) to ensure consistency and accuracy. [Green et al., Id.]

Insulin Secretory Responses in the Pancreatic β-Cell.

BRIN-BD11 cells are seeded into 24-multiwell plates at a density of $1 \times 10^5$/well, and allowed to attach during overnight culture. Acute studies of insulin release are preceded by a 40 minute pre-incubation at 37° C. in 1.0 ml Krebs-Ringer bicarbonate buffer (115 mM NaCl, 4.7 mM KCl, 1.28 mM $CaCl_2.2H_2O$, 1.2 mM $KH_2PO_4$, 1.2 mM $MgSO_4.7H_2O$, 10 mM $NaHCO_3$, and 5 g/L bovine serum albumin, pH 7.4) supplemented with 1.1 mM glucose. Test incubations are performed at 37° C. in the presence of 5.6 mM glucose with a range of concentrations of GLP-1 glycopeptides ($10^{-12}$-$10^{-6}$M). After a 20 minute incubation, the buffer is removed from each well and aliquots are stored at −20° C. for measurement of insulin. [Green et al., Id.]

Glucose-Lowering and Insulin Secretory Activity in Obese Diabetic (Ob/Ob) Mice.

The in vivo biological activity of variant serum albumin/GLP-1 fusion proteins can be assessed in 12-16 week old obese diabetic (ob/ob) mice. The animals are housed individually in an air-conditioned room at 22±2° C. with a 12 hour light:12 hour dark cycle. Animals are allowed drinking water ad libitum and continuous access to standard rodent maintenance diet (Trouw Nutrition, Cheshire, UK). Mice are fasted for 18 hours and intraperitoneally administered 8 ml/kg body weight with saline (9 g/L NaCl), glucose alone (18 mM/kg body weight), or in combination with GLP-1 or a variant serum albumin/GLP-1 fusion protein (25 nM/kg body weight). Blood samples are collected into chilled fluoride/heparin microcentrifuge tubes (Sarstedt, Numbrecht, Germany) immediately prior to injection and at 15, 30, and 60 minutes post injection, and the plasma obtained is stored at −20° C. All animal studies are carried out in accord with the UK Animals (Scientific Procedures) Act 1986 [Green et al., Id.] or other applicable laws.

Analyses and Statistics.

Plasma glucose levels are determined using an Analox glucose analyser (Hammersmith, London, UK), which employs the glucose oxidase method. Insulin levels are assayed by dextran-coated charcoal radioimmunoassay. Incremental areas under plasma glucose and insulin curves (AUC) are calculated using GraphPad PRISM version 3.0 (Graphpad Software, San Diego, Calif., USA), which employs the trapezoidal rule. Results are expressed as means±SEM and data are compared as appropriate using Student's t test, repeated measures ANOVA or one-way ANOVA, followed by the Student-Newman-Keuls post hoc test. Groups of data are considered significantly different if $P<0.05$.

Measurement of Binding Affinity and cAMP Production.

Binding affinity is assessed by measuring the inhibition of radiolabeled GLP-1 binding to human GLP-1 receptor-expressing chinese hamster ovary (CHO) cell membrane. Cell membrane fractions (5 μg) are incubated with 62 pM [125I]GLP-1 and variant serum albumin/GLP-1 fusion protein (final conc. 10-11 to 10-6 M) in 25 mM HEPES (pH 7.4) containing 5 mM $MgCl$, 1 mM $CaCl2$, 0.25 mg/mL bacitracin, and 0.1% bovine serum albumin (BSA) at room temperature for 2 hours (100 μL). Membranes are filtered onto a 96-well GF/C plate (PerkinElmer, Inc.) that had been presoaked in 1% polyethylenimine containing 0.5% BSA, and then washed with 25 mM HEPES buffer containing 0.5% BSA (pH 7.4). Radioactivity associated with the lysates is determined using a gamma counter. Nonspecific binding is determined by the amount of binding in the presence of 1 μM unlabeled GLP-1. Dose-response curves are plotted for the individual compounds. IC50 values are calculated using XLfit software (IDBS Inc.). For measurement of cAMP production, human GLP-1 receptor expressing CHO cells are passaged into multiwell plates (4000 cells/well) and cultured for an additional 48 h. The cells are washed with assay buffer (Hanks balanced salt solution containing 20 mM HEPES, 0.1% BSA, pH 7.4) and then exposed to variant serum albumin/GLP-1 fusion proteins (final conc. 10-12 to 10-6 M) in assay buffer containing 0.33 mM isobutylmethylxanthine and 0.67 mM RO20-1724 at room temperature for 1 h. The cells are lysed with 1% Triton X-100, and the cAMP formed is measured using a cAMP femtomolar kit (Cis Bio international). Dose-response curves are plotted for the individual compounds. EC50 values are calculated using XLfit software. [Ueda et al., J. ACS, 2009 131:6237-45]

Characterization of Stability Against Recombinant HUMAN DPP-IV.

GLP-1 or variant serum albumin/GLP-1 fusion protein (20-500 μM) is incubated at 37° C. in 100 mM HEPES buffer containing 0.05% Tween80 and 1 mM EDTA-2Na (pH 7.5) with 0.33 μg/mL, 0.66 μg/mL (19), or 1.32 μg/mL recombinant human DPP-IV (60 μL). At 5 or 10 min intervals, 7 μL is removed from the reaction mixture, and the reaction is terminated by the addition of 28 μL of 8 M GuHCl solution. The reaction products are subjected to RP-HPLC on a Develosil RPAQUEOUS-AR-3 2.0°—100 mm at 30° C., and the C-terminal degradation product is quantified by using UV absorption at 210 nm. The initial rate of the degradation reaction is determined from the slope of the linear part obtained by plotting product concentration versus time. The resulting initial rates are plotted versus peptide concentration, and kinetic parameters (KM and KM/kcat) are determined using XLfit software based on the Michaelis-Menten kinetic equation. [Ueda et al., Id.]

Characterization of Stability Against Recombinant Human NEP 24.11.

The 125 μM GLP-1 or variant serum albumin/GLP-1 fusion protein is incubated at 37° C. in 50 mM HEPES buffer containing 50 mM NaCl, and 0.05% Tween 80 with 4 μg/mL recombinant human NEP 24.11 (pH 7.4, 84 μL). After 0.5, 1, 2, 3.5, and 5 h, 8 μL is removed from the reaction mixture, and the reaction is terminated by addition of 32/Th of 8 M GuHCl solution. The reaction products are subjected to RP-HPLC on a Develosil ODSHG-54.6°—150 mm at 30° C., and the area of intact variant serum albumin/GLP-1 fusion protein is measured using UV absorption at 210 nm. [Ueda et al., Id.]

Blood Glucose-Lowering Activity in Obese Diabetic db/db Mice.

Male BKS.Cg-+Leprdb/+Leprdb mice (13-15 weeks of age) are allowed ad libitum access to food and water until the start of the experiment. At t)-2 h, access to food is restricted, and the tip of the tail is cut. At t) 0 min, a 1 μL blood sample is collected. Immediately thereafter, each mouse is injected subcutaneously with test sample (100 nmol/kg) or vehicle, and additional blood samples are collected. The vehicle is saline containing 1% BSA. Blood glucose levels are measured with a glucose oxidase biosensor (DIAMETERR; Arkray, Inc.). The effects of the test samples on blood glucose are expressed as % change relative to the respective pretreatment (t) 0 min) level. The number of mice tested is 6-7 for each group. Data are presented as means (SEM. Statistical differences are analyzed using the Dunnett's multiple comparison test, and P values less than 0.05 are regarded as significant. [Ueda et al., Id.]

Assays for Assessing Uric Acid/Gout

Methods for assessing uric acid levels and/or function as well as gout are known in the art. Methods for measurements of uric acid, e.g., in urine can be employed, as disclosed, e.g., in Ballesta-Claver et al., Analytica Chimica Acta, 702:254-61 (2011) and WO 2000/08207.

Therapeutic Administration of a VSA Composition

In certain embodiments, a VSA composition (a composition comprising a VSA or a VSA associated therapeutic agent) is administered in a therapeutically effective amount to a subject to treat a disease or condition, or ameliorate one or more symptoms of a disease or condition. Methods for delivering a therapeutic composition are known in the art and can be used to administer a VSA composition e.g., encapsulation in liposomes, microparticles, microcapsules, recombinant cells that can expressing the VSA compound, receptor-mediated endocytosis (e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, topical, intramuscular, subcutaneous, intravenous, intravascular, and intrapericardial administration and oral routes. A VSA composition can also be administered, for example, by infusion or bolus injection, by absorption through epithelial or mucosa (e.g., oral mucosa, rectal, or intestinal mucosa) and can be administered together with other biologically active agents. Administration can be systemic or local. Pulmonary administration can also be employed, e.g., by use of an inhaler or nebulizer, and formulation with an aerosolizing agent. In certain aspects, the disclosure provides a composition comprising the HSA variant or the chimeric polypeptide of the disclosure, and a pharmaceutically acceptable carrier. In certain embodiments, VSA composition is delivered locally to an area in need of treatment (e.g., muscle); this may be achieved, for example, by local infusion, topical application, by injection, by catheter, or by implant (e.g., an implant of a porous, non-porous, or gelatinous material, including membranes, such as sialastic membranes, fibers, or commercial skin substitutes). In some embodiments, a VSA composition is delivered in a vesicle such as a liposome (see Langer, 1990, Science 249: 1527-1533), a controlled release system, or with a pump (see Langer, 1990, supra), or using polymeric materials can be used (see Howard et al, 1989, J. Neurosurg. 71: 105).

Further illustration of the invention is provided by the following non-limiting examples.

EXAMPLES

Example 1 cDNA encoding mature human serum albumin was cloned into a modified version of the pYC2/CT yeast expression vector (Invitrogen) containing a Trp marker, app8 leader peptide (see Rakestraw et al., Biotechnology and Bioengineering, 103:1192-1201 (2009) for leader sequence), and N-terminal His$_6$ tag (SEQ ID NO: 26) and Factor Xa cleavage site. Point mutations, either alone or in combination, were introduced by Quikchange® mutagenesis (Agilent). The vector was transformed into BJ5α S. cerevisiae cells using the EZ-yeast kit (Zymo Research) and transformants selected on SDCAA+ura plates (2% glucose, 0.67% yeast nitrogen base, 0.5% casamino acids, 0.54% Na$_2$PO$_4$, 0.86% NaH$_2$PO$_4$.H$_2$0, 18.2% sorbitol, 1.5% agar, and 40 mg/L uracil). Selected colonies were grown in 5 mL liquid SDCAA+ura overnight at 30° C. with shaking at 250 RPM. The 5 mL overnight culture was diluted into 50 mL SDCAA+ura in a 250 mL baffled flask and grown at 30° C./250 RPM to an OD600~5. Cells were then pelleted at 3000 RPM and resuspended in 50 mL YPG media (2% galactose, 2% peptone, 1% yeast extract, 0.54% Na$_2$PO$_4$, 0.86% NaH$_2$PO$_4$.H$_2$0) to induce albumin expression. After 48 hours in YPG at 20° C./250 RPM, the cells were pelleted at 3000 RPM and the cleared supernatant filter sterilized. The secreted human serum albumin was purified by affinity chromatography using either Ni-NTA resin (Invitrogen), CaptureSelect HSA affinity resin (BAC), or Vivapure anti-HSA kit (Sartorius-Stedin). Eluted protein was buffer exchanged into PBS by several rounds of concentration and dilution using Amicon Ultra-15 spin concentrators with a 10 kDa cutoff (Millipore). Protein purity was assessed by SDS-PAGE and concentration determined by absorbance at 280.

For single-chain FcRn production, DNA encoding human beta-2 microglobulin fused to the extracellular domain of human FcRn heavy chain through a (G45)$_3$ linker (SEQ ID NO: 27) was synthesized by DNA2.0. The scFcRn DNA was cloned into a modified version of the pcDNA3.1(+) vector (Invitrogen) containing an IL-2 leader sequence and C-terminal FLAG tag by standard digestion and ligation. 80 mL of Freestyle-CHO-S cells (Invitrogen) at 1×10$^6$ cells/mL were transiently transfected with scFcRn-FLAG using the Freestyle®-MAX reagent (Invitrogen) according to manufacturer's instructions. Transfected cells were incubated at 37° C., 8% CO$_2$, with shaking at 130 rpm for 6 days. The supernatant was clarified by centrifugation and the scFcRn-FLAG protein purified on a 0.5 mL M2 anti-FLAG agarose gravity-flow column (Sigma). Bound protein was eluted with 100 mM glycine-HCl, pH 3.5 and exchanged into PBS, pH 7.4 by several rounds of concentration and dilution using Amicon Ultra-15 spin concentrators with a 10 kDa cutoff (Millipore). Protein purity was assessed by SDS-PAGE and concentration determined by absorbance at 280.

Example 1A: Methods of Identifying Mutations Modulating FcRn Binding to an Albumin Moiety A library of albumin variants with random mutations in domain III was generated and displayed on the surface of yeast. FACS selections were performed to enrich for variants with improved binding to soluble FcRn at pH 5.6. After three to four rounds of selection, a population was identified with significantly increased binding compared to a wild type human serum albumin (HSA). Twelve clones from the population after sort three and eight clones from the population after sort four were cloned and sequenced. The sequence alignments revealed mutations appearing in multiple clones after sort four: K402E (2/8), V424I (2/8), P447L/S (3/8), E492G (3/8), E505G (5/8) and V547 (6/8).

Populations after sorts three, four, five and six were also sequenced to identify other enriched mutations and the following mutations were identified: V418M, T420A, V424I, N429D, M446V, A449V, T467M, E505G/K/R, A552T, V547A.

After round seven, the library had enriched to a single clone with the following mutations: V418M, T420A, E505R, V424I, and N429D.

These data demonstrate a method for identifying mutations that can be useful for modulating FcRn binding. Further selection can be carried out by identifying mutations located near residues involved in FcRn binding, e.g., near His residues, for example H510 and H535. These data also demonstrate specific sites in an HSA useful for modulating the PK of an albumin molecule.

Example 2: Characterization of Albumin Variants

Figure 1A:
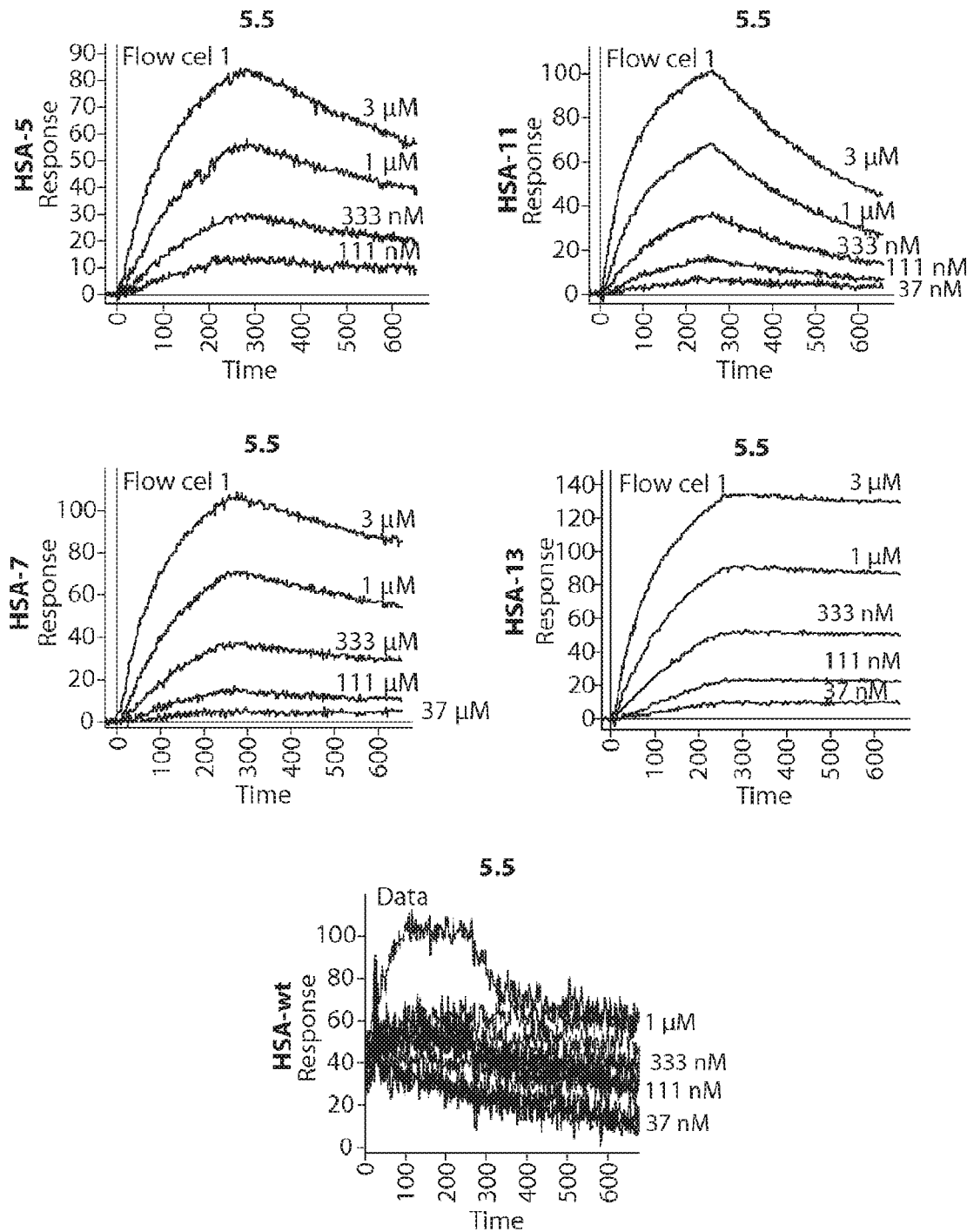
Figure 1B:
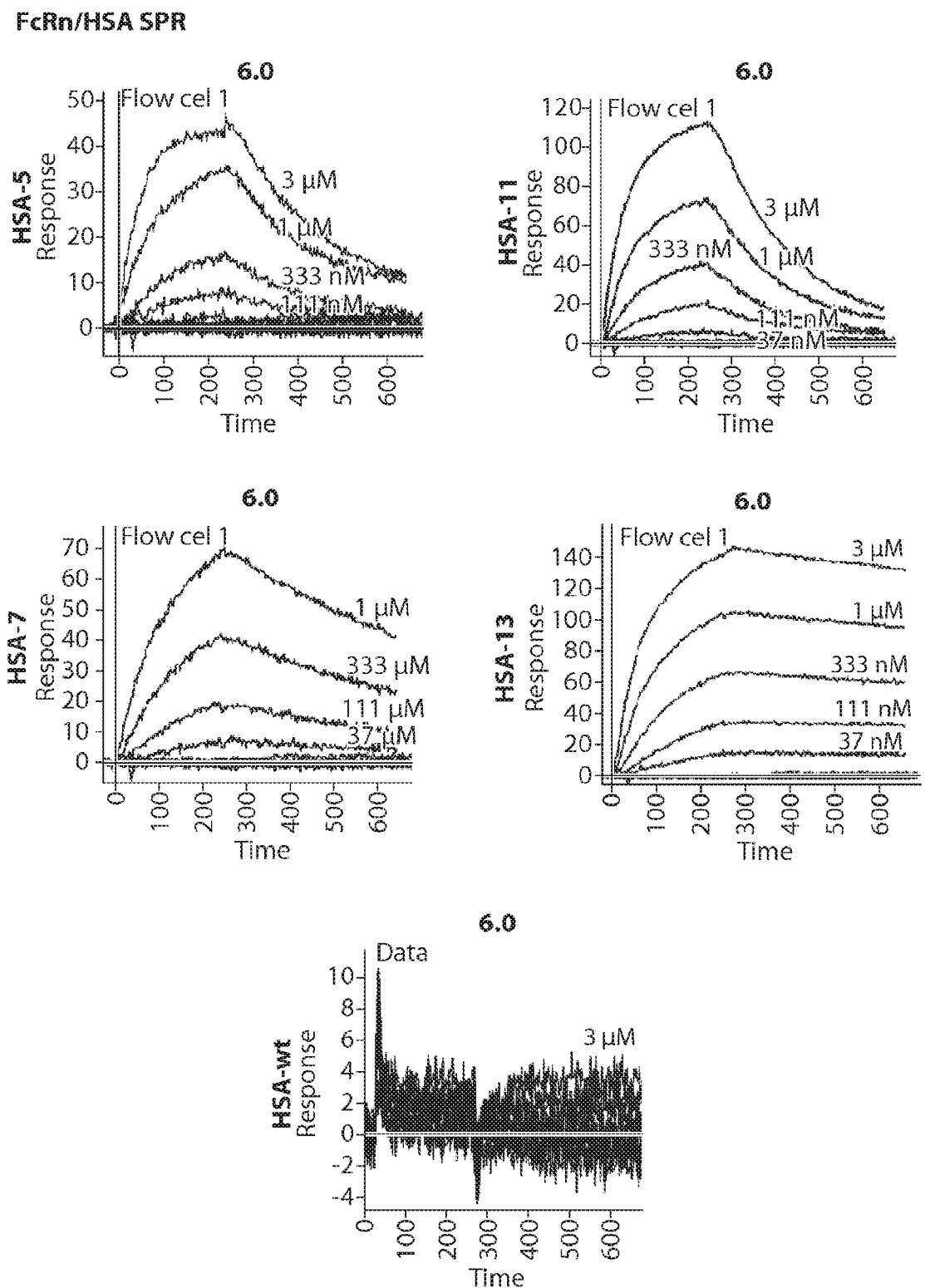
Figure 1C:
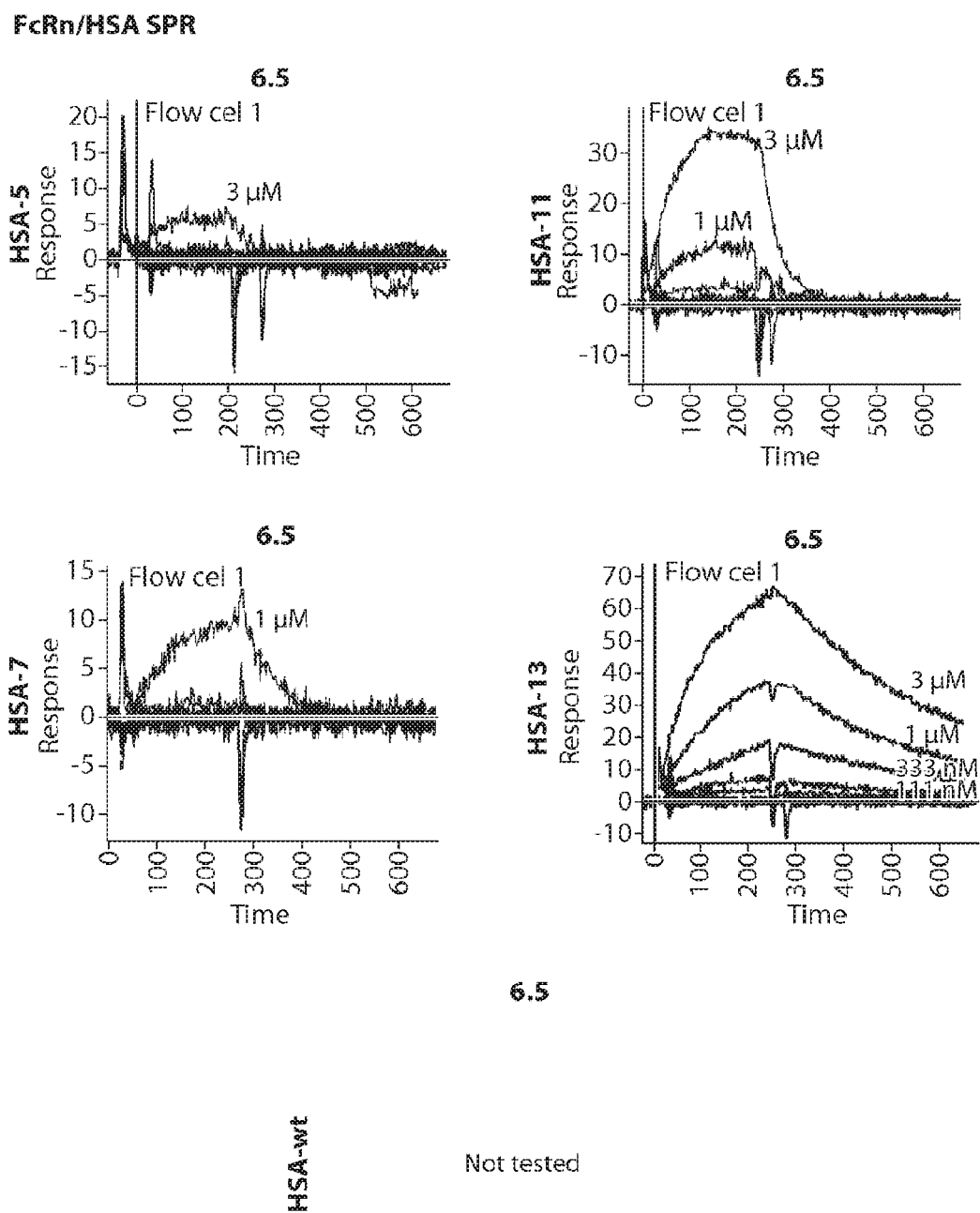

SPR was used to characterize binding of the selected variants to human FcRn at pH values from 5.5 to 7.5. An exemplary apparatus that can be used is a Reichert SR7000C® machine. FLAG-tagged, single-chain human FcRn was immobilized on a 500,000 Da carboxymethyl dextran chip by NHS/EDC chemistry. Unconjugated sites were blocked with 1 M ethanolamine. A reference channel was generated in parallel with no FcRn. HSA variants at concentrations of 1 nM-100 μM were injected at a flow rate of 50 μL/min and the difference in signal between the FcRn channel and reference channel was recorded over time to assess association. Wash buffer (PBS+0.01% Tween-20) was flowed through the channels to assess dissociation. Experiments were repeated at pH 5.5, 6.0, 6.5, and 7.4 to assess the pH dependency of binding. The results are shown in FIG. 1. The VSAs that were used are described in Example 5. These results demonstrate that affinity of certain VSAs to FcRn at pH 5.5 had increased, as did the affinity of some of these to FcRn at pH 7.4. In particular, HSA-5 and HSA-7 bound FcRn at pH 5.5 (a typical endosomal pH), but not at pH 7.4 (a typical pH of blood). In each case, the pH dependence of FcRn binding as known for native albumin was preserved.

These data demonstrate that VSAs can be generated that have increased affinity for FcRn at endosomal pH without significantly altering the affinity for FcRn at a neutral pH (e.g., a pH associated with blood).

Example 3

PK studies were performed for selected variants in human FcRn mice to determine the effect of FcRn affinity on plasma clearance. The mouse strains 4919 and 14565 from Jackson Laboratories are homozygous for mouse FcRn knockout and either hemi- or homozygous for human FcRn knock-in. Selected HSA variants were injected intravenously into such mice and bleeds were collected at various time intervals. The plasma concentration of the HSA at each time point was assessed using a non-mouse cross-reactive HSA ELISA and plotted to calculate clearance rates and plasma AUC.

Example 4

ELISA studies were performed to characterize the binding of selected HSA variants to human FcRn at pH values of 5.5-7.4. Purified HSA variants at 1 μg/mL in PBS were immobilized in a 96 well flat bottom EIA plate (Costar 9018) at 4° C. overnight. Coated wells were then blocked with 200 μL PBS+2% fish gelatin, pH 7.4 for 2 hours at room temperature. After blocking, wells were washed 3× with 200 μL PBS+0.1% Tween-20 at the appropriate pH (5.5-7.4). 100 μL of FLAG-tagged single-chain FcRn diluted to concentrations of 50 pM-200 nM in PBS+0.1% fish gelatin at pH 5.5-7.4 was added to each well and incubated for 2 hours at room temperature. Wells were then washed 3× with 200 μL PBS+0.1% Tween-20 at the appropriate pH. 100 μL of anti-FLAG-HRP (Sigma) diluted 1:1000 in PBS+0.1% fish gelatin at pH 5.5-7.4 was added to each well and incubated for 60 minutes at room temperature. Wells were washed as above and 100 μL TMB substrate (Pierce) added to each well. Color development was stopped after two minutes with well. Color development was stopped after two minutes with 2 M sulfuric acid and the signal read at absorbance 450-550 on a Spectramax M5 plate reader.

Example 4A: pH Dependent Binding Using Enzyme Linked Immunosorbent Assay (ELISA)

Figure 3:
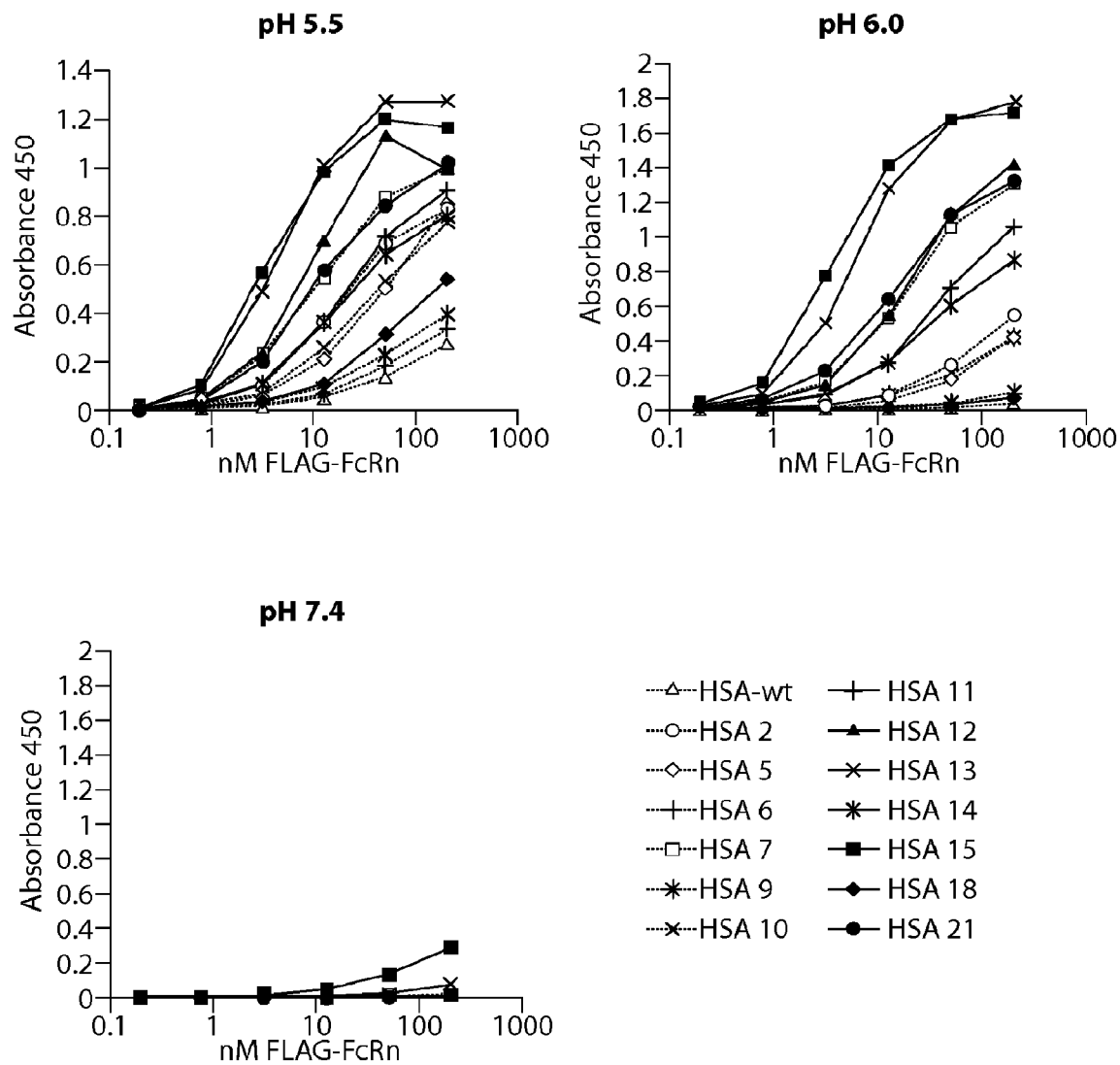
FIG. 3 is a set of graphs depicting the results of ELISA that determining the binding of VSAs and wild type HSA to human FcRn at pH 5.5, 6.0, and 7.4.

Experiments were carried out in which the binding of various VSAs and HSA to FLAG-tagged FcRn was assessed at different pHs. Results demonstrated a range of affinities for the VSAs, which were tested at pH 5.5, pH 6.0, and pH 7.4 for binding to 0.2 nM to 200 nM FcRn-FLAG. A table summarizing the results of such an experiment is shown in FIG. 2. The VSAs had $K_D$s from 3 nM to >100 nM at pH 5.5. Wild type HSA is known to have a $K_D$ of about 1-2 μM at pH 5.5. Many of the VSAs, including HSA-15, HSA-13, HSA-12, HSA-7, HSA-21, HSA-11, HSA-2, HSA-14, HSA-5, HSA-10, HSA-6, HSA-9, and HSA-18 had improved affinity for FcRn compared with wild type HSA. Additional related information, including the mutations present in the VSAs, is provided in Example 5, infra. The data of FIG. 3 demonstrate that the binding of these VSAs to FcRn, as assessed by ELISA, preserved the pH dependence of native albumin (greater binding at pH 5.5 than at pH 7.4).

These data demonstrate that VSAs with modified affinity compared to wild type HSA can be generated and provide guidance for generation of additional VSAs with increased affinity of FcRn at selected pHs.

Example 5

The amino acid sequence of Domain 3 of human serum albumin has the following sequence:

```
[SEQ ID NO: 28]
LVEEPQNLIKQNCELFEQLGEYKFQNALLVRYTKKVPQVSTPTLVEVSR

NLGKVGSKCCKHPEAKRMPCAEDYLSVVLNQLCVLHEKTPVSDRVTKC

CTESLVNRRPCFSALEVDETYVPKEFNAETFTFHADICTLSEKERQIKK

QTALVELVKHKPKATKEQLKAVMDDFAAFVEKCCKADDKETCFAEEGK

KLVAASQAALGL
```

Exemplary human serum albumin variants that were prepared include the sequences in the following table:

TABLE 2

Human Serum Albumin Variants and FcRn Binding

| VARIANT NUMBER | AMINO ACID VARIATIONS FROM DOMAIN 3 OF WILD-TYPE HUMAN SERUM ALBUMIN | FcRn BINDING [Kd@pH 5.5] Compared to WT-HSA |
|---|---|---|
| hsa-1 | WT - Full Length HSA | ± |
| hsa-2 | K573Y | +++ |
| hsa-3 | WT - Domain 3 of HSA | ± |
| hsa-4 | E492G | ± |
| hsa-5 | V547A | ++ |
| hsa-6 | E505G | + |
| hsa-7 | E505G; V547A | ++++ |
| hsa-8 | V418M | ± |
| hsa-9 | T420A | + |

TABLE 2-continued

Human Serum Albumin Variants and FcRn Binding

| VARIANT NUMBER | AMINO ACID VARIATIONS FROM DOMAIN 3 OF WILD-TYPE HUMAN SERUM ALBUMIN | FcRn BINDING [Kd@pH 5.5] Compared to WT-HSA |
|---|---|---|
| hsa-10 | V418M; T420A | ++ |
| hsa-11 | V418M; T420A; E505G | +++ |
| hsa-12 | V418M; T420A; V547A | ++++ |
| hsa-13 | V418M; T420A; E505G; V547A | +++++ |
| hsa-14 | V418M; T420A; E505G; M446V; A449V; T467M; A552T | +++ |
| hsa-15 | V418M; T420A; V424I; N429D E505R | +++++ |
| hsa-16 | E505R | ± |
| hsa-17 | E505K | ± |
| hsa-18 | V241I | + |
| hsa-19 | N429D | ± |
| hsa-20 | M446V; A449V | ± |
| hsa-21 | V418M; T420A; E505R | ++++ |
| hsa-22 | A552T | ± |
| hsa-23 | PBS [Negative Control] | ± |

All of the variants described in Table 2, with the exception of HSA-3, are full length HSA (sequence corresponding to SEQ ID NO:2) with the indicated mutations (numbering of the mutations is based on SEQ ID NO:2). As indicated in Table 2, HSA-3 is Domain 3 only of HSA with the sequence corresponding to SEQ ID NO:22. In subsequent experiments, domain 3 only versions of HSA-5 and HSA-13 were also made; these versions also demonstrated improved affinity.

Example 5A

The experiments described in this example illustrate experimental difficulties that were involved in accurately identifying serum albumin mutants that exhibit improved pharmacokinetics (e.g., increased half-life and reduced clearance) and show how these difficulties were effectively overcome.

The anti-HSA sandwich ELISA utilized in the mouse PK studies is unable to detect HSA spiked into cynomolgus monkey plasma due to the high homology of human and monkey albumin. Therefore, we developed a novel assay utilizing an epitope tag genetically fused to albumin and an anti-tag capture antibody. HSA variants with a FLAG tag, His tag, HA tag, or c-myc tag were expressed in yeast, purified, and titrated in their respective anti-tag ELISA assays in 10% monkey plasma. Both the FLAG tag and HA tag were detected in their respective assays with high sensitivity (EC50=10 ng/mL for HA, 50 ng/mL for FLAG).

In a first cynomolgus monkey PK study, FLAG-tagged HSA-wt, HSA-5, HSA-7, HSA-11, and HSA-13 were administered into two monkeys each as a 5 mg/kg iv bolus dose. To control for monkey to monkey variability and directly test for tag-specific effects on PK, a 1 mg/kg dose of HA-tagged HSA-wt was co-dosed into each animal. Bleeds were drawn at 15 minutes, 2 hours, 6 hours, 1 day, 2 days, 5 days, 9 days, 12 days, 16 days, and 21 days, and HSA concentrations were measured by both anti-FLAG and anti-HA ELISAs. A comparison of the PK traces for the FLAG-tagged HSA's (both wild-type and mutant) with the HA-tagged HSA-wt internal control indicated that the FLAG-tagged proteins were cleared at a significantly faster rate, particularly in the alpha phase. To confirm the more rapid clearance of the FLAG-tagged protein, a study was performed in which HA- and FLAG-tagged HSA-wt and HSA-7 were injected into mice. Bleeds were drawn as before and at each time point, the concentration of tagged HSA was measured with both an anti-HSA ELISA and anti-tag ELISA. For HA-HSA-wt and HA-HSA-7, the anti-HSA and anti-HA ELISA's measured HSA concentrations consistent with each other and with previous measurement of untagged HSA in mice suggesting that the HA tag accurately reflected the concentration of plasma HSA. In contrast, the anti-FLAG ELISA measured a significantly lower concentration of FLAG-HSA compared to the anti-HSA ELISA confirming that the tag was cleaved or obscured in a way that distorted the HSA measurement.

Example 6

HSA variant binding to mouse FcRn was measured in an ELISA in which recombinant mouse FcRn (R&D Systems, cat #6775-FC-050) was directly immobilized on a Costar Maxisorp® plate. After blocking for 3 hours with PBS+4% fish gelatin, HSA variants at concentrations of 500 nM to 685 pM in PBS+0.1% Tween+0.1% fish gelatin, pH 5.5 were added to each well and incubated for 2.5 hours at RT. Bound HSA was detected with a HRP conjugated goat anti-HSA antibody. The rank order of binding affinity was HSA-13>HSA-7>HSA-11>HSA-5>HSA-wt.

To test whether the in vitro quality of increased affinity corresponds to improved pharmacokinetics (PK) in vivo, selected examples of VSAs, e.g., HSA-5, HSA-11, and HSA-13 and wild type HSA were injected into wild type mice and the plasma concentration monitored over time (to about 170 hours after administration).

In wild type mice, increased affinity in a serum albumin extended its pharmacokinetics (see FIG. 4). The VSAs exhibited a longer half-life and a reduced clearance compared with wild type HSA. The observed improvement in pharmacokinetic properties was correlated with the affinities observed in ELISA experiments that tested the affinities of these VSAs for mouse FcRn. In particular, greater affinity for mouse FcRn was associated with longer half-life and reduced clearance. The highest affinity variant HSA-13 had the most extended PK.

The results obtained in the human-FcRn transgenic mice are shown in FIG. 5. In these mice, the relationship between affinity for FcRn and PK was more complex; the VSAs with the highest affinity for human FcRn did not show the greatest improvement in pharmacokinetics.

Taken in combination, the data from experiments in mice with VSAs indicate that the optimal FcRn affinity for PK extension is determined by a tradeoff between improved endosomal recycling at pH 5.5 and increased surface binding at pH 7.4. In wild type mice, in which wild type HSA binds FcRn weakly (Kd~80 □□□□ the highest affinity variant HSA-13 had the most extended PK. In human-FcRn transgenic mice, in which wild type HSA binds FcRn with higher affinity (Kd-2□M), HSA-13 and HSA-11 bound FcRn too tightly at pH 7.4 (see also FIG. 1), driving rapid clearance and a robust antibody response (see FIG. 5). Medium affinity variants HSA-5 and HSA-7 which have minimal pH 7.4 binding (see also FIG. 1) have extended PK in the FcRn transgenic mouse, as shown in FIG. 5. It should be noted that mouse albumin has a high affinity for human FcRn so it is reasonable to expect that a murine model under predicts the improvement that would be observed in

Example 7: VSAs in a Primate Model

To evaluate the PK of a VSA in a primate model, cynomologus monkeys were injected with an iv bolus dose of 1 mg/kg or 5 mg/kg dose of HSA-7 or wild type HSA (HSA-wt). Two monkeys were analyzed per group by assaying plasma HSA concentration over time using an anti-epitope tag ELISA.

FIG. 6 provides the PK parameters of this experiment, demonstrating that the VSA (HSA-7) has a longer plasma half-life and reduced beta phase clearance in a primate model.

Example 8: Fusion Proteins

When fused to a heterologous polypeptide, protein moieties that extend half-life often do not extend half-life to the same absolute degree as seen with the unfused moiety. This is usually due to active clearance mediated by the heterologous partner. Because it is not clear whether active clearance provides an absolute maximum to the extension seen, or whether the half-life of a fusion is a combination in some way of the half-lives of the two components, we compared wild type HSA fused to IL-2 with a VSA fused to IL-2. Fusion proteins in which human IL-2 is genetically fused to the N- or C-terminus of a selected HSA variant were produced as follows. For N-terminal fusions, cDNA encoding mature human IL-2 was PCR amplified with a 5' primer that introduces 20-40 bp of homology with the app8 yeast leader sequence and a 3' primer that introduces a $(G4S)_3$ linker (SEQ ID NO: 27) followed by 20-40 bp of homology with the N-terminus of mature HSA. For C-terminal fusions, the human IL-2 cDNA was PCR amplified with a 5' primer that introduces 20-40 bp of homology with the C-terminus of HSA followed by a $(G45)_3$ linker (SEQ ID NO: 27) and a 3' primer that introduces 20-40 bp of homology with the stop codon and downstream sequence of the pYC2/CT vector. In both cases, a Quikchange® mutagenesis reaction (Agilent) was then performed in which a selected HSA variant was used as the template and the IL-2 PCR product was used in place of the primers. DpnI treated reactions were transformed into XL-1 Blue E. coli cells (Agilent) and selected on LB+Amp plates. Selected colonies were miniprepped and sequenced. In place of wild type human IL-2 cDNA, DNA encoding a variant of IL-2, such as those described in U.S. Pat. Nos. 7,569,215 and 7,951,360, can be fused to the selected HSA variant.

Plasmids encoding the desired fusion sequence were transformed into BJ5a S. cerevisiae cells using the EZ-yeast kit (Zymo Research) and transformants selected on SDCAA+ura plates. Selected colonies were grown in liquid SDCAA+ura media at 30° C. with shaking at 250 RPM to an OD600~5. Cells were then pelleted at 3000 RPM and resuspended in YPG media to induce albumin expression. After 48 hours in YPG at 20° C./250 RPM, the cells were pelleted at 3000 RPM and the cleared supernatant filter sterilized. The secreted fusion protein was purified by affinity chromatography using CaptureSelect® HSA affinity resin (BAC).

Both mouse and human IL-2 fused to the N-terminus of HSA-wt or HSA-13 through a (G45)2 linker were also cloned into the pLVX-Puro mammalian expression plasmid. Fusion sequences were amplified by PCR using primers that introduced an N-terminal XhoI site and C-terminal MluI site. The PCR product and pLVX-Puro plasmid were both double digested with XhoI/MluI in NEBuffer 3+BSA and ligated with the Quick Ligation kit (New England Biolabs) according to manufacturer's instructions. Plasmids were transiently transfected in Hek-293 cells using PEI as a transfection reagent and cultured for 4-7 days at 37° C./8% $CO_2$.

Example 9: Fusion Expression

Transient transfections were performed in Hek-293 cells to express HSA, IL-2-GS10-HSA, IL-2-GS25-HSA, hepcidin-GS10-HSA, or factor VII-GS10-HSA. Expressed proteins were evaluated using non-reducing SDS-PAGE. All of the tested proteins were expressed and run on the gel in a manner consistent with their expected molecular weights. Subsequently, products of such transient transfections were purified using an anti-HSA resin. Purified products (murine IL-2-HSA wild type and IL-2-HSA-13) were injected iv into mice at a dose of 0.5 mg/kg. The VSA fusion (i.e., HSA-13 fusion) extended the PK of IL-2 to a greater degree than did the fusion to wild type HSA (shown in FIG. 7). The IL2-HSA-13 fusion protein had increased half-life, greater AUC, and reduced clearance.

These data demonstrate that a VSA as described herein can be used to improve the PK of another agent, e.g., a therapeutic protein, e.g., IL-2.

The skilled artisan, having read the above disclosure, will recognize that numerous modifications, alterations of the above, and additional optimization of the above, may be conducted while remaining within the scope of the invention. These include but are not limited to the embodiments that are within the scope of the following claims.

---

What is claimed is:

1. A method of making a variant serum albumin polypeptide (VSA) having an altered binding affinity to FcRn as compared with the binding affinity of a wild type human serum albumin (HSA) to FcRn comprising:

providing a nucleic acid encoding a variant serum albumin polypeptide (VSA) comprising a sequence that has a substitution to A at a position corresponding to position 547 of SEQ ID NO: 2, a substitution to G at a position corresponding to position 505 of SEQ ID NO: 2, and is at least 90% identical but less than 100% identical to amino acid residues 380 to 585 of SEQ ID NO: 2;

introducing the nucleic acid encoding the VSA in a suitable host cell;

culturing the host cell under conditions that allow expression of the polypeptide; and isolating the polypeptide from the host cell or from the host cell growth medium, wherein the VSA binds to FcRn with a higher affinity as compared to the binding affinity of HSA to FcRn.

2. The method of claim 1, wherein the VSA binds to FcRn with a $K_D$ of less than 50 nm.

3. The method of claim 1, wherein the VSA has a longer plasma half-life than HSA.

4. The method of claim 1, wherein the VSA comprises a sequence that has up to 10 amino acid changes in amino acid residues 380 to 585 of SEQ ID NO: 2.

5. The method of claim 1, wherein the VSA comprises a sequence that has up to 9 amino acid changes in amino acid residues 380 to 585 of SEQ ID NO: 2.

6. The method of claim 1, wherein the VSA comprises a sequence that has up to 8 amino acid changes in amino acid residues 380 to 585 of SEQ ID NO: 2.

7. The method of claim 1, wherein the VSA comprises a sequence that has up to 7 amino acid changes in amino acid residues 380 to 585 of SEQ ID NO: 2.

8. The method of claim 1, wherein the VSA comprises a sequence that has up to 6 amino acid changes in amino acid residues 380 to 585 of SEQ ID NO: 2.

9. The method of claim 1, wherein the VSA comprises a sequence that has up to 5 amino acid changes in amino acid residues 380 to 585 of SEQ ID NO: 2.

10. The method of claim 1, wherein the VSA comprises a sequence that has up to 4 amino acid changes in amino acid residues 380 to 585 of SEQ ID NO: 2.

11. The method of claim 1, wherein the VSA comprises a sequence that has up to 3 amino acid changes in amino acid residues 380 to 585 of SEQ ID NO: 2.

12. A method of delivery of a recombinant protein comprising a variant serum albumin polypeptide (VSA) to a subject, the method comprising:
administering to the subject a composition comprising an isolated recombinant protein comprising a variant serum albumin polypeptide (VSA) comprising a sequence that is at least 90% identical but less than 100% identical to amino acid residues 380 to 585 of SEQ ID NO: 2, wherein the VSA comprises a mutation corresponding to position V547 to A and a mutation corresponding to position E505 to G; and
wherein the VSA has an altered binding affinity for human FcRn compared to a wild type human serum albumin (HSA).

13. The method of claim 12, wherein VSA binds to FcRn with a $K_D$ of less than 50 nM.

14. The method of claim 12, comprising at least one additional mutation at a position selected from V418, T420, V424, N429, M446, A449, T467, or A552.

15. The method of claim 12, wherein the VSA comprises a sequence that differs by at least 3 but no more than 10 residues from amino acid residues 380 to 585 of SEQ ID NO: 2.

16. The method of claim 12, further comprising administering a therapeutic agent in combination with the composition, wherein the therapeutic agent comprises a polypeptide component that is fused to the VSA.

17. The method of claim 16, wherein the polypeptide component and the VSA are separated by a linker sequence.

18. The method of claim 16, wherein the polypeptide component and the VSA are covalently linked by a non-peptide bond.

19. The method of claim 16, wherein the polypeptide component and the VSA are non-covalently and stably associated.

20. The method of claim 12, wherein the VSA comprises a sequence that is at least 90% identical to amino acid residues 380 to 585 of SEQ ID NO: 2.

21. The method of claim 12, wherein the VSA comprises a sequence that is at least 95% identical to amino acid residues 380 to 585 of SEQ ID NO: 2.

22. The method of claim 12, wherein the VSA comprises a sequence that is at least 96% identical to amino acid residues 380 to 585 of SEQ ID NO: 2.

23. The method of claim 12, wherein the VSA comprises a sequence that is at least 97% identical to amino acid residues 380 to 585 of SEQ ID NO: 2.

24. The method of claim 12, wherein the VSA comprises a sequence that is at least 98% identical to amino acid residues 380 to 585 of SEQ ID NO: 2.

25. The method of claim 12, wherein the VSA comprises a sequence that is at least 99% identical to amino acid residues 380 to 585 of SEQ ID NO: 2.

26. A method of making a variant serum albumin polypeptide (VSA) associated therapeutic agent, the method comprising:
providing a biologically or pharmaceutically active agent; and
associating the agent with a protein comprising a VSA, which has a substitution to A at a position corresponding to position 547 of SEQ ID NO: 2, a substitution to G at a position corresponding to position 505 of SEQ ID NO: 2, and comprises a sequence that is at least 90% identical but less than 100% identical to amino acid residues 380 to 585 of SEQ ID NO: 2 to generate a VSA associated therapeutic agent.

27. The method of claim 26, further comprising formulating the VSA associated therapeutic agent for administration to a subject.

28. The method of claim 26, wherein the VSA comprises a sequence that has 3 to 10 amino acid changes in amino acid residues 380 to 585 of SEQ ID NO: 2.

29. A method of making a variant serum albumin polypeptide (VSA) associated diagnostic agent, the method comprising:
providing a diagnostic agent; and
associating the diagnostic agent with a protein comprising a VSA, which comprises a sequence that has a substitution to A at a position corresponding to position 547 of SEQ ID NO: 2, a substitution to G at a position corresponding to position 505 of SEQ ID NO: 2, and is at least 90% identical but less than 100% identical to amino acid residues 380 to 585 of SEQ ID NO: 2 to generate a VSA associated diagnostic agent.

30. The method of claim 29, further comprising formulating the VSA associated diagnostic agent for administration to a subject.

31. The method of claim 29, further comprising administering the VSA associated diagnostic agent to a subject and detecting the VSA associated diagnostic agent.

32. The method of claim 31, wherein the subject is imaged.

33. The method of claim 29, wherein the VSA comprises a sequence that has 3 to 10 amino acid changes in amino acid residues 380 to 585 of SEQ ID NO: 2.

* * * * *